US010039787B2

(12) United States Patent
Scott et al.

(10) Patent No.: US 10,039,787 B2
(45) Date of Patent: *Aug. 7, 2018

(54) ACELLULAR PRO-TOLEROGENIC COMPOSITIONS FOR THE TREATMENT/PREVENTION OF AUTO-IMMUNE DISEASES

(71) Applicant: CANADIAN BLOOD SERVICES, Ottawa (CA)

(72) Inventors: Mark D. Scott, Surrey (CA); Duncheng Wang, Greenville, NC (US); Wendy M. Toyofuku, Surrey (CA)

(73) Assignee: CANADIAN BLOOD SERVICES, Ottawa (CA)

( * ) Notice: Subject to any disclaimer, the term of this patent is extended or adjusted under 35 U.S.C. 154(b) by 366 days.

This patent is subject to a terminal disclaimer.

(21) Appl. No.: 14/414,411

(22) PCT Filed: Jul. 12, 2013

(86) PCT No.: PCT/CA2013/050544
§ 371 (c)(1),
(2) Date: Jan. 12, 2015

(87) PCT Pub. No.: WO2014/008609
PCT Pub. Date: Jan. 16, 2014

(65) Prior Publication Data
US 2015/0164948 A1 Jun. 18, 2015

Related U.S. Application Data

(60) Provisional application No. 61/670,694, filed on Jul. 12, 2012, provisional application No. 61/670,636, filed on Jul. 12, 2012.

(30) Foreign Application Priority Data

Jul. 12, 2012 (CA) ...................................... 2782942

(51) Int. Cl.
*A61K 48/00* (2006.01)
*C12N 15/11* (2006.01)
*A61K 35/17* (2015.01)
*C12N 5/0783* (2010.01)
*A61K 39/00* (2006.01)
*C12N 15/113* (2010.01)
*A61K 9/00* (2006.01)
*A61K 35/14* (2015.01)
*A61K 47/48* (2006.01)
*A61K 35/00* (2006.01)
*A61K 35/12* (2015.01)

(52) U.S. Cl.
CPC ............ *A61K 35/17* (2013.01); *A61K 9/0019* (2013.01); *A61K 35/14* (2013.01); *A61K 39/001* (2013.01); *A61K 39/0008* (2013.01); *A61K 47/48776* (2013.01); *C12N 5/0637* (2013.01); *C12N 5/0638* (2013.01); *C12N 15/113* (2013.01); *A61K 35/00* (2013.01); *A61K 47/48215* (2013.01); *A61K 2035/122* (2013.01); *A61K 2035/124* (2013.01); *A61K 2039/515* (2013.01); *A61K 2039/577* (2013.01); *C12N 2310/141* (2013.01); *C12N 2500/50* (2013.01); *C12N 2501/00* (2013.01); *C12N 2501/65* (2013.01); *C12N 2502/1114* (2013.01)

(58) Field of Classification Search
None
See application file for complete search history.

(56) References Cited

U.S. PATENT DOCUMENTS

| 5,908,624 | A | 6/1999 | Scott et al. ................... 424/93.7 |
|---|---|---|---|
| 8,007,784 | B1 | 8/2011 | Scott et al. ................... 424/93.7 |
| 8,067,151 | B2 | 11/2011 | Maurer et al. ..................... 435/2 |
| 2003/0091541 | A1 | 5/2003 | Ikehara et al. ............... 424/93.7 |
| 2005/0196386 | A1 | 9/2005 | Blazar et al. ................ 424/93.7 |
| 2007/0009497 | A1 | 1/2007 | Steinman et al. .......... 424/93.21 |
| 2012/0093936 | A1 | 4/2012 | Lindenberg et al. .......... 424/491 |
| 2014/0017218 | A1* | 1/2014 | Scott ...................... A61K 35/17 424/93.71 |
| 2014/0314866 | A1 | 10/2014 | Brusko et al. ................ 424/501 |

FOREIGN PATENT DOCUMENTS

| WO | WO 97/28254 | 8/1997 | |
|---|---|---|---|
| WO | WO 9742324 A1 * | 11/1997 | ......... A61K 38/2066 |
| WO | WO 02/072799 | 9/2002 | |
| WO | WO 2007/120128 | 10/2007 | |
| WO | WO 2009/106477 | 9/2009 | |
| WO | WO 2011/053223 | 5/2011 | |
| WO | WO 2012/065027 | 5/2012 | |
| WO | WO 2014/008608 | 1/2014 | |
| WO | WO 2015/003240 | 1/2015 | |

OTHER PUBLICATIONS

Extended European Search Report issued in European Application No. 13817292.9, dated Mar. 16, 2016.
Harris et al., "MicroRNAs as Immune Regulators: Implication for Transplantation", *American Journal of Transplantation*, 10(4): 713-719, 2010.

(Continued)

*Primary Examiner* — Amy E Juedes
(74) *Attorney, Agent, or Firm* — Norton Rose Fulbright US LLP

(57) ABSTRACT

This invention relates to pro-tolerogenic preparations capable of increasing the level of regulatory T cells (Treg) and/or decreasing the level of pro-inflammatory T cells (Th17) to induce anergy or immune tolerance. The pro-tolerogenic preparation is enriched in at least one species of miRNAs and is obtained by contacting two allogeneic leukocyte populations wherein at least one of the two populations is modified with a low-immunogenic biocompatible polymer. Therapeutic uses intended for the treatment/prevention of auto-immune diseases of such compositions are also provided.

18 Claims, 30 Drawing Sheets

(56) References Cited

OTHER PUBLICATIONS

Dai et al., "MicroRNA, a new paradigm for understanding immunoregulation, inflammation, and autoimmune diseases", *Translational Research*, 157(4): 163-179, 2011.
Anderson MS, Bluestone JA. "The NOD mouse: a model of immune dysregulation." *Annu Rev Immunol.* 2005;23 :447-85.
Bradley and Scott, "Immune complex binding by immunocamouflaged [poly(ethylene glycol)-grafted]erythrocytes" *Am J Hematol*, 82:970-975, 2007.
Bradley et al., "Interactions of IgM Abo antibodies and complement with methoxy-PEG-modified human RBCs", *Transfusion*, 41:1225-1233, 2001.
Chen and Scott, "Comparative Analysis of Polymer and Linker Chemistries on the Efficacy of Immunocamouflage of Murine Leukocytes". *Artif. Cells Blood Substit. Immobil. Blotechnol.*, 34:305-322, 2006.
Chen and Scott, "Current and future applications of immunological attenuation via pegylation of cells and tissue", *BioDrug*, 15:833-847, 2001.
Chen and Scott, "Immunocamouflage: Prevention of transfusion-induced graft-versus-host disease via polymer grafting of donor cells", *J. Biomed. Mater Res A.*, 67:626-636, 2003.
Le and Scott, "Immunocamouflage: The biophysical basis of immunoprotection by grafted methoxypoly(ethylene glycol) (mPEG)", *Acta Biomater*, 6:2631-2641, 2010.
McCoy and Scott, "Broad-Spectrum Antiviral Prophylaxis: Inhibition of Viral Infection by Polymer Grafting with Methoxypoly (ethylene glycol)", In: *Antiviral drug discovery for emerging diseases and bioterrorism threats.*, PF T, editor, Hoboken, NJ: Wiley & Sons; p. 379-395, 2005.
Murad et al., "Stealth Cells: Prevention of Major Histocompatibility Complex Class II-Mediated T-Cell Activation by Cell Surface Modification", *Blood*, 94:2135-2141, 1999.
Murad et al., "Structural and Functional consequences of Antigenic Modulation of Red Blood Cells With Methoxypoly(Ethylenc Glycol)", *Blood*, 93:2121-2127, 1999.
O'Connell, RM et al. "MicroRNA-155 promotes autoimmune inflammation by enhancing inflammatory T cell development". *Immunity.* Oct. 29, 2010 (Oct. 29, 2010), vol. 33, pp. 607-619, ISSN : 1074-7613.
O'Neill and Bhardwaj, "Differentiation of Peripheral Blood Monocytes into Dendritic Cells", *Curr Protoc Immunol*, Chapter 22, Unit 22F.4.1-4.9, 2005.
Scott et al., "Chemical camouflage of antigenic determinants: Stealth erythrocytes", *Proc. Natl. Acad. Sci. USA*, 94:7566-7571, 1997.

Stahl, HF et al. "miR-155 inhibition Sensitizes CD4+ Th cells for TREG mediated suppression". *PLoS One.* Sep. 24, 2009 (Sep. 24, 2009), vol. 4, p. e7158, ISSN: 1932-6203.
Sutton and Scott, "The effect of grafted methoxypoly(ethylene glycol) chain length on the inhibition of respiratory syncytial virus (RSV) infection and proliferation", *Biomaterials*, 31:4223-4230, 2010.
Viegas, TX et al. "Polyoxazoline : chemistry, properties, and applications in drug delivery." *Bioconjugate Chemistry.* May 18, 2011 (May 18, 2011). vol. 22, pp. 976-986. ISSN : 1043-1802.
Wang D, Toyofuku WM, Chen AM. Scott MD. "Induction of immunotolerance via mPEG grafting to allogeneic leukocytes". *Biomaterials.* Dec. 2011; 32(35):9494-503.
Bradley et al. •"Separation and purification of methoxypoly(ethylene glycol) grafted red blood cells via two-phase partitioning" *J Chromatogr B Analyt Technol Biomed Ufe Sci.*, 807(1):163-8, 2004.
Burrell et al. "Regulatory T Cell Induction, Migration, and Function in Transplantation" *J Immunol*, 189:4705-4711,2012.
Dutheil et al., "Polyethylene glycols interact with membrane glycerophospholipids: is this part of their mechanism for hypothermic graft protection?" *J. Chem. Biol.* Mar. 2009; 2(1): 39-49.
Extended European Search Report issued in European Application No. 13817560.9, dated Mar. 11, 2016.
Extended European Search Report issued in European Application No. 13816754.9, dated Mar. 4, 2016.
Forman et al., *The Journal of Experimental Medicine* 138:672-685, 1973.
Getts et al., "Current landscape for T-cell targeting in autoimmunity and transplantation," *Immunotherapy* 3(7): 853-870, 2011.
Hardy et al., *Nature* 223: 511-512, 1969.
Miroux et al. "In Vitro Effects of Cyclosporine A and Tacrolimus on Regulatory T-Cell Proliferation and Function" *Transplantation*, 94(2): 123-31, 2012.
Morita et al., *Proc. Natl. Acad. Sci.* USA 95:6947-6952, 1998.
Scott et al. "Beyond the red cell: pegylation of other blood cells and tissues" *Transfus Clin Biol.*, II (I ):40-6, 2004.
Scott et al. "Stealth erythrocytes: effects of polymer grafting on biophysical, biological and immunological parameters" *Blood Transfusion*, 1: 244-65, 2003.
Spiegel et al., "Role of microRNAs in immunity and organ transplantation," *Expert Reviews in Molecular Medicine*, 13: e37, 2011.
Wang et al., "The potential utility of methoxypoly (ethylene glycol)-medicated prevention of rhesus blood group antigen RhD recognition in transfusion medicine" *Biomaterials*, 33(10): 3002-12,2012.
Yoshimura et al., *Transplantation* 49(1): 167-171, 1990.
Supplementary European Search Report issued in Application No. 13889025, dated Feb. 10, 2017.
Article 94(3) Communication issued in U.S. Appl. No. 13/817,560, dated Feb. 22, 2017.
Office Action issued in European Application No. 15818906.8, dated Nov. 7, 2017.

* cited by examiner

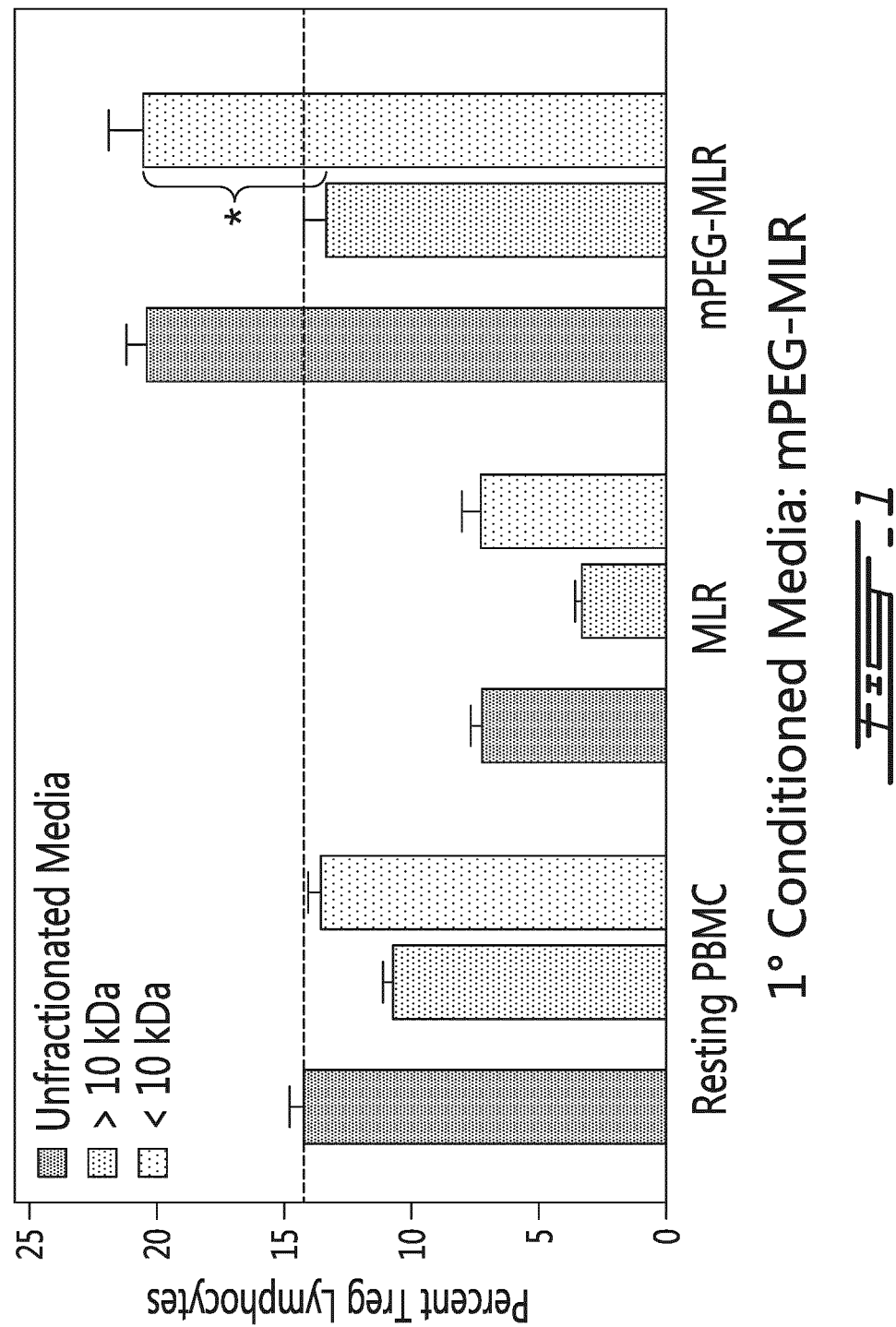

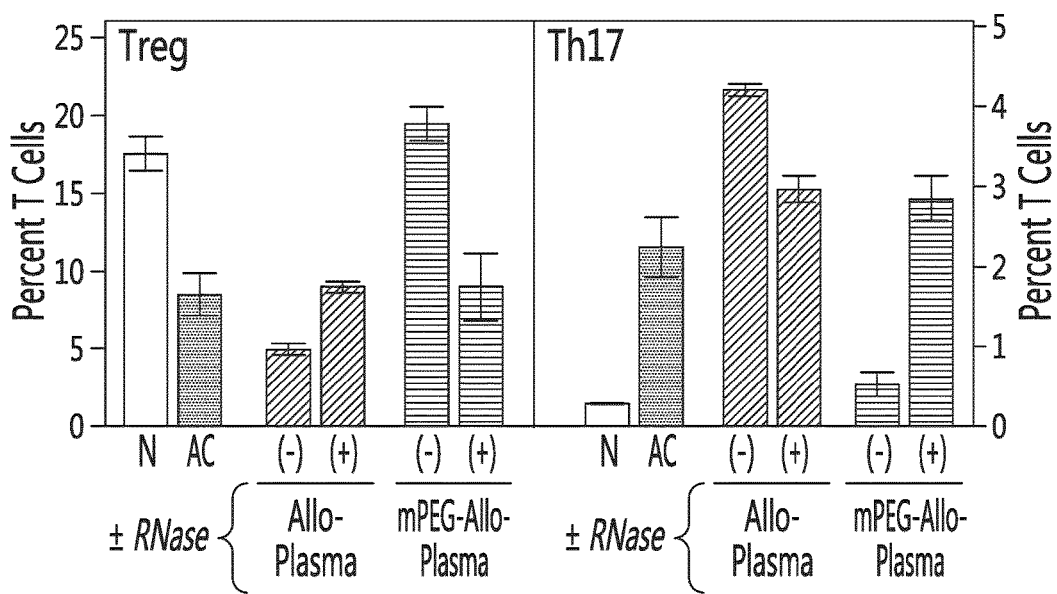

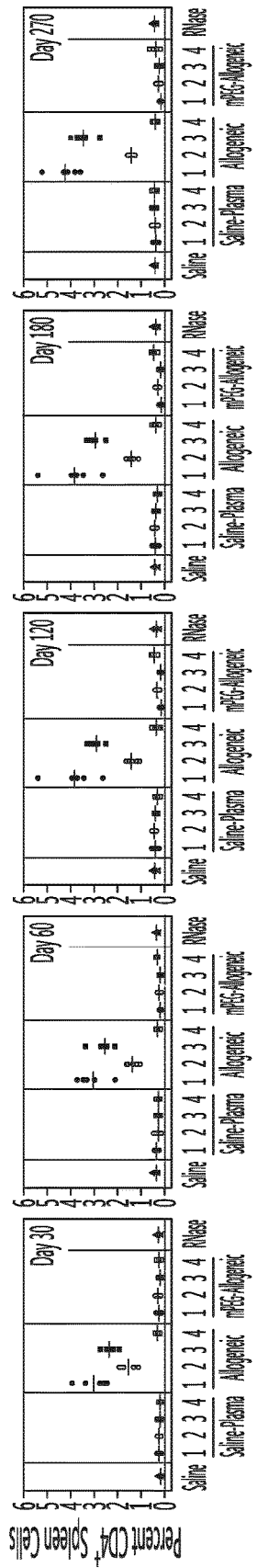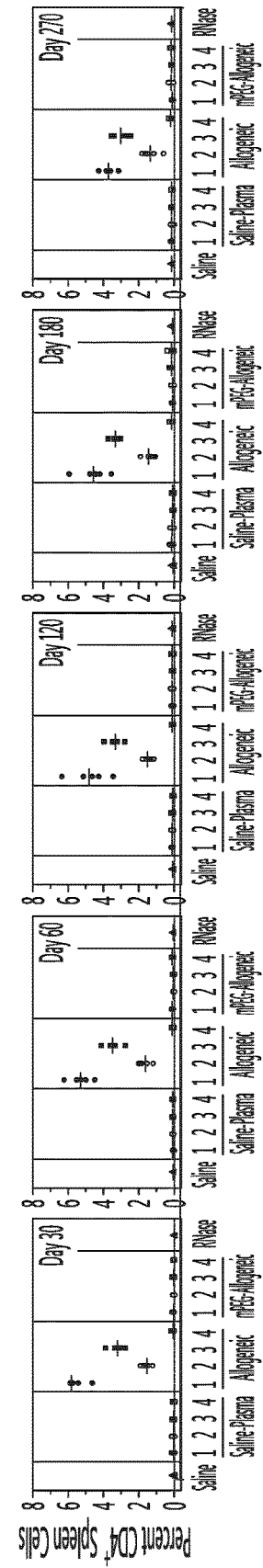

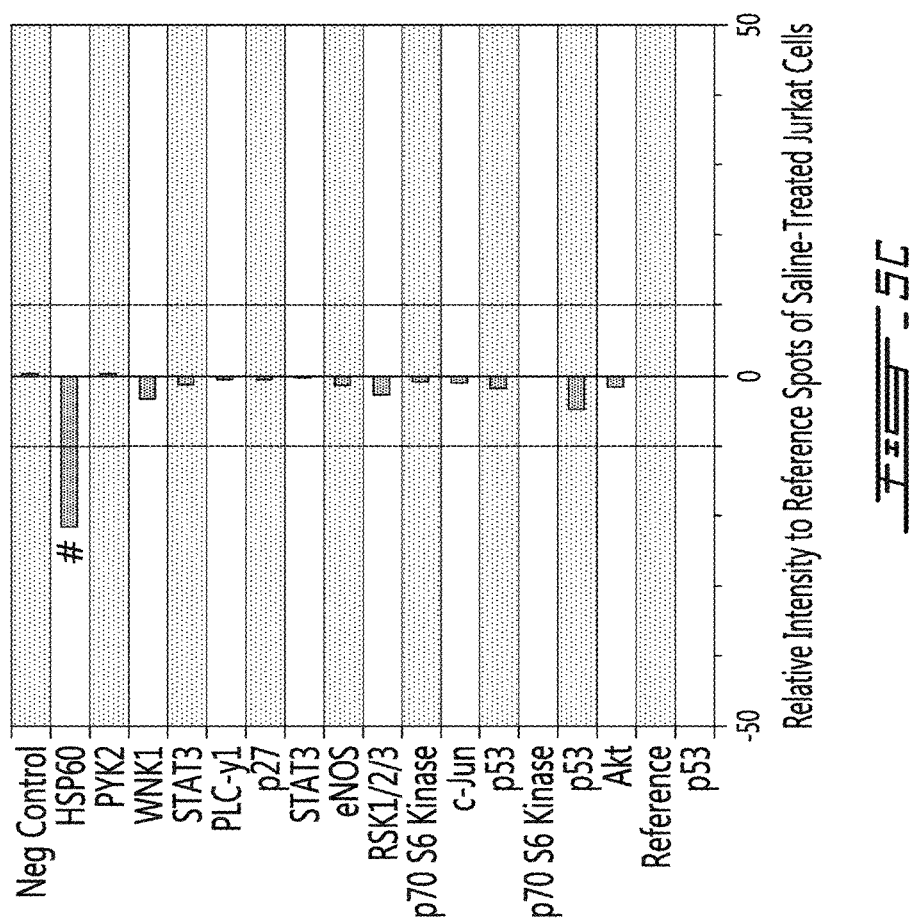

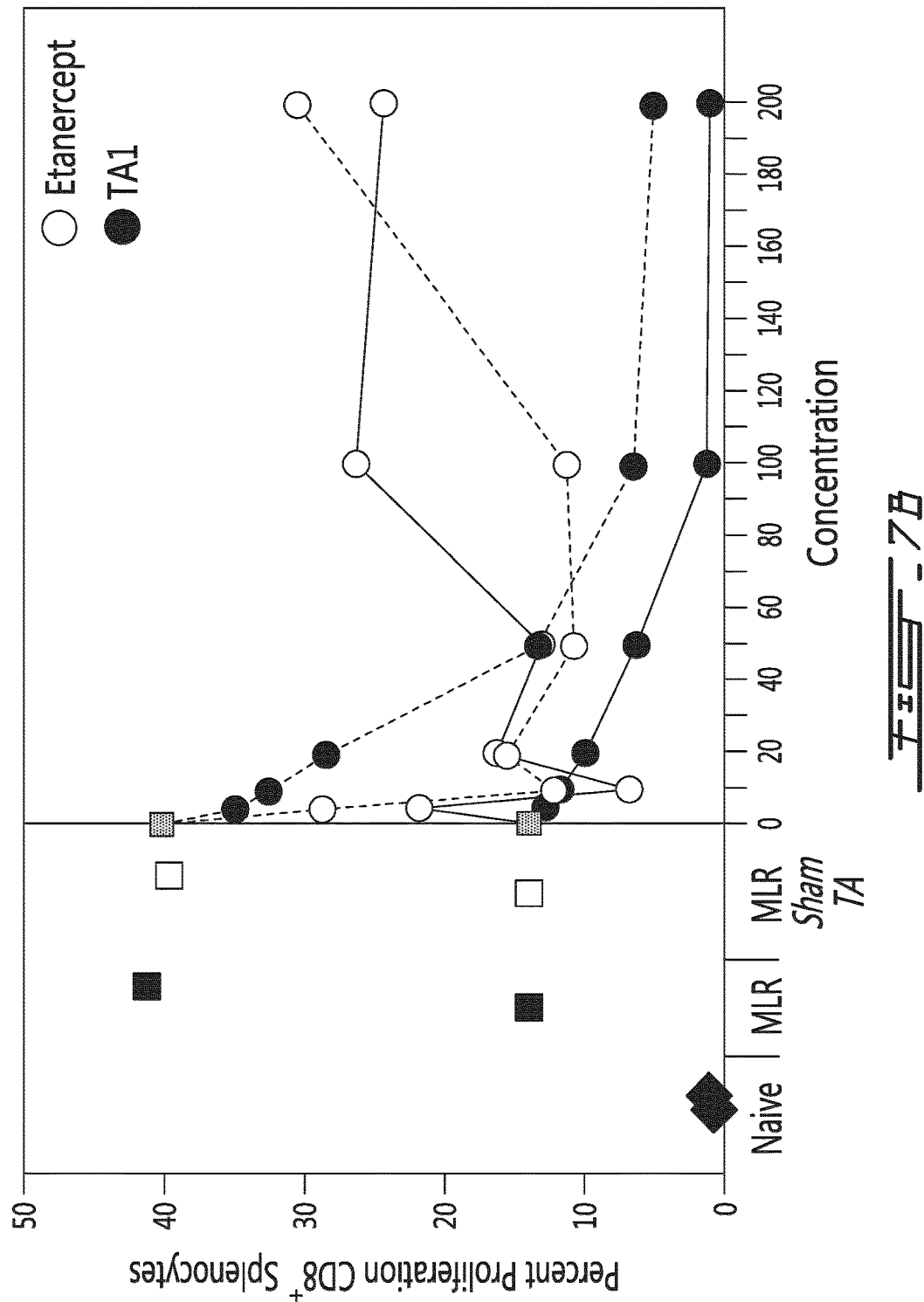

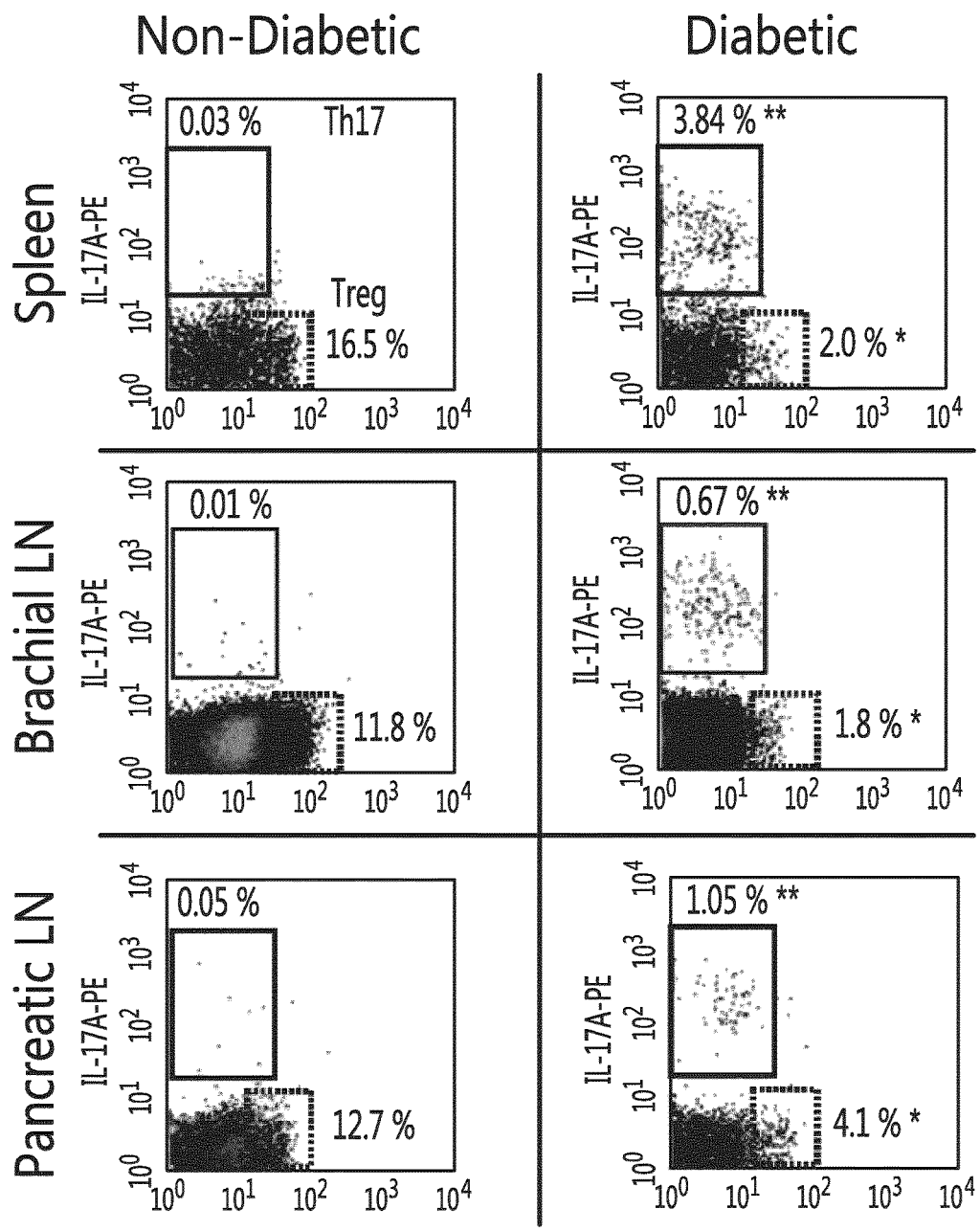

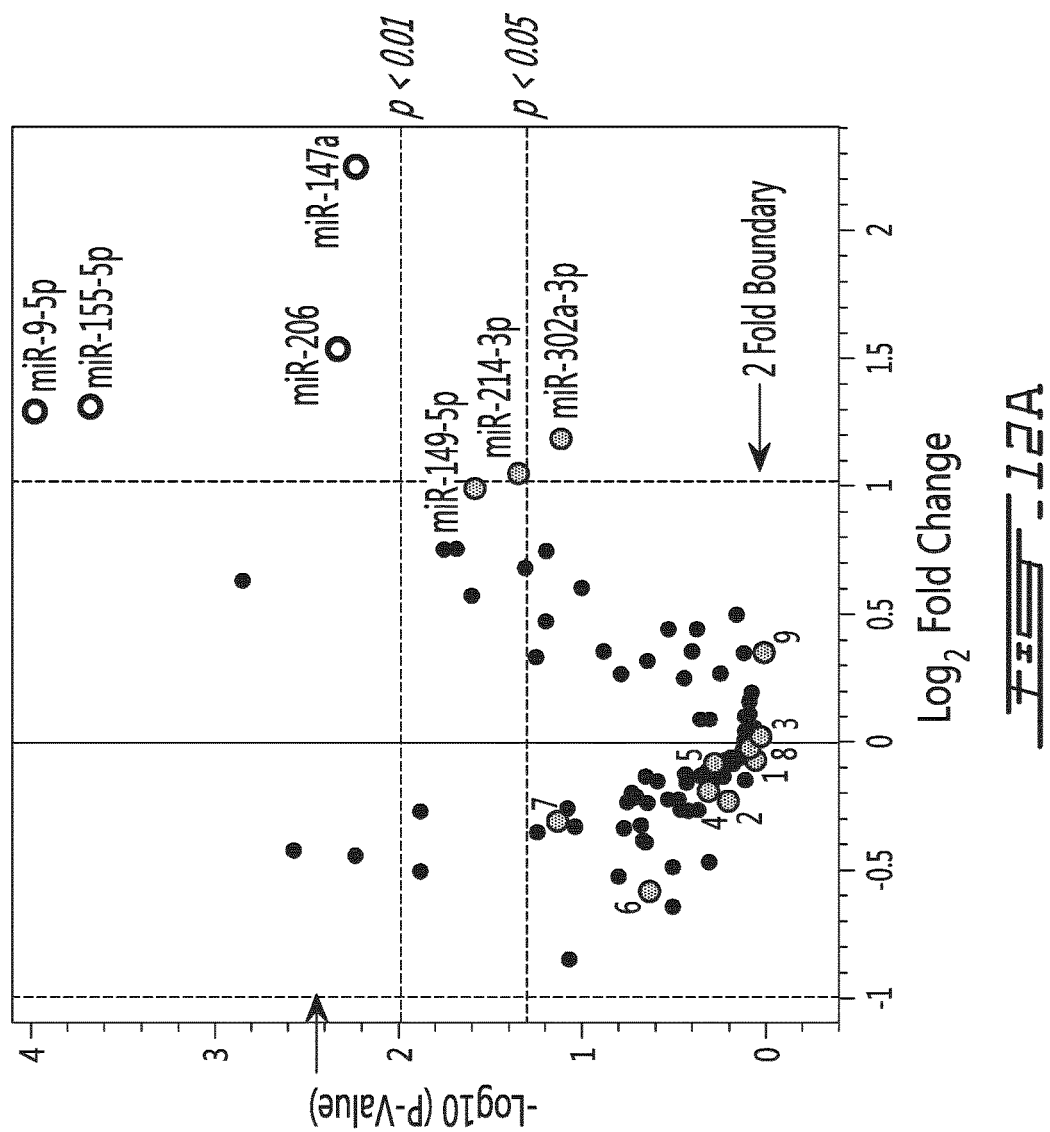

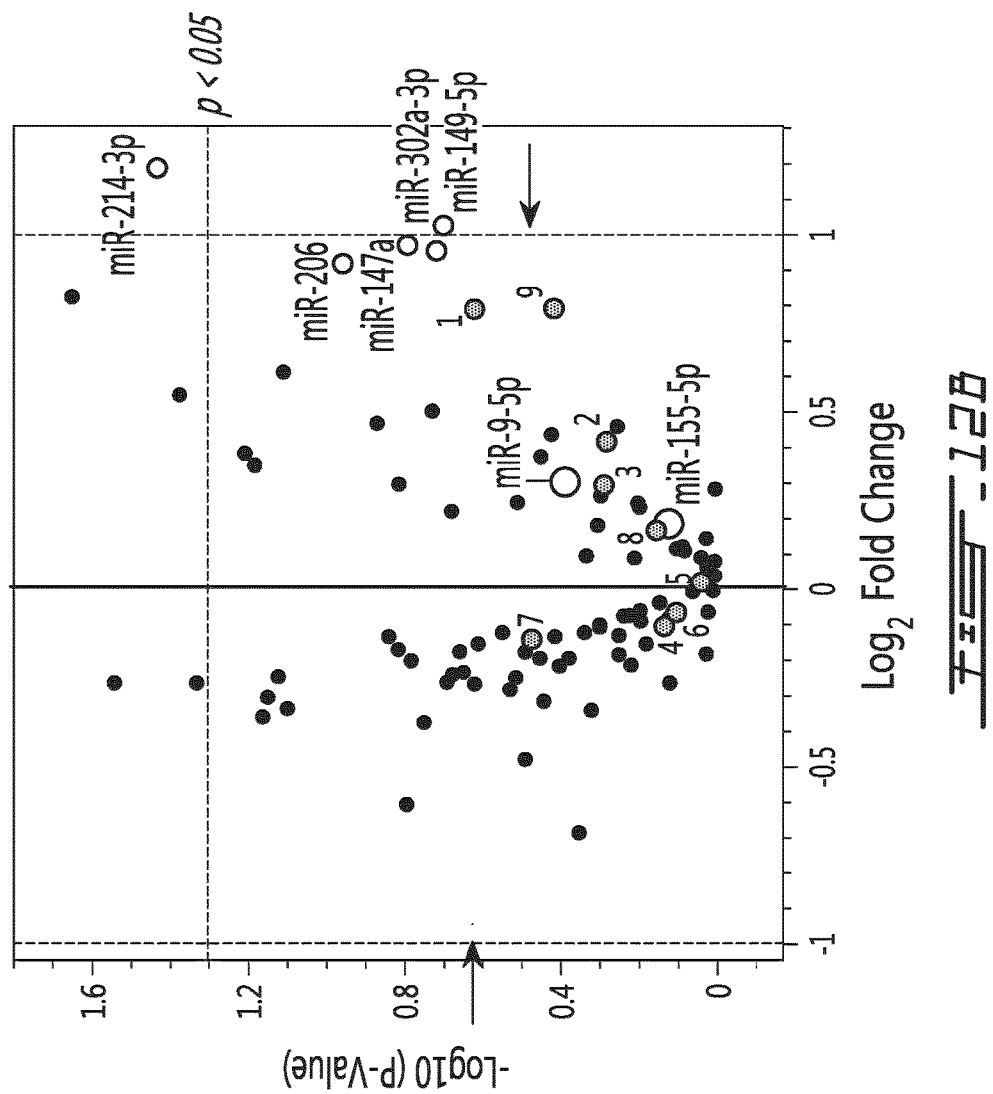

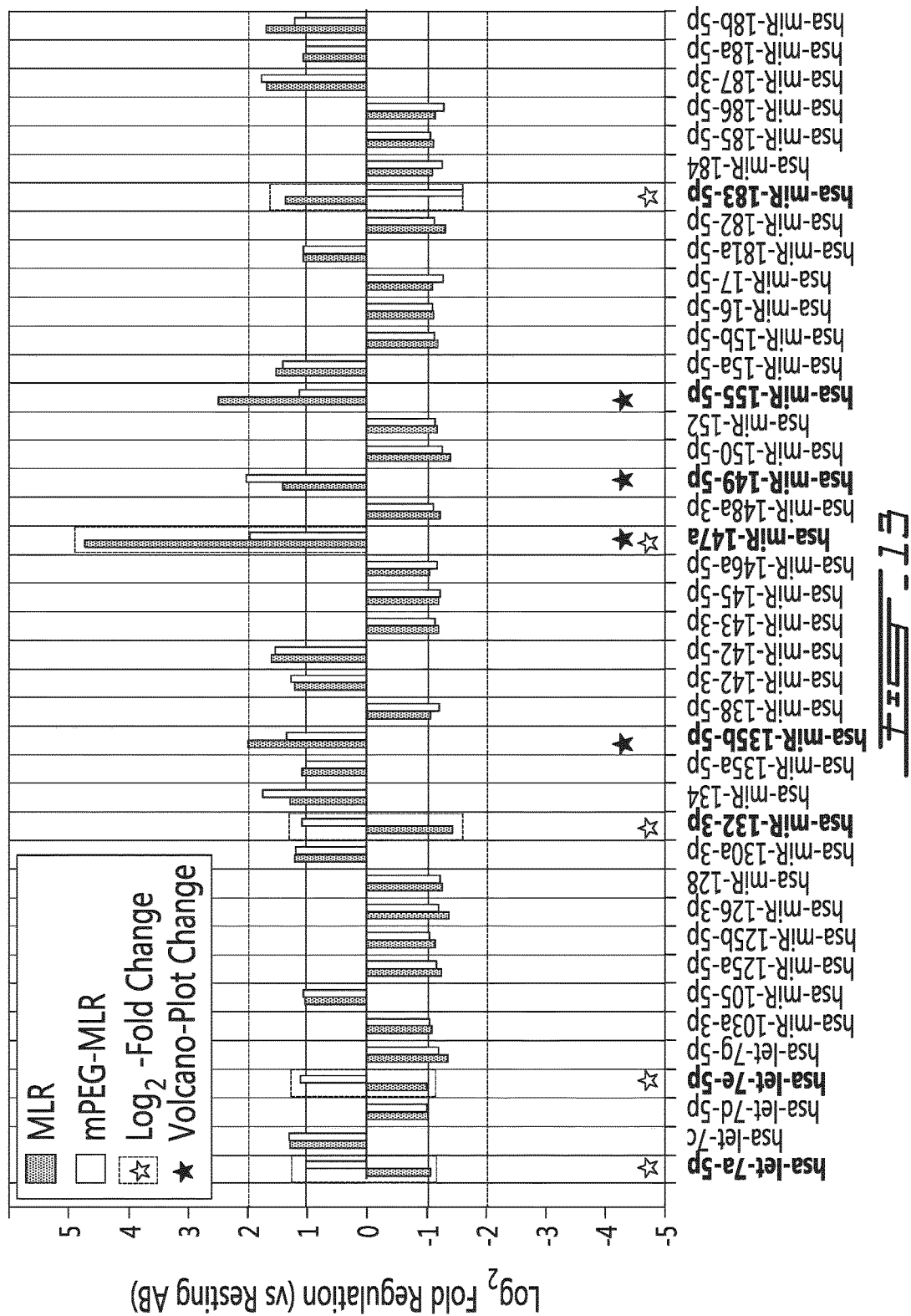

ACELLULAR PRO-TOLEROGENIC COMPOSITIONS FOR THE TREATMENT/PREVENTION OF AUTO-IMMUNE DISEASES

CROSS-REFERENCE TO RELATED APPLICATIONS

This application is a national phase application under 35 U.S.C. § 371 of International Application No. PCT/CA2013/050544 filed Jul. 12, 2013, which claims priority from CA patent application 2782942, U.S. provisional patent application 61/670,636 and U.S. provisional patent application 61/670,694, all filed on Jul. 12, 2012. The entire contents of each of the above-referenced disclosures is specifically incorporated by reference herein without disclaimer.

TECHNOLOGICAL FIELD

The invention provides pro-tolerogenic preparations capable of inducing immune tolerance or anergy. The pro-tolerogenic preparations are RNase-sensitive and can be obtained by enriching the miRNA species expressed when two allogeneic leukocyte populations are contacted and at least one of the population has been modified to bear on its surface a low-immunogenic biocompatible polymer capable of limiting pro-inflammatory allo-recognition.

BACKGROUND

Acute and chronic rejection of donor tissues and organs remains a significant clinical problem in transplantation medicine. Moreover, autoimmune diseases in which one's own immune system recognizes "self" tissues as foreign can also be rejected by similar mechanisms. To minimize or prevent rejection, the administration of immunosuppressive agents is typically required. Acute and chronic rejection are primarily T lymphocyte-mediated events that require allo-geneic recognition of the foreign tissue and the subsequent proliferation of allo-responsive T cells. Indeed, because of the central role of the T cell in rejection, it is the primary target of current immunosuppressive drugs (e.g., cyclosporine A, FK506). In general, these pharmacologic agents target either the T cell activation (e.g., cyclosporine A that inhibits IL-2 responsiveness) or the proliferation (e.g., methotrexate) of the allo-responsive T cells. However all of today's clinically approved anti-rejection drugs are beset by chronic toxicity. Consequently, significant research is underway to identify alternative means of preventing acute and chronic rejection.

A biomaterials approach to modulating immune responsiveness is the direct modification of the surface of donor cells (e.g., erythrocytes, lymphocytes, and pancreatic islets) to prevent allo-recognition (Scott et al., 1997; Murad et al., 1999A; Murad et al., 1999B; Bradley et al., 2001; Chen et al., 2001; Chen et al., 2003; McCoy et al., 2005; Chen et al., 2006; Bradley et al., 2007; Sutton et al., 2010; Le et al., 2010). The polymer modification of the surface of cells is induced by the direct grafting of low immunogenicity polymers to the cell membrane. Previous studies have demonstrated that the polymer modification of the surface of erythrocytes and lymphocytes resulted in the loss of allo-recognition both in vitro and in vivo. Moreover, in contrast to pharmacologic agents, the grafted polymer exhibited both extremely low toxicity and immunogenicity.

It would be highly desirable to be provided with an acellular preparation capable of inducing a state of anergy or immunotolerance by increasing the ratio of the level of regulatory T cells (such as Treg) to pro-inflammatory T cells (such as Th1 and Th17). The acellular preparation could induce anergy or tolerance either by increasing Treg levels, decreasing pro-inflammatory T cell levels or both. This preparation could be useful for treating, preventing and/or alleviating the symptoms associated to an abnormal/excessive immune condition, such as an auto-immune disease, an exacerbated response to a vaccine or a tissue/cell transplantation.

BRIEF SUMMARY

The present invention concern acellular preparations, enriched in at least one miRNA species obtained by contacting two allogeneic leukocyte populations, wherein one of the leukocyte population has been modified to bear on its surface a low-immunogenic biocompatible polymer. The two leukocyte populations are contacted in conditions preventing or limiting pro-inflammatory allo-recognition while allowing pro-tolerogenic allo-recognition.

According to a first aspect, the present invention provides a process for making an acellular pro-tolerogenic composition. Broadly, the process comprises (i) associating a low-immunogenic biocompatible polymer to a cytoplasmic membrane of a first leukocyte to obtain a first modified leukocyte; (ii) contacting the first modified leukocyte with a second leukocyte under conditions to allow a pro-tolerogenic allorecognition to provide a conditioned preparation, wherein the first leukocyte is allogeneic to the second leukocyte; (iii) removing the first modified leukocyte and the second leukocyte from the conditioned preparation under conditions to inhibit RNA degradation so as to obtain a composition enriched in acellular pro-tolerogenic components; and (iv) formulating the composition of step (iii), under conditions to inhibit RNA degradation, in the acellular pro-tolerogenic preparation for administration to a subject. In an embodiment, the process further comprises covalently binding the low-immunogenic biocompatible polymer to a membrane-associated protein of the cytoplasmic membrane of the first leukocyte. In another embodiment, the low-immunogenic biocompatible polymer is a polyethylene glycol (PEG) (a methoxy polyethylene glycol (mPEG) for example). In still another embodiment, the process further comprises covalently binding the mPEG by contacting the first leukocyte with methoxypoly(-ethylene glycol) succinimidyl valerate. In an embodiment, step (ii) occurs in vitro. In such embodiment, the conditioned preparation can be a supernatant of a cell culture of the first leukocyte and the second leukocyte. In a further embodiment, the process further comprises preventing one of the first leukocyte or the second leukocyte from proliferating prior to step (ii). In another embodiment, step (ii) occurs in vivo and comprises administering the first modified leukocyte to a mammal having/bearing the second leukocyte. In such embodiment, the conditioned preparation can be plasma. In yet another embodiment, the process further comprises preventing the first leukocyte from proliferating prior to administration to the mammal.

In an embodiment, step (iii) further comprises removing components having an average molecular weight of more than about 10 kDa from the conditioned preparation or filtering out components having the average molecular weight of more than about 10 kDa from the conditioned preparation. In still another embodiment, step (iii) further comprises enriching the conditioned preparation in at least one miRNA species. In yet another embodiment, step (iv)

further comprises formulating the composition for intravenous administration to the subject. In an embodiment, the first leukocyte and/or the second leukocyte is a T cell (for example a CD4-positive T cell or a CD8-positive T cell).

According to a second aspect, the present invention provides a pro-tolerogenic preparation obtained by the process described herein. In an embodiment, the pro-tolerogenic preparation has at least one miRNA species presented in FIG. 13, at least one of the miRNA species listed any one of Tables 1A to 1D, at least one of the miRNA species listed in any one of Tables 2A to 2D and/or at least one of the miRNA species identified in any one of FIGS. 12A to 12C.

According to a third aspect, the present invention provides a method of increasing a ratio of the level of regulatory T (Treg) cells to the level of pro-inflammatory T cells in a subject in need thereof. Broadly, the method comprises administering to the subject a therapeutic amount of a pro-tolerogenic preparation as described herein and/or obtained by the process described herein so as to increase the ratio in the treated subject. In an embodiment, the increased ratio between the level of Treg cells and the level of pro-inflammatory T cells is for treating, preventing and/or alleviating the symptoms associated to an auto-immune disease afflicting the subject. Auto-immune diseases include, but are not limited to, type I diabetes, rheumatoid arthritis, multiple sclerosis, psoriasis, lupus, immune thrombocytopenia, experimental autoimmune encephalomyelitis, autoimmune uveitis, inflammatory bowel disease, scleroderma and/or Crohn's disease. In another embodiment, the increased ratio between the level of Treg cells and the level of pro-inflammatory T cells is for preventing or limiting the rejection of transplanted cells or tissue in the subject (for example, transplanted cells or tissue which are allogeneic or xenogeneic to the subject). In still another embodiment, the increased ratio between the level of Treg cells and the level of pro-inflammatory T cells is for preventing or limiting graft-versus-host disease in the treated subject. In another embodiment, the process for obtaining the pro-tolerogenic preparation can further comprise formulating the composition for administration prior to the transplantation of the cells or tissue.

According to a fourth aspect, the present invention provides a pro-tolerogenic preparation for increasing a ratio of the level of regulatory T (Treg) cells to the level of pro-inflammatory T cells in a subject. The present invention also provides a pro-tolerogenic preparation for the preparation of a medicament for increasing a ratio of the level of regulatory T (Treg) cells to the level of pro-inflammatory T cells in a subject. The pro-tolerogenic preparation is described herein and/or is obtained by the process described herein. In an embodiment, the pro-tolerogenic preparation is for treating, preventing and/or alleviating the symptoms associated to an auto-immune disease afflicting the subject. Auto-immune diseases include, but are not limited to, type I diabetes, rheumatoid arthritis, multiple sclerosis, psoriasis, lupus, immune thrombocytopenia, experimental autoimmune encephalomyelitis, autoimmune uveitis, inflammatory bowel disease, scleroderma and/or Crohn's disease. In another embodiment, the pro-tolerogenic preparation is for preventing or limiting the rejection of transplanted cells or tissue in the subject (for example, transplanted cells or tissue which are allogeneic or xenogeneic to the subject). In still another embodiment, the pro-tolerogenic preparation is for preventing or limiting graft-versus-host disease in the treated subject. In another embodiment, the process for obtaining the pro-tolereogenic preparation can further comprise formulating the composition for administration prior to the transplantation of the cells or tissue.

Throughout this text, various terms are used according to their plain definition in the art. However, for purposes of clarity, some specific terms are defined below.

Allogeneic cell. A cell is considered "allogeneic" with respect to another cell if both cells are derived from the same animal species but presents sequence variation in at least one genetic locus. A cell is considered "allogeneic" with respect to a subject if the cell is derived from the same animal species as the subject but presents sequence variation in at least one genetic locus when compared to the subject's respective genetic locus. Allogeneic cells induce an immune reaction (such as a rejection) when they are introduced into an immunocompetent host. In an embodiment, a first cell is considered allogeneic with respect to a second cell if the first cell is HLA-disparate (or HLA-mismatched) with the second cell.

Allo-recognition. As it is known in the art, the term "allo-recognition" (also spelled allorecognition) refers to an immune response to foreign antigens (also referred to as alloantigens) from members of the same species and is caused by the difference between products of highly polymorphic genes. Among the most highly polymorphic genes are those encoding the MHC complex which are most highly expressed on leukocytes though other polymorphic proteins may similarly result in immune recognition. These polymorphic products are typically recognized by T cells and other mononuclear leukocytes. In the context of the present invention, the term "pro-inflammatory allo-recognition" refers to an immune response associated with the expansion of pro-inflammatory T cells and/or the differentiation of naïve T cells into pro-inflammatory T cells. Pro-inflammatory allo-recognition in vivo mediates cell or tissue injury and/or death and loss of cell or tissue function. Still in the context of the present invention, the term "pro-tolerogenic allo-recognition" refers to an immune response associated with the expansion of Treg cells and/or the differentiation of naïve T cells into Treg cells. A pro-tolerogenic allo-recognition is usually considered weaker than a pro-inflammatory allo-recognition. Further, an in vivo pro-tolerogenic allo-recognition does not lead to significant cell or tissue injury and/or death nor loss of cell or tissue function.

Anergy and Tolerance. In the present context, the term "anergy" refers to a non-specific state of immune unresponsiveness to an antigen to which the host was previously sensitized to or unsensitized to. It can be characterized by a decrease or even an absence of lymphokine secretion by viable T cells when the T cell receptor is engaged by an antigen. In the present context, the term "tolerance" refers to an acquired specific failure of the immunological mechanism to respond to a given antigen, induced by exposure to the antigen. Tolerance refers to a specific non-reactivity of the immune system to a particular antigen, which is capable, under other conditions, of inducing an immune response. However, in the present context, the terms "anergy" and "tolerance" are used interchangeably since the compositions and methods presented herewith can be used to achieve both anergy and tolerance.

Autologous cell. A cell is considered "autologous" with respect to another cell if both cells are derived from the same individual or from genetically identical twins. A cell is considered "autologous" to a subject, if the cell is derived from the subject or a genetically identical twin. Autologous cells do not induce an immune reaction (such as a rejection) when they are introduced into an immunocompetent host.

Immunogenic cell. A first cell is considered immunogenic with respect to a second cell when it is able to induce an immune response in the latter cell. In some embodiment, the immune response is in vitro (e.g. a mixed lymphocyte reaction) or can be observed in vivo (e.g. in a subject having the second cell and having received the first cell). The second cell can be located in an immunocompetent subject. Preferably, the immune response is a cell-based immune response in which cellular mediator can be produced. In the context of this invention, the immunogenic cells are immune cells, such as white blood cells or leukocytes.

Immunogenic cell culture conditions. A cell culture is considered to be conducted in immunogenic conditions when it allows the establishment of a pro-inflammatory immune response between two distinct and unmodified leukocytes (and, in an embodiment, allo-recognition). Preferably, the pro-inflammatory immune response is a cell-based immune response in which cellular mediator can be produced. For example, the cell culture conditions can be those of a mixed lymphocyte reaction (primary or secondary). When a cell culture is conducted in immunogenic conditions but with leukocytes which have been modified to prevent allo-recognition, no pro-inflammatory immune response is observed. However, when a cell culture is conducted in immunogenic conditions but with leukocytes which have been modified to prevent pro-inflammatory allo-recognition, a non-inflammatory or pro-tolerogenic immune response can be observed (for example a differentiation of naïve T cells to Treg cells and/or expansion of Treg cells).

Leukocyte. As used herein, a leukocyte (also spelled leucocyte) is defined as a blood cell lacking hemoglobin and having a nucleus. Leukocytes are produced and derived from hematopoietic stem cells. Leukocytes are also referred to as white blood cells. Leukocytes include granulocytes (also known as polymorphonuclear leucocytes), e.g. neutrophils, basophils and eosoniphils. Leukocytes also include agranulocytes (or mononuclear leucocytes), e.g. lymphocytes, monocytes and macrophages. Some of the lymphocytes, referred to as T cells (or T-cell), bear on their surface a T-cell receptor. T cell are broadly divided into cells expressing CD4 on their surface (also referred to as CD4-positive cells) and cells expressing CD8 on their surface (also referred to as CD8-positive cells). Some of the lymphocytes, referred to as B cells (or B-cells), bear on their surface a B-cell receptor.

Low-immunogenic biocompatible polymer. As used herein, a "low-immunogenic polymer" refers to a polymer which is not or is unlikely to elicit an immune response in an individual. This low-immunogenic polymer is also capable of masking an antigenic determinant of a cell and lowering or even preventing an immune response to the antigenic determinant when the antigenic determinant is introduced into a subject. A "biocompatible polymer" refers to a polymer which is non-toxic when introduced into a subject. Exemplary low-immunogenic biocompatible polymers includes, but are not limited to, polyethylene glycol (for example methoxypoly(ethylene glycol)), hyperbranched polyglycerol (HPG) and 2-alkyloxazoline (POZ).

Non-proliferative leukocyte. As used herein, the term "non-proliferative leukocyte" refers to a lymphocyte which has been modified to no longer being capable of cellular proliferation (e.g. performing at least one complete division cycle). In some embodiments, this modification may be temporary and the non-proliferative properties of a leukocyte may be limited in time. For example, when a leukocyte is modified from a contact with a pharmacological agent capable of limiting its proliferation, the removal of the pharmacological agent from the cell culture can allow the leukocyte to regain its proliferative properties. In other embodiments, the modification is permanent and the modified leukocyte cannot regain its proliferative properties. For example, when a leukocyte is irradiated, it is not possible for it to regain its proliferative properties. In the context of the present application, the expressions "non-proliferative leukocyte" or "leukocyte limited from proliferating" are used interchangeably.

Peripheral blood mononuclear cells (PBMC). This term refers to the cell population recuperated/derived from the peripheral blood of a subject (usually a mammal such as a human). PBMC usually contains T cells, B cells and antigen presenting cells.

Pharmaceutically effective amount or therapeutically effective amount. These expressions refer to an amount (dose) of an acellular preparation effective in mediating a therapeutic benefit to a patient (for example prevention, treatment and/or alleviation of symptoms of an immune-associated disorder in which the ratio of Tregs to pro-inflammatory T cells is low when compared to sex- and age-matched healthy subjects). It is also to be understood herein that a "pharmaceutically effective amount" may be interpreted as an amount giving a desired therapeutic effect, either taken in one dose or in any dosage or route, taken alone or in combination with other therapeutic agents.

Prevention, treatment and alleviation of symptoms. These expressions refer to the ability of the acellular preparation to limit the development, progression and/or symptomology of a immune-associated disorder associated to an abnormal/excessive immune response (for example prevention, treatment and/or alleviation of symptoms of an immune-associated disorder in which the ratio of Tregs to pro-inflammatory T cells is low when compared to sex- and age-matched healthy subject). Broadly, the prevention, treatment and/or alleviation of symptoms encompasses increasing the levels of Treg cells and/or decreasing the levels of pro-inflammatory T cells. The acellular preparation is considered effective or successful for treating and/or alleviating the symptoms associated with the disorder when a reduction in the pro-inflammatory state (when compared to an untreated and afflicted individual) in the treated individual (previously known to be afflicted with the disorder) is observed. The acellular-based preparation is considered effective or successful for preventing the disorder when a reduction in the pro-inflammatory state (when compared to an untreated and afflicted individual) in the treated individual is observed upon an immunological challenge (such as, for example, an antigenic challenge).

Pro-inflammatory T cells. In the present context, pro-inflammatory T cells are a population of T cells capable of mediating an inflammatory reaction. Pro-inflammatory T cells generally include T helper 1 (Th1 or Type 1) and T helper 17 (Th17) subsets of T cells. Th1 cells partner mainly with macrophage and can produce interferon-γ, tumor necrosis factor-β, IL-2 and IL-10. Th1 cells promote the cellular immune response by maximizing the killing efficacy of the macrophages and the proliferation of cytotoxic $CD8^+$ T cells. Th1 cells can also promote the production of opsonizing antibodies. T helper 17 cells (Th17) are a subset of T helper cells capable of producing interleukin 17 (IL-17) and are thought to play a key role in autoimmune diseases and in microbial infections. Th17 cells primarily produce two main members of the IL-17 family, IL-17A and IL-17F, which are involved in the recruitment, activation and migration of neutrophils. Th17 cells also secrete IL-21 and IL-22.

Regulatory T cells. Regulatory T cells are also referred to as Treg and were formerly known as suppressor T cell. Regulatory T cells are a component of the immune system that suppress immune responses of other cells. Regulatory T cells usually express CD3, CD4, CD8, CD25, and Foxp3. Additional regulatory T cell populations include Tr1, Th3, $CD8^+CD28^-$, $CD69^+$, and Qa-1 restricted T cells. Regulatory T cells actively suppress activation of the immune system and prevent pathological self-reactivity, i.e. autoimmune disease. The critical role regulatory T cells play within the immune system is evidenced by the severe autoimmune syndrome that results from a genetic deficiency in regulatory T cells. The immunosuppressive cytokines TGF-β and Interleukin 10 (IL-10) have also been implicated in regulatory T cell function. Similar to other T cells, a subset of regulatory T cells can develop in the thymus and this subset is usually referred to as natural Treg (or nTreg). Another type of regulatory T cell (induced Treg or iTreg) can develop in the periphery from naïve $CD4^+$ T cells. The large majority of Foxp3-expressing regulatory T cells are found within the major histocompatibility complex (MHC) class II restricted CD4-expressing ($CD4^+$) helper T cell population and express high levels of the interleukin-2 receptor alpha chain (CD25). In addition to the Foxp3-expressing $CD4^+CD25^+$, there also appears to be a minor population of MHC class I restricted $CD8^+$ Foxp3-expressing regulatory T cells. Unlike conventional T cells, regulatory T cells do not produce IL-2 and are therefore anergic at baseline. An alternative way of identifying regulatory T cells is to determine the DNA methylation pattern of a portion of the foxp3 gene (TSDR, Treg-specific-demethylated region) which is found demethylated in Tregs.

Splenocytes. This term refers to the cell population obtained from the spleen of a subject (usually a mammal such as a rodent). Splenocytes usually comprise T cell, B cell as well as antigen presenting cells.

Syngeneic cell. A cell is considered "syngeneic" with respect to a subject (or a cell derived therefrom) if it is sufficiently identical to the subject so as to prevent an immune rejection upon transplantation. Syngeneic cells are derived from the same animal species.

Viable. In the present context, the term "viable" refers to the ability of a cell to complete at least one cell cycle and, ultimately proliferate. A viable cell is thus capable of proliferating. By opposition, the term "non-viable" or "non-proliferative" both refer to a cell which is no longer capable of completing at least one cell cycle. By comparison, the term "cycle arrest" refers to a cell which has been treated to halt its cell cycle progression (usually with a pharmacological agent) but which is still capable of re-entering the cell cycle (usually when the pharmacological agent is removed).

Xenogeneic cell. A cell is considered "xenogeneic" with respect to a subject (or a cell derived from the subject) when it is derived from a different animal species than the subject. A xenogeneic cell is expected to be rejected when transplanted in an immunocompetent host.

BRIEF DESCRIPTION OF THE DRAWINGS

Having thus generally described the nature of the invention, reference will now be made to the accompanying drawings, showing by way of illustration, a preferred embodiment thereof.

FIG. 1 illustrates molecular weight fractionation studies of the acellular preparations demonstrate that the majority of immunomodulatory activity (denoted by *) resides in the low (<10 kDa) molecular weight fraction. Results are shown as percent Treg lymphocytes in function of culture conditions (resting PBMC, MLR or mPEG-MLR) as well as weight fractionation (unfractionated media; >10 kDa fraction; <10 kDa fraction as indicated on the legend). Dashed line represents baseline levels.

FIG. 8 illustrates significant changes in the levels of Th17 and Treg lymphocytes are noted in the spleen (upper panels), brachial lymph node (middle panels) and pancreatic lymph nodes (lower panels) upon conversion of NOD mice from non-diabetic (left panels) to diabetic (right panels). These changes are characterized by dramatically increased Th17 (in the spleen, from 0.03 to 3.84%; in the brachial lymph node, from 0.01% to 0.67%; in the pancreatic lymph node, from 0.05% to 1.05%) and significantly decreased Treg (in the spleen, from 16.5% to 2.0%; in the brachial lymph node from 11.8% to 1.8% and in the pancreatic lymph node, from 12.7% to 4.1%) lymphocytes. Tregs: *, p<0.001 from non-diabetic NOD mice. Th17: ** p<0.001 from non-diabetic NOD mice.

Results are shown as the percentage of CD11c$^+$ cells (in function of total DC cells) in function of treatment. * denotes p<0.001 relative to saline-treated animals.

FIG. 11 illustrates the in vivo effects of TA1 preparations on pro-inflammatory immune cell populations. NOD mice (7 week-old) were treated trice (100 μL i.v. at days 0, 2 and 4) with either saline or TA1. As mice became diabetic (weeks 15-29) or at 30 weeks of age were sacrificed and immune populations were characterized in the spleen, the brachial lymph node, the pancreatic lymph node and, for Th17 cells, the thymus. In this figure, light grey bars refer to saline-treated animals and dark grey bars refers to TA1-treated animals. (A) Results are shown as the percentage of IL-17A$^+$ (Th17) cells (in function of total CD4$^+$ cells) in function of treatment. (B) Results are shown as the percentage of INF-γ$^+$ (Th1) cells (in function of total CD4$^+$ cells) in function of treatment. (C) Results are shown as the percentage of IL-2$^+$ (Th1) cells (in function of total CD4$^+$ cells) in function of treatment. (D) Results are shown as the percentage of TNF-α$^+$ (Th1) cells (in function of total CD4$^+$ cells) in function of treatment. (E) Results are shown as the percentage of IL-12$^+$ (Th1) cells (in function of total CD4$^+$ cells) in function of treatment. (F) Results are shown as the percentage of NK1.1$^+$ cells (in function of total TCR-α/β+ cells) in function of treatment. * denotes p<0.001 relative to saline treated animals.

FIG. 12 provides a comparison of the miRNA populations between different MLR assays. A human PBMC MLR assay (using unmodified (control MLR) or polymer modified leukocyte (mPEG MLR)) was conducted and miRNA content was partially determined. Volcano plots of comparing the miRNA population of the conditioned medium of the control MLR to the one of the supernatant of resting cells (A), comparing the miRNA population of the conditioned medium of a mPEG MLR to the one of the supernatant of resting cells (B) and comparing the miRNA population of the conditioned medium of a mPEG MLR to the one of the conditioned medium of a control MLR(C) are provided. Results are provided in $-\text{Log}_{10}$ (p value) in function of $\text{Log}_2$ fold change. In these volcano plots, the following miRNAs have been identified with numbers:

1 has-miR-298
2 has-miR-34a-5p
3 has-miR-574-3p
4 has-miR-125b-5p
5 has-let-7a-5p
6 has-miR-196a-5p
7 has-miR-148a-3p
8 has-let-7e-5p
9 has-miR-134

Figure 13:
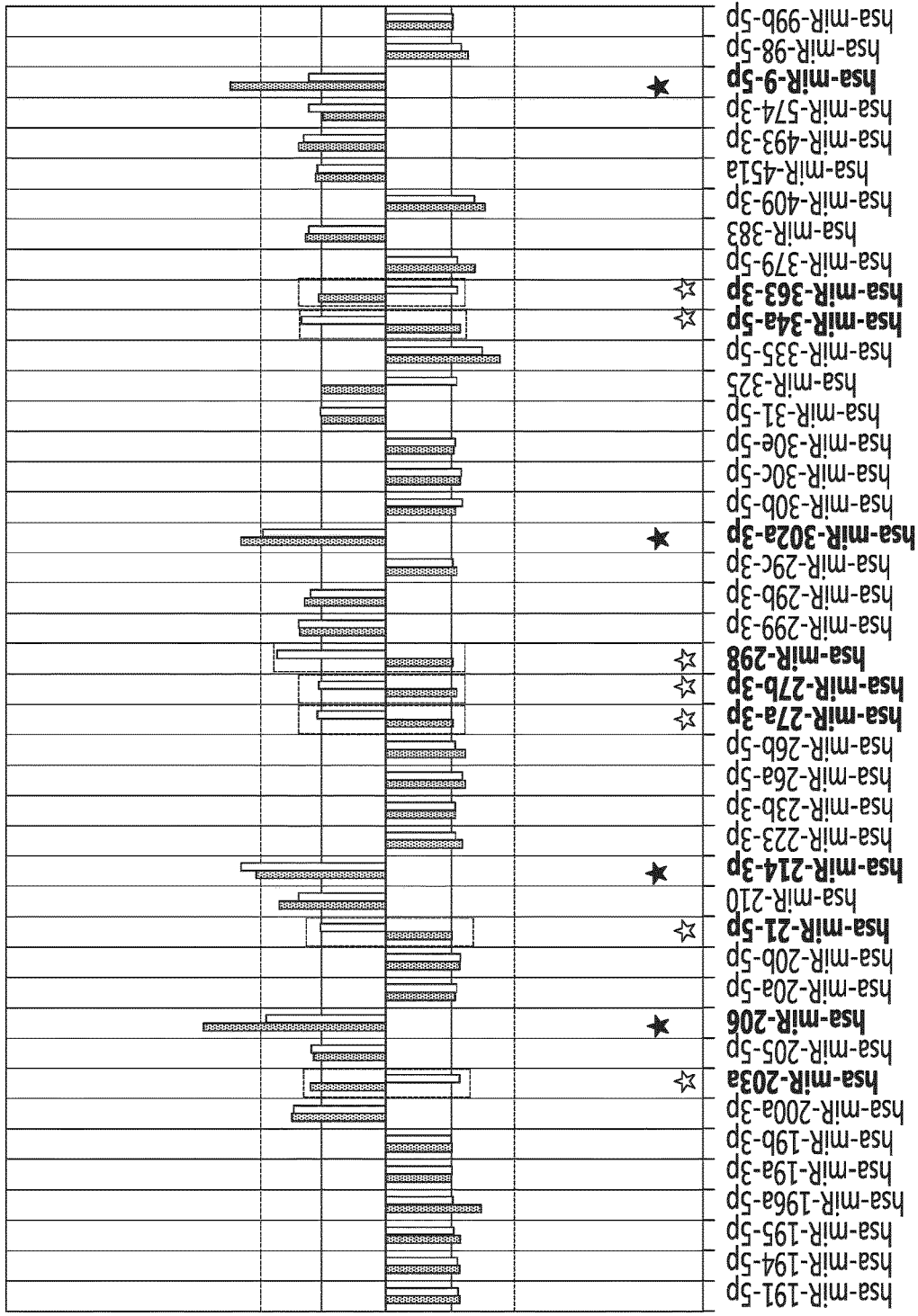

FIG. 13 provides a partial miRNA compositional analysis of the conditioned medium of a mPEG MLR (white bars) and of a control MLR (black bars). Results are provided, for each miRNA, as $\log_2$ fold regulation when compared to the miRNA present in the supernatant of resting cells. White open stars denote $\text{Log}_2$-fold change and black solid stars denote significant changes in volcano plot analysis.

Figure 14:
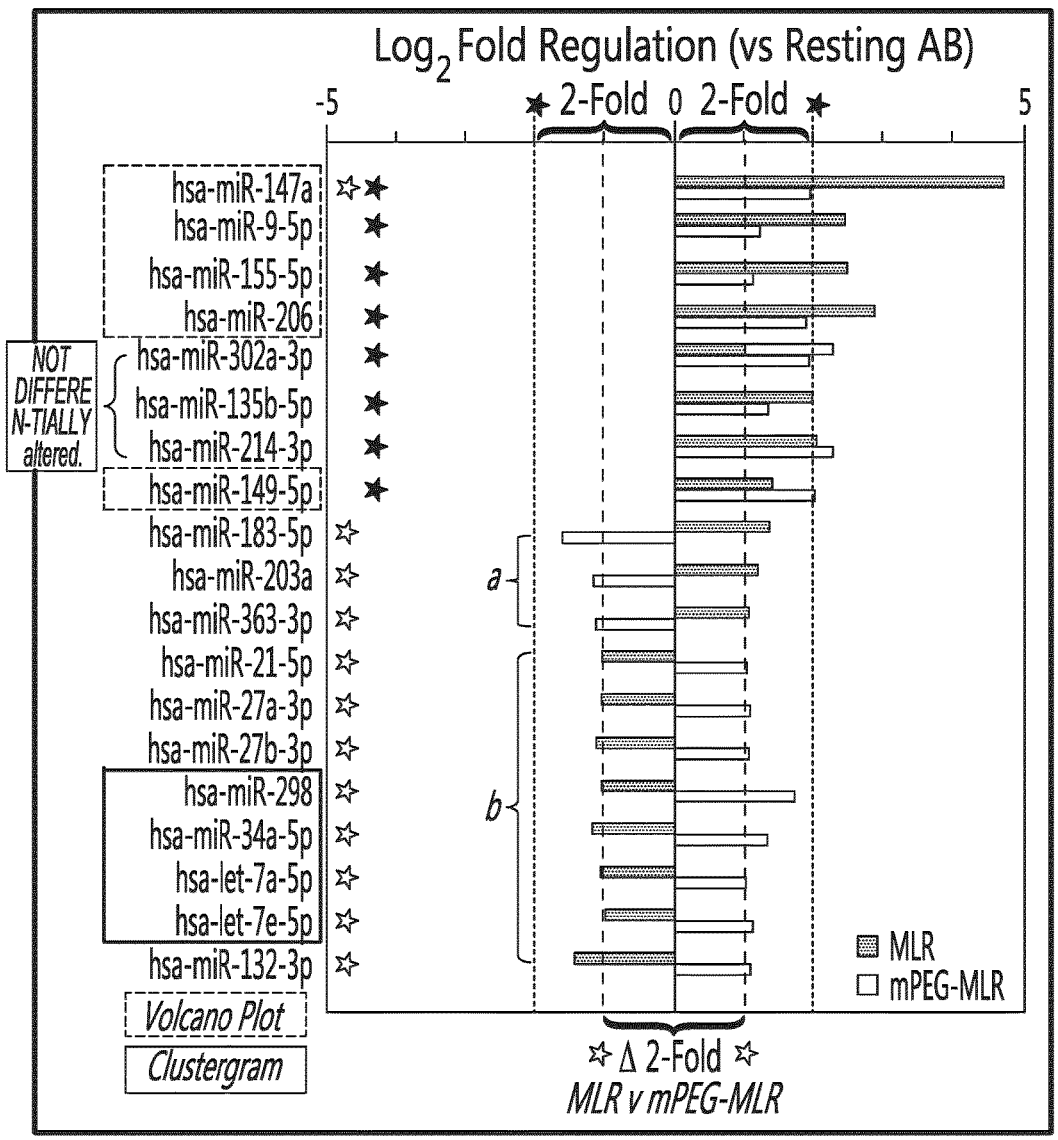

FIG. 14 provides a selection of the miRNA compositional analysis of the conditioned medium of a mPEG MLR (white bars) and of a control MLR (black bars). Results are provided, for each miRNA, as $\log_2$ fold regulation when compared to the miRNA present in the supernatant of resting cells. White open stars denote $\text{Log}_2$-fold change and black solid stars denote significant changes and or clustergram (heatmap) determined miRNA shifts denoted in volcano plot analysis.

DETAILED DESCRIPTION

In accordance with the present invention, there are provided acellular preparations obtained by contacting two distinct allogeneic leukocyte populations wherein at least one of the two leukocyte populations is modified to bear on its surface a low-immunogenic biocompatible polymer. The two leukocyte populations are contacted under conditions so as to allow pro-tolerogenic allo-recognition (e.g. expanding of Treg cells and/or differentiation of naïve cells into T reg cells) and limit pro-inflammatory allo-recognition. The acellular components produced by contacting the two leukocyte populations can optionally be purified or enriched to provide a preparation enriched in miRNAs. In embodiments, the acellular preparation can also be processed to (substantially) remove cells, cells fragments as well as secreted proteins (such as cytokines for example). The contact between the two leukocyte populations can occur in vitro, ex vivo or in vivo.

These acellular preparations induce a state of (complete or partial) immune tolerance, immuno-quiescence or anergy. As such these acellular preparations can be useful for increasing the levels of regulatory T cells and/or decreasing the levels of pro-inflammatory T cells in subjects in need thereof.

The acellular preparations can be obtained by modifying a first leukocyte to bear on its surface a low-immunogenic biocompatible polymer and contacting the first leukocyte with a second leukocyte (considered allogeneic with respect to the first leukocyte). The contact can be made in vitro by co-culturing the first leukocyte and the second leukocyte under conditions so as to allow pro-tolerogenic allo-recognition and limit (or inhibit) pro-inflammatory allo-reocgnition. In such embodiment, the cell culture (or a portion thereof such as the supernatant of the cell culture) is recuperated and processed to substantially remove the cells it may contain to provide the acellular preparation. Alternatively, the contact can be made in vivo by introducing the first leukocyte in a test subject bearing the second leukocyte (such as a non-human animal or mammal). The first leukocyte is allogeneic or xenogeneic to the test subject. In such embodiment, the blood or a blood fraction (such as serum or plasma) is recuperated from the test subject and processed to substantially remove the cells it may contain to provide the acellular preparation.

Since the acellular preparations can optionally be enriched in miRNAs, it is important that the cell culture and/or the blood/blood fraction be processed in conditions so as to retain the integrity of the majority of the miRNA species present, for example by substantially inhibiting RNA degradation. As used herein, the term "substantially inhibiting RNA degradation" indicate that the conditions allow for the degradation of less than 20%, 19%, 18%, 17%, 16%, 15%, 14%, 13%, 12%, 11%, 10%, 9%, 8%, 7%, 6% or 5% of the miRNA population obtained by RNases. RNases include, but are not limited endoribonucleases (e.g., RNase A, RNase H, RNase I, RNase III, RNase L, RNase P, RNase PhyM, RNase T1, RNase T2, RNase U2, RNase V1 and/or RNase V) and exoribonucleases (e.g. polynucleotide pPhosphorylase (PNPase), RNase PH, RNase II, RNase R, RNase D, RNase T, Oligoribonuclease, Exoribonuclease I and/or Exoribonuclease II). Since it is known in the art that miRNAs are, in general, more resistance towards degradation than messenger RNAs, the conditions for obtaining and processing the cell culture/blood can allow for some RNA degradation, preferably limited to the mRNA fraction.

As it will be shown below, acellular preparations obtained from polymer-based bioengineering of allogeneic leukocytic cells provides a significant opportunity to modulate the responsiveness (i.e., immunoquiescent versus pro-inflammatory) of the recipient's immune system. Without wishing to be bound to theory, it is hypothesized that the acellular preparations obtained from using polymer-modified leukocytes can be used to induce Tregs differentiation/expansion and/or attenuate Th17/1 and pro-inflammatory cytokine upregulation to prevent or lower a pro-inflammatory immune response. Moreover, specific NK (natural killer) cell (NK1.1) upregulation is favored in tissues exhibiting autoimmune damage. NK1.1 positive cells are reported to be important in the killing of self-reactive immune cells. Moreover, it is proposed that the acellular preparations obtained from using polymer-modified allogeneic leukocytes can be used therapeutically in various diseases (such as autoimmunity or an excessive immune response) to increase the levels Treg cells and/or decrease pro-inflammatory effector cells, to ultimately increase the ratio of regulatory T cells to pro-inflammatory T cells thereby attenuating the incidence and/or severity of the disease pathology.

Processes for Obtaining Acellular Preparations

The acellular preparations presented described herein can be obtained by contacting two distinct and allogeneic leukocyte populations (referred herein to the first leukocyte and the second leukocyte). The first leukocyte is modified to bear on its surface (and, in some embodiment, to be covalently bound to) a low-immunogenic biocompatible polymer. Optionally, the second leukocyte can also be modified to bear on its surface (and, in some embodiment, to be covalently bound to) a low-immunogenic biocompatible polymer. The two leukocyte populations are contacted under conditions so as to limit (and in some embodiments prevent) pro-inflammatory allo-recognition and to allow pro-tolerogenic allo-recognition.

It is important that the polymer used exhibits both low-immunogenicity and biocompatibility once introduced into a cell culture system or administered to the test subject. Polyethylene glycol (particularly methoxypoly(ethylene glycol)), 2-alkyloxazoline (POZ) and hyperbranched polyglycerol (HPG) are exemplary polymers which all exhibit low immunogenicity and biocompatibility and can be successfully used to modify the first leukocyte (and optionally the second leukocyte). In some embodiments, it is preferable to use a single type of polymer to modify the surface of leukocytes. In other embodiments, it is possible to use at least two distinct types of polymers to modify the surface of the leukocyte.

In an embodiment, the low-immunogenic biocompatible polymer can be covalently associated with the membrane-associated protein(s) of the leukocyte by creating a reactive site on the polymer (for example by deprotecting a chemical group) and contacting the polymer with the leukocyte. For example, for covalently binding a methoxypoly(ethylene glycol) to the surface of a leukocyte, it is possible to incubate a methoxypoly(-ethylene glycol) succinimidyl valerate (reactive polymer) in the presence of the leukocyte. The contact between the reactive polymer and the leukocyte is performed under conditions sufficient for providing a grafting density which will limit/prevent pro-inflammatory allo-recognition and allow pro-tolerogenic allo-recognition. In an embodiment, the polymer is grafted to a viable leukocyte and under conditions which will retain the viability of the leukocyte. A linker, positioned between the surface of the leukocyte and the polymer, can optionally be used. Examples of such polymers and linkers are described in U.S. Pat. Nos. 5,908,624; 8,007,784 and 8,067,151. In another embodiment, the low-immunogenic biocompatible polymer can be integrated within the lipid bilayer of the cytoplasmic membrane of the leukocyte by using a lipid-modified polymer.

As indicated above, it is important that the low-immunogenic biocompatible polymer be grafted at a density sufficient for limiting/preventing pro-inflammatory allo-recognition while allowing pro-tolerogenic allo-recognition of the first leukocyte by the second leukocyte. In an embodiment, the polymer is polyethylene glycol (e.g. linear) and has an average molecular weight between 2 and 40 KDa as well as any combinations thereof. In a further embodiment, the average molecular weight of the PEG to be grafted is at least 2, 3, 4, 5, 10, 15, 20, 25, 30, 35 or 40 kDa. In another embodiment, the average molecular weight of the PEG to be granted is no more than 40, 35, 30, 25, 20, 15, 10, 5, 4, 3, or 2 kDa. In still another embodiment, the grafting concentration of the polymer (per $20 \times 10^6$ cells) is between 1 and 10 mM (preferably between 2.5 to 10 mM). In another embodiment, the grafting concentration of the polymer (per $20 \times 10^6$ cells) is at least 1, 1.5, 2, 2.5, 5, 6, 7, 8, 9 or 10 mM. In still another embodiment, the grafting concentration of the polymer (per $20 \times 10^6$ cells) is no more than 10, 9, 8, 7, 6, 5, 2.5, 2, 1.5 or 1 mM. In order to determine if pro-inflammatory allo-recognition occurs (or is prevented), various techniques are known to those skilled in the art and include, but are not limited to, a standard mixed lymphocyte reaction (MLR), high molecular weight mitogen stimulation (e.g. PHA stimulation) as well as flow cytometry (Chen and Scott, 2006). In order to determine if a pro-tolerogenic allo-recognition occurs (or is prevented), various techniques are known to those skilled in the art and include, but are not limited to, the assessment of the level of expansion and differentiation of Treg cells and or prevention of Th17 expansion/differentiation. In an embodiment, the polymer is selected and grafted to the modified leukocyte to provide a modified leukocyte having a pro-inflammatory/pro-tolerogenic allo-recognition substantially similar to the one observed in a mixed lymphocyte reaction between a first leukocyte modified to be grafted with 20 kDa mPEG at a density of at least 0.5 mM (and preferably 1 mM, even more preferably 2.5 mM) per $20 \times 10^6$ cells and incubated with a second (unmodified) allogeneic leukocyte.

Before or after being modified with a low-immunogenic and biocompatible polymer, the first leukocyte can be optionally modified to refrain from being proliferative. This modification preferably occurs prior to its introduction in a cell culture system or its administration into a test subject. For example, the leukocyte can be irradiated (e.g. γ-irradiation) prior to its introduction in a cell culture system or in the test subject. Upon irradiation, the leukocyte is not considered viable (e.g. capable of proliferation). In an embodiment, polymer grafting can affect the leukocyte viability and be used to refrain the leukocyte from proliferating. Alternatively, leukocyte can be treated with a pharmacological agent which halts cell cycle progression. Upon the administration of such pharmacological agent, the leukocyte is considered viable since it can resume cellular proliferation when the agent is removed from the cell-containing medium.

It is also contemplated that the second leukocyte (which can optionally be modified with the low-immunogenic and biocompatible polymer) be also optionally modified to refrain from being proliferative. For example, the leukocyte can be irradiated (e.g. γ-irradiation) prior to its introduction in a cell culture system or in the test subject. Upon irradiation, the leukocyte is not considered viable (e.g. capable of proliferation). In an embodiment, polymer grafting can affect the leukocyte viability and can be used to refrain the leukocyte from proliferating. Alternatively, leukocyte can be treated with a pharmacological agent which halts cell cycle progression. Upon the administration of such pharmacological agent, the leukocyte is considered viable since it can resume cellular proliferation when the agent is removed from the cell-containing medium. However, when the second leukocyte is modified from being proliferative, it is important the first leukocyte with which it is being contacted remains proliferative.

In order to generate the acellular preparation, it is not necessary to provide homogeneous leukocyte populations. For example, the first leukocyte population (such as, for example a PBMCs or splenocytes) can be introduced in a cell culture system and contacted with a second leukocyte population (such as, for example a PBMCs or splenocytes) or administered to the test subject. However, in some embodiments, it is possible to provide and contact a more homogeneous leukocyte populations. For example, the first leukocyte population can be relatively homogenous (such as, for example, a T cell population) and introduced in a cell culture system comprising a second leukocyte (such as, for example a PBMC or splenocyte) or administered to the test subject. In another example, the first leukocyte population (such as, for example a PBMC or splenocyte) can be introduced in a cell culture system comprising a second leukocyte population which can be relatively homogeneous (such as, for example, a T cell population). In a further example, the first leukocyte population can be relatively homogenous (such as, for example, a T cell population) and introduced in a cell culture system comprising a second leukocyte population which can be relatively homogeneous (such as, for example, a T cell population).

To provide the acellular preparations described herewith, the leukocytes used can be mature leukocytes or be provided in the form of stem cells. For example, leukocytes can be obtained from isolating peripheral blood mononuclear cells (PBMC) from the subject. Optionally, the PBMCs can be differentiated in vitro into dendritic (DC) or DC-like cells. Alternatively, the leukocytes can be obtained from the spleen (e.g. splenocytes). Leukocytes usually include T cells, B cells and antigen presenting cells. For providing the acellular preparations, the leukocytes are not erythrocytes since the polymer-modified erythrocytes are not capable of eliciting a pro-tolerogenic allo-recognition when administered in a test subject. However, traces of erythrocytes in the leukocyte population used are tolerated (for example, less than about 10%, less than about 5% or less than about 1% of the total number of cells in the preparation).

Even though it is not necessary to further purify the leukocytes to provide the acellular preparations, it is possible to use a pure cell population or a relatively homogenous population of cells as leukocytes. This "pure" cell population and "relative homogenous population" of cells can, for example, essentially consist essentially of a single cell type of T cells, B cells, antigen presenting cells (APC) or stem cells. Alternatively, the population of cells can consist essentially of more than one cell type. The population of cells can be obtained through conventional methods (for example cell sorting or magnetic beads). In an embodiment, when the population of cells consist of a single cell type (for example, T cells), the percentage of the cell type with respect to the total population of cells is at least 90%, at least 95% or at least 99%. The relatively homogenous population of cells are expected to contain some contaminating cells, for example less than 10%, less than 5% or less than 1% of the total population of cells.

The first leukocyte and/or second leukocyte can be obtained from any animals, but are preferably derived from mammals (such as, for example, humans and mice). In an embodiment, the first and/or second leukocyte can be obtained from a subject intended to be treated with the acellular preparation.

The first and/or second leukocyte can be expanded in vitro prior to the introduction in a cell culture system or the administration to a test subject.

As indicated above, the first and the second leukocyte are contacted under conditions to limit/prevent pro-inflammatory allo-recognition (e.g. expansion of pro-inflammatory T cells and/or differentiation of naïve T cells in pro-inflammatory T cells) and allow pro-tolerogenic allo-recognition (e.g. expansion of Treg cells and/or differentiation of naïve T cells in Treg cells). When the contact occurs in vitro, it is important that the first leukocyte and the second leukocyte be cultured under conditions allowing physical contact between the two leukocyte populations and for a time sufficient to provide a conditioned medium. As used herein, a conditioned medium refers to physical components of a cell culture (or fraction thereof, such as the cell culture supernatant) obtained by contacting the first and the second leukocyte and having the pro-tolerogenic properties described herein. Usually, the conditioned medium is obtained at least 24 hours after the initial contact between the first and the second leukocyte. In some embodiment, the conditioned medium is obtained at least 48 hours or at least 72 hours after the initial contact between the first and the second leukocyte. In an embodiment, the conditioned medium can be obtained after at least 24 hours of incubating a first leukocyte (for example grafted with a 20 kDa PEG at a density of at 1.0 mM) with a second leukocyte. When the incubation takes place in a 24-well plate, the concentration of each leukocyte population can be at least $1 \times 10^6$ cells.

When the contact occurs in vivo, it is important that the first leukocyte be administered to an immune competent test subject (bearing the second leukocyte) and that the blood or blood fraction be obtained at a later a time sufficient to provide a conditioned blood. The test subject is a subject being immune competent and having a Treg/pro-inflammatory ratio which is substantially similar to age- and sex-matched healthy subjects. As used herein, the conditioned blood refers to physical components present in the blood (or fraction thereof, such as the plasma) obtained by administering the first leukocyte to the immune competent test subject and having the pro-tolerogenic properties described herein. It is recognized by those skilled in the art that the conditioned blood may be obtained more rapidly by increasing the amount of leukocytes being administered or administering more than once (for example one, twice or thrice) the polymer-modified leukocyte. Usually, the conditioned blood is obtained at least one day after the administration of the first leukocyte. In some embodiment, the conditioned blood is obtained at least 2, 3, 4, 5, 6 or 7 days after the administration of the first leukocyte. In an embodiment, the conditioned blood can be obtained by administering at least $5 \times 10^6$ polymer-modified leukocytes (for example grafted with at least 1.0 mM of 20 kDa PEG) to the test subject (e.g. a mice) and recuperating the plasma five days later. In some embodiments, the conditioned blood can be obtained by administering at least $20 \times 10^6$ polymer-modified leukocytes.

As indicated herein, the two leukocyte populations are considered allogeneic (and in some embodiments, xenogeneic). When the acellular preparation is obtained in vivo by, for example, obtaining a conditioned blood/blood fraction by administering the first leukocyte to the test subject, the first leukocyte can be allogeneic or xenogeneic to the test subject. In such embodiment, it is also contemplated that the first leukocyte be autologous, syngeneic, allogeneic or xenogeneic to a treated subject who is going to receive the acellular preparation. When the acellular preparation is obtained in vitro by, for example, obtaining a conditioned medium by co-culturing the first leukocyte with the second leukocyte, the first leukocyte can be allogeneic or xenogeneic to the second leukocyte. In such embodiment, it is also contemplated that the first leukocyte be autologous, syngeneic, allogeneic or xenogeneic to a treated subject who is going to receive the acellular preparation. In addition, it is also contemplated that the second leukocyte be autologous, syngeneic, allogeneic or xenogeneic to a treated subject who is going to receive the acellular preparation.

Once the conditioned medium or the conditioned blood has been obtained it is further processed to substantially remove the cells and cellular debris that can be present. This processing step can be achieved by submitting the conditioned medium or the conditioned blood to a centrifugation step and/or a filtration step. Since the majority of the immuno-modulatory effects of the acellular preparations reside in a fraction sensitive to ribonucleic acid degradation (e.g. RNase degradation), this process step should be conducted in conditions which would substantially limit or even inhibit ribonucleic acid degradation.

The conditioned medium or the conditioned blood is also processed (preferably after the cell/cellular debris) so as to provide an enrichment in at least one miRNA species, and preferably a plurality of miRNA species. As used in the context of this invention, the term "enrichment" refers to the step of increasing the concentration of one or more miRNA species in the acellular preparation when compared to conditioned medium/blood. In an embodiment, the term enrichment refers to the step of increasing, in the acellular preparation, the concentration but not the relative abundance of the miRNA species present in the conditioned medium/blood. In still another embodiment, the enrichment step can comprises substantially isolating the miRNA species from other components that may be present the conditioned medium/blood (e.g. proteins such as cytokines for example). This enrichment step can be completed using various methods known to those skilled in the art, for example, chromatography, precipitation, etc. Since most of the immunomodulatory effects of the acellular preparations reside in a fraction sensitive to ribonucleic acid degradation (e.g. RNase degradation), this process step should be conducted in conditions which would substantially limit or even inhibit ribonucleic acid degradation.

The conditioned medium or the conditioned blood can also be processed to substantially remove the protein components (including the cytokines) and/or the deoxyribonucleic acid components that may be present. Such further purification step can be made by using proteinase (to provide a protein-free acellular preparation), DNAse (to provide a DNA-free acellular preparation), chromatography or filtration (to provide a fraction enriched in size-specific components present in the conditioned medium/blood).

In some embodiments, it is also contemplated that the acellular preparation be submitted to the selective enrichment in components of the conditioned medium/blood having a relative size equal to or lower than about 10 kDa, 9 kDa, 8 kDa, 7 kDa, 6 kDa, 5 kDa, 4 kDa or 3 kDa.

Once the acellular preparation has been obtained, it can be formulated for administration to the subject. The formulation step can comprise admixing the acellular preparation with pharmaceutically acceptable diluents, preservatives, solubilizers, emulsifiers, and/or carriers.

The formulations are preferably in a liquid injectable form and can include diluents of various buffer content (e.g., Tris-HCl, acetate, phosphate), pH and ionic strength, additives such as albumin or gelatin to prevent absorption to surfaces. The formulations can comprise pharmaceutically acceptable solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol).

In addition, if the acellular preparation is destined to be used to prevent an excessive immune reaction triggered by a vaccine, it can be formulated for administration with the vaccine. The acellular preparation can be formulated for simultaneous administration with the vaccine by admixing the vaccine with the acellular preparation. Alternatively, the acellular preparation can be formulated for administration prior to or after the vaccine, for example in a formulation that is physically distinct from the vaccine.

Further, if the acellular preparation is destined to be used to prevent or limit an excessive immune reaction triggered by a transplant, it can be formulated for administration prior to the transplantation. The acellular preparations can be formulated for simultaneous administration with the transplant. Alternatively, the acellular preparations can be formulated for administration prior to or after the transplant. In an embodiment, the acellular preparation can be included in a transplantation medium or a preservation medium destined to receive the donor cells or tissue. In such embodiment, the acellular preparation can induce anergy and/or tolerance of the immune cells or stem cells present in the cells/tissue intended to be transplanted.

Characterization of the miRNA Fraction of the Acellular Preparation

As shown herein, the miRNA fraction of the acellular preparation is associated with the majority of the pro-tolerogenic immunomodulatory effects of the conditioned medium/blood. As also shown herein, the pro-tolerogenic immunomodulatory effects of the miRNA fraction of the acellular preparation are greatly reduced (and even abolished) when the components of the conditioned blood/medium having an average molecular weight lower than about 10 kDa are removed or upon treatment with a ribonucleic acid degradation agent (such as RNase A).

The acellular preparation described herein does comprise a plurality (also referred to a population) of distinct miRNA species whose relative abundance differs from a control medium obtained from a control MLR (e.g. in which two allogeneic leukocyte populations are co-cultured) or a control blood obtained from administering unmodified allogeneic leukocytes to a test subject. The acellular preparation described herein also comprise a plurality (also referred to as a population) of distinct miRNA species whose relative abundance differs from a conditioned medium obtained from resting cells (e.g. a single cultured leukocyte population) or a blood obtained from a naïve test subject. This modulation in the relative abundance of the various miRNA species of the acellular preparation is believed to be tied to the pro-tolerogenic immunomodulatory effects. The increased abundance of single miRNA species, unchanged abundance of single miRNA species and/or decreased abundance of single miRNA species are believe to contribute to the pro-tolerogeneic immunomodulatory effects of the acellular preparation. In an embodiment, in the acellular preparation, the relative pattern of expression of the miRNA species present when compared to the corresponding in the control conditioned medium/blood or medium from resting cells/naïve blood is conserved.

In an embodiment, the acellular preparation comprises at least one miRNA species presented in FIG. 13. In another embodiment, the acellular preparation comprises any combination of at least 2, 3, 4, 5, 10, 15, 20, 25, 30, 30, 35, 40, 45, 50, 55, 60, 65, 70, 75 or 80 of the miRNA species presented in FIG. 13. In still another embodiment, the acellular preparation comprises all the miRNA species presented in FIG. 13. FIG. 13 provides the following miRNA species: hsa-let-7a-5p, hsa-let-7c, hsa-let-7d-5p, hsa-let-7e-5p, hsa-let-7g-5p, hsa-miR-103a-3p, hsa-miR-105-5p, hsa-miR-125a-5p, hsa-miR-125b-5p, hsa-miR-126-3p, hsa-miR-128, hsa-miR-130a-3p, hsa-miR-132-3p, hsa-miR-134, hsa-miR-135a-5p, hsa-miR-135b-5p, hsa-miR-138-5p, hsa-miR-142-3p, hsa-miR-142-5p, hsa-miR-143-3p, hsa-miR-145-5p, hsa-miR-146a-5p, hsa-miR-147a, hsa-miR-148a-3p, hsa-miR-149-5p, hsa-miR-150-5p, hsa-miR-152, hsa-miR-155-5p, hsa-miR-15a-5p, hsa-miR-15b-5p, hsa-miR-16-5p, hsa-miR-17-5p, hsa-miR-181a-5p, hsa-miR-182-5p, hsa-miR-183-5p, hsa-miR-184, hsa-miR-185-5p, hsa-miR-186-5p, hsa-miR-187-3p, hsa-miR-18a-5p, hsa-miR-18b-5p, hsa-miR-191-5p, hsa-miR-194-5p, hsa-miR-195-5p, hsa-miR-196a-5p, hsa-miR-19a-3p, hsa-miR-19b-3p, hsa-miR-200a-3p, hsa-miR-203a, hsa-miR-205-5p, hsa-miR-206, hsa-miR-20a-5p, hsa-miR-20b-5p, hsa-miR-21-5p, hsa-miR-210, hsa-miR-214-3p, hsa-miR-223-3p, hsa-miR-23b-3p, hsa-miR-26a-5p, hsa-miR-26b-5p, hsa-miR-27a-3p, hsa-miR-27b-3p, hsa-miR-298, hsa-miR-299-3p, hsa-miR-29b-3p, hsa-miR-29c-3p, hsa-miR-302a-3p, hsa-miR-30b-5p, hsa-miR-30c-5p, hsa-miR-30e-5p, hsa-miR-31-5p, hsa-miR-325, hsa-miR-335-5p, hsa-miR-34a-5p, hsa-miR-363-3p, hsa-miR-379-5p, hsa-miR-383, hsa-miR-409-3p, hsa-miR-451a, hsa-miR-493-3p, hsa-miR-574-3p, hsa-miR-9-5p, hsa-miR-98-5p and hsa-miR-99b-5p.

In another embodiment, the acellular preparation comprises at least one miRNA species whose relative abundance is increased when compared to a control medium/blood or resting cells/naïve blood. Such miRNA species are listed in Tables 1A to 1D.

TABLE 1A miRNA species whose relative abundance in the acellular preparation is increased when compared to control medium/blood or medium from resting cells/naïve blood as determined in FIG. 13.

hsa-let-7a-5p
hsa-let-7c
hsa-let-7e-5p
hsa-miR-105-5p
hsa-miR-130a-3p
hsa-miR-132-3p
hsa-miR-134
hsa-miR-135a-5p
hsa-miR-135b-5p
hsa-miR-142-3p
hsa-miR-142-5p
hsa-miR-147a
hsa-miR-149-5p
hsa-miR-155-5p
hsa-miR-15a-5p
hsa-miR-181a-5p
hsa-miR-187-3p
hsa-miR-18a-5p
hsa-miR-18b-5p
hsa-miR-200a-3p
hsa-miR-205-5p
hsa-miR-206

TABLE 1A-continued miRNA species whose relative abundance in the acellular preparation is increased when compared to control medium/blood or medium from resting cells/naïve blood as determined in FIG. 13.

hsa-miR-21-5p
hsa-miR-210
hsa-miR-214-3p
hsa-miR-27a-3p
hsa-miR-27b-3p
hsa-miR-298
hsa-miR-299-3p
hsa-miR-29b-3p
hsa-miR-302a-3p
hsa-miR-31-5p
hsa-miR-34a-5p
hsa-miR-383
hsa-miR-451a
hsa-miR-493-3p
hsa-miR-574-3p
hsa-miR-9-5p In a further embodiment, the acellular preparation comprises at least one miRNA species listed Table 1A. In still a further embodiment, the acellular preparation comprises a combination of at least 2, 3, 4, 5, 10, 15, 20, 25, 30, 35 or 37 of any one of the miRNA species listed in Table 1A. In yet a further embodiment, the acellular preparation comprises all the miRNA species listed in Table 1A.

TABLE 1B miRNA species whose relative abundance in the acellular preparation is increased when compared to control medium/blood and whose relative abundance in the control medium/blood is decreased when compared the medium from resting cells/naïve blood as determined in FIG. 13. miRNA species identified with an * show a $\log_2$ fold regulation change or a $p \leq 0.05$ on a volcano plot. miRNA species identified with a # are identified on the volcano plots of FIG. 12.

hsa-let-7a-5p*#
hsa-let-7e-5p*#
hsa-miR-132-3p*
hsa-miR-21-5p*
hsa-miR-27a-3p*
hsa-miR-27b-3p*
hsa-miR-298*#
hsa-miR-34a-5p*#

In a further embodiment, the acellular preparation comprises at least one miRNA species listed Table 1B. In still a further embodiment, the acellular preparation comprises a combination of at least 2, 3, 4, 5, 6 or 7 of any one of the miRNA species listed in Table 1B. In yet a further embodiment, the acellular preparation comprises all the miRNA species listed in Table 1B.

In an embodiment, the acellular preparation comprises at least one (or any combination of) miRNA species listed in Table 1B and showing a $\log_2$ fold regulation change or a $p \leq 0.05$ on a volcano plot (e.g., hsa-let-7a-5p, hsa-let-7e-5p, hsa-miR-132-3p, hsa-miR-21-5p, hsa-miR-27a-3p, hsa-miR-27b-3p, hsa-miR-298 and/or hsa-miR-34a-5p). In still another embodiment, the acellular preparation comprises at least one (or any combination of) miRNA species listed in Table 1B and identified on the volcano plots of FIG. 12 (e.g. hsa-let-7a-5p, hsa-let-7e-5p, hsa-miR-298 and/or hsa-miR-34a-5p).

TABLE 1C miRNA species whose relative abundance in the acellular preparation is increased when compared to the medium/blood from resting cells/naïve blood and whose relative abundance in the control blood/medium is increased when compared to the medium from resting cells/naïve blood as determined in FIG. 13. miRNA species identified with an * show a log$_2$ fold regulation change or a p ≤ 0.05 on a volcano plot. miRNA species identified with a # are identified on the volcano plots of FIG. 12.

hsa-let-7c
hsa-miR-105-5p
hsa-miR-130a-3p
hsa-miR-134#
hsa-miR-135a-5p
hsa-miR-135b-5p*
hsa-miR-142-3p
hsa-miR-142-5p
hsa-miR-147a*
hsa-miR-149-5p*
hsa-miR-155-5p*
hsa-miR-15a-5p
hsa-miR-181a-5p
hsa-miR-187-3p
hsa-miR-18a-5p
hsa-miR-18b-5p
hsa-miR-200a-3p
hsa-miR-205-5p
hsa-miR-206*
hsa-miR-210
hsa-miR-214-3p*
hsa-miR-299-3p
hsa-miR-29b-3p
hsa-miR-302a-3p*
hsa-miR-31-5p
hsa-miR-383
hsa-miR-451a
hsa-miR-493-3p
hsa-miR-574-3p#
hsa-miR-9-5p*

In a further embodiment, the acellular preparation comprises at least one miRNA species listed Table 1C. In still a further embodiment, the acellular preparation comprises a combination of at least 2, 3, 4, 5, 10, 15, 20, 25, or 29 of any one of miRNA species listed in Table 1C. In yet a further embodiment, the acellular preparation comprises all the miRNA species listed in Table 1C.

In an embodiment, the acellular preparation comprises at least one (or any combination of) miRNA species listed in Table 1C and showing a log$_2$ fold regulation change or a p≤0.05 on a volcano plot (e.g. hsa-miR-135b-5p, hsa-miR-147a, hsa-miR-149-5p, hsa-miR-155-5p, hsa-miR-206, hsa-miR-214-3p, hsa-miR-302a-3p and/or hsa-miR-9-5p). In still another embodiment, the acellular preparation comprises at least one (or any combination of) miRNA species listed in Table 1C and identified on the volcano plots of FIG. 12 (e.g. hsa-miR-134 and/or hsa-miR-574-3p).

TABLE 1D

Selection of the miRNA species from Table 1E which show a log$_2$ fold regulation change or a p ≤ 0.05 on a volcano plot.

hsa-miR-135b-5p
hsa-miR-147a
hsa-miR-149-5p
hsa-miR-155-5p
hsa-miR-206
hsa-miR-214-3p
hsa-miR-302a-3p
hsa-miR-9-5p In a further embodiment, the acellular preparation comprises at least one miRNA species listed Table 1D. In still a further embodiment, the acellular preparation comprises a combination of at least 2, 3, 4, 5, 6 or 7 of any one of miRNA species listed in Table 1D. In yet a further embodiment, the acellular preparation comprises all the miRNA species listed in Table 1D.

In another embodiment, the acellular preparation comprises at least one miRNA species whose relative abundance is decreased when compared to a control medium/blood or the medium from resting cells/naïve blood. Such miRNA species are listed in Tables 2A to 2D.

TABLE 2A miRNA species whose relative abundance in the acellular preparation is decreased when compared to control medium/blood or medium from resting cells/naïve blood as determined in FIG. 13.

hsa-let-7d-5p
hsa-let-7g-5p
hsa-miR-103a-3p
hsa-miR-125a-5p
hsa-miR-125b-5p
hsa-miR-126-3p
hsa-miR-128
hsa-miR-138-5p
hsa-miR-143-3p
hsa-miR-145-5p
hsa-miR-146a-5p
hsa-miR-148a-3p
hsa-miR-150-5p
hsa-miR-152
hsa-miR-15b-5p
hsa-miR-16-5p
hsa-miR-17-5p
hsa-miR-182-5p
hsa-miR-183-5p
hsa-miR-184
hsa-miR-185-5p
hsa-miR-186-5p
hsa-miR-191-5p
hsa-miR-194-5p
hsa-miR-195-5p
hsa-miR-196a-5p
hsa-miR-19a-3p
hsa-miR-19b-3p
hsa-miR-203a
hsa-miR-20a-5p
hsa-miR-20b-5p
hsa-miR-223-3p
hsa-miR-23b-3p
hsa-miR-26a-5p
hsa-miR-26b-5p
hsa-miR-29c-3p
hsa-miR-30b-5p
hsa-miR-30c-5p
hsa-miR-30e-5p
hsa-miR-325
hsa-miR-335-5p
hsa-miR-363-3p
hsa-miR-379-5p
hsa-miR-409-3p
hsa-miR-98-5p
hsa-miR-99b-5p In a further embodiment, the acellular preparation comprises at least one miRNA species listed Table 2A. In still a further embodiment, the acellular preparation comprises a combination of at least 2, 3, 4, 5, 10, 15, 20, 25, 30, 35, 40, 45 or 46 of any one of miRNA species listed in Table 2A. In yet a further embodiment, the acellular preparation comprises all the miRNA species listed in Table 2A.

TABLE 2B miRNA species whose relative abundance in the acellular preparation is decreased when compared to control medium/blood and whose relative abundance in the control medium/blood is increased when compared the medium from resting cells/naïve blood as determined in FIG. 13. miRNA species identified with an * show a log$_2$ fold regulation change or a p ≤ 0.05 on a volcano plot.

hsa-miR-183-5p*
hsa-miR-203a*
hsa-miR-325
hsa-miR-363-3p*

In a further embodiment, the acellular preparation comprises at least one miRNA species listed Table 2B. In still a further embodiment, the acellular preparation comprises a combination of at least 2 or 3 of any one of the miRNA species listed in Table 2B. In yet a further embodiment, the acellular preparation comprises all the miRNA species listed in Table 2B.

In an embodiment, the acellular preparation comprises at least one miRNA species (or any combination thereof) listed in Table 2B and showing a log$_2$ fold regulation change or a p≤0.05 on a volcano plot (e.g. hsa-miR-183-5p, hsa-miR-203a and/or hsa-miR-363-3p).

TABLE 2C

Selection of the miRNA species from Table 2B which show a log$_2$ fold regulation change or a p ≤ 0.05 on a volcano plot.

hsa-miR-183-5p
hsa-miR-203a
hsa-miR-363-3p

In a further embodiment, the acellular preparation comprises at least one miRNA species listed Table 2C. In still a further embodiment, the acellular preparation comprises a combination of at least 2 of any one of miRNA species listed in Table 2C. In yet a further embodiment, the acellular preparation comprises all the miRNA species listed in Table 2C.

TABLE 2D miRNA species whose relative abundance in the acellular preparation is decreased when compared to the medium from resting cells/naïve blood and whose relative abundance in the control blood/medium is decreased when compared to the medium from resting cells/naïve blood in FIG. 13. miRNA species identified with an * show a log$_2$ fold regulation change or a p ≤ 0.05 on a volcano plot. miRNA species identified with a # are identified on the volcano plots of FIG. 12.

hsa-let-7d-5p
hsa-let-7g-5p
hsa-miR-103a-3p
hsa-miR-125a-5p
hsa-miR-125b-5p#
hsa-miR-126-3p
hsa-miR-128
hsa-miR-138-5p
hsa-miR-143-3p
hsa-miR-145-5p
hsa-miR-146a-5p
hsa-miR-148a-3p#
hsa-miR-150-5p
hsa-miR-152
hsa-miR-15b-5p
hsa-miR-16-5p
hsa-miR-17-5p
hsa-miR-182-5p
hsa-miR-184
hsa-miR-185-5p

TABLE 2D-continued miRNA species whose relative abundance in the acellular preparation is decreased when compared to the medium from resting cells/naïve blood and whose relative abundance in the control blood/medium is decreased when compared to the medium from resting cells/naïve blood in FIG. 13. miRNA species identified with an * show a log$_2$ fold regulation change or a p ≤ 0.05 on a volcano plot. miRNA species identified with a # are identified on the volcano plots of FIG. 12.

hsa-miR-186-5p
hsa-miR-191-5p
hsa-miR-194-5p
hsa-miR-195-5p
hsa-miR-196a-5p#
hsa-miR-19a-3p
hsa-miR-19b-3p
hsa-miR-20a-5p
hsa-miR-20b-5p
hsa-miR-223-3p
hsa-miR-23b-3p
hsa-miR-26a-5p
hsa-miR-26b-5p
hsa-miR-29c-3p
hsa-miR-30b-5p
hsa-miR-30c-5p
hsa-miR-30e-5p
hsa-miR-335-5p
hsa-miR-379-5p
hsa-miR-409-3p
hsa-miR-98-5p
hsa-miR-99b-5p In a further embodiment, the acellular preparation comprises at least one miRNA species listed Table 2D. In still a further embodiment, the acellular preparation comprises a combination of at least 2, 3, 4, 5, 10, 15, 20, 25, 30, 35, 40 or 41 of any one of miRNA species listed in Table 2D. In yet a further embodiment, the acellular preparation comprises all the miRNA species listed in Table 2D.

In an embodiment, the acellular preparation comprises at least one miRNA species (or any combination thereof) listed in Table 2D and are identified on the volcano plots of FIG. 12 (e.g. hsa-miR-125b-5p, hsa-miR-148a-3p and/or hsa-miR-196a-5p).

It is contemplated that the acellular preparation comprises at least one (and in an embodiment any combination of) miRNAs species from any one of Tables 1A to 1D and at least one (and in an embodiment any combination of) miRNAs species from any one of Tables 2A to 2D.

In yet another embodiment, the acellular preparation can comprise at least one of the miRNA species identified in the volcano plots of FIG. 12. For example, the acellular preparation can comprise at least one (or any combination of) miRNA species from the following list: has-miR-298, has-miR-34a-5p, has-miR-574-3p, has-miR-125b-5p, has-let-7a-5p, has-miR-196a-5p, has-miR-148a-3p, has-let-7e-5p and has-miR-134. In still another embodiment, the acellular preparation can comprise at least one (or any combination of) miRNA species identified on FIG. 12 and having a relative abundance which is increased in the acellular preparation when compared to the control medium/blood (e.g. miR-298, has-miR-34a-5p, has-miR-574-3p, has-let-7a-5p, has-miR-196a-5p, has-miR-148a-3p, has-let-7e-5p and/or has-miR-134). In still another embodiment, the acellular preparation can comprise the miRNA species identified on FIG. 12 and having a relative abundance which is increased in the acellular preparation and the control medium/blood when compared to the resting cells/naïve blood (e.g. has-miR-125b-5p).

Figure 12C:
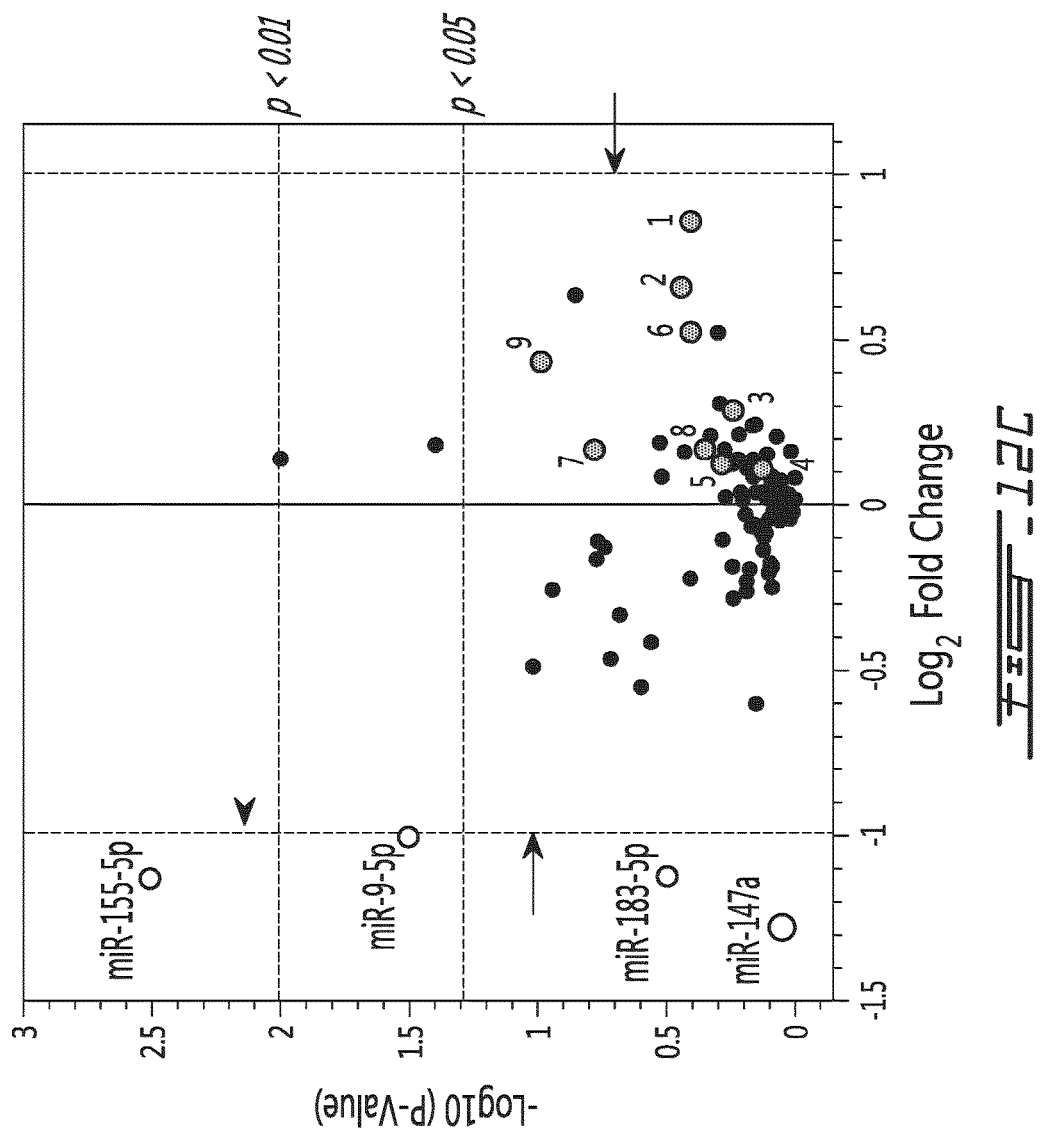

In yet another embodiment, the acellular preparation comprises at least one (or any combination of) miRNA species presented on FIG. 12A which exhibits at least a $\log_2$ fold modulation in abundance (e.g. miR-302a-3p, miR214-3p, miR-147a, miR206, miR 155-5p and/or miR-9-5p). In yet still another embodiment, the acellular preparation comprises at least one (or any combination of) of miRNA species presented on FIG. 12A which exhibits at least $p \leq 0.05$ (e.g. miR214-3p, miR-147a, miR206, miR 155-5p and/or miR-9-5p). In yet another embodiment, the acellular preparation comprises at least one (or any combination of) miRNA species presented on FIG. 12B which exhibits at least a $\log_2$ fold modulation in abundance (e.g. miR-149-5p and/or miR-214-3p). In yet still another embodiment, the acellular preparation comprises the miRNA species presented on FIG. 12B which exhibits at least $p \leq 0.05$ (e.g. miR-214-3p). In yet another embodiment, the acellular preparation comprises at least one (or any combination of) miRNA species presented on FIG. 12C which exhibits at least a $\log_2$ fold modulation in abundance (e.g. miR-147a, miR-183-5p, miR-9-5p and/or miR-155-5p). In yet still another embodiment, the acellular preparation comprises at least one (or any combination of) miRNA species presented on FIG. 12C which exhibits at least $p \leq 0.05$ (e.g. miR-9-5p and/or miR-155-5p).

It is contemplated that the acellular preparation comprises at least one (and in an embodiment any combination of) miRNAs species from any one of Tables 1A to 1D, at least one (and in an embodiment any combination of) miRNAs species from any one of Tables 2A to 2D and at least one (and in an embodiment any combination of) miRNA species identified in any one of the FIG. 12A to 12C.

Methods for Modulating the Treg/Pro-Inflammatory T Cells Ratio

The present invention also provides methods and acellular preparations for increasing the ratio of the level of regulatory T cells with respect to the level of pro-inflammatory T cells. In the present invention, the ratio can be increased either by augmenting the level of regulatory T cells in the subject or decreasing the level of pro-inflammatory T cells in the treated subject. Alternatively, the ratio can be increased by augmenting the level of regulatory T cells in the subject and decreasing the level of pro-inflammatory T cells in the treated subject. When the Treg/pro-inflammatory T cells ratio is increased in the treated subject, it is considered that a state of anergy and/or of increased tolerance is induced or present in the treated subject. The induction of a state of anergy or immunotolerance in individuals experiencing an abnormally elevated immune reaction can be therapeutically beneficial for limiting the symptoms or pathology associated with the abnormally elevated immune reaction. In some embodiments, it is not necessary to induce a state of complete anergy or tolerance, a partial induction of anergy or tolerance can be beneficial to prevent, treat and/or alleviate the symptoms of a disorder associated with a pro-inflammatory state (such as, for example, an autoimmune disease or an excessive immune response).

In order to increase the Treg/pro-inflammatory T cells ratio, the acellular preparation is administered to the treated subject in a therapeutically effective amount. In a first embodiment, the acellular preparation can be prepared using the conditioned blood obtained by administering a first leukocyte to a test subject. In such embodiment, the first leukocyte, allogeneic or xenogeneic to the test subject, can be allogeneic, xenogeneic, autologous or syngeneic to the treated subject. In a second embodiment, the acellular preparation can be prepared using the conditioned medium obtained by co-culturing a first leukocyte with a second leukocyte. In such embodiment, the first leukocyte, allogeneic or xenogeneic to the second leukocyte, can be allogeneic, xenogeneic, autologous or syngeneic to the treated subject. In addition, the second leukocyte, allogeneic or xenogeneic to the first leukocyte, can be allogeneic, xenogeneic, autologous or syngeneic to the treated subject.

As shown herein, the administration of the acellular preparation induces a state of anergy or immune tolerance in the treated subject. In some embodiments, the state of anergy can persist long after the administration of the acellular preparation (as shown below, at least 270 days in mice). In an optional embodiment, the state of anergy does not revert back to a pro-inflammatory state upon a challenge with, for example, an immunogen (such as an immunogenic or allogeneic cell). Consequently, the methods and cellular preparations described herein are useful for the treatment, prevention and/or alleviation of symptoms associated with abnormal/excessive immune responses and conditions associated thereto.

Autoimmunity arises consequent to an animal/individual's immune system recognizing their own tissues as "non-self". Autoimmunity is largely a cell-mediated disease with T lymphocytes playing a central role in "self" recognition and are, in many cases, also the effector cells. The Non-Obese Diabetic (NOD) mouse is an inbred strain that exhibits the spontaneous development of a variety of autoimmune diseases including insulin dependent diabetes. It is considered to be an exemplary mouse model of autoimmunity in general. The murine autoimmune diabetes develops beginning around 10 to 15 weeks of age and has been extensively used to study the mechanisms underlying autoimmune-mediated diabetes, therapeutic interventions and the effect of viral enhancers on disease pathogenesis. Diabetes develops in NOD mice as a result of insulitis, a leukocytic infiltrate of the pancreatic islets. This can be exacerbated if mice are exposed to killed mycobacterium or other agents (Coxsackie virus for example). Multiple studies have established that the pathogenesis of diabetes in the NOD mouse is very similar to that observed in human type I diabetes (T1D) in that it is characterized by the breakdown of multiple tolerance pathways and development of severe insulitis of the islets prior to β-cell destruction. Moreover, T cells (including Th1, Th17 and Tregs) have been identified as key mediators of the autoimmune disease process though other cells (NK cells, B-cells, DC and macrophages) are also observed. Indeed, the NOD mouse model has translated into successful clinical human trials utilizing T-cell targeting therapies for treatment of many autoimmune diseases, including T1D. The loss of function arising from pro-inflammatory allo-recognition is exemplified by the destruction of the islets of Langerhans (insulin secreting β cells) in the pancreas of the NOD mice leading to the onset of Type 1 diabetes. In the context of type I diabetes, pro-tolerogenic allo-recognition is going to confer the protection and survival of the islets of Langerhans and the inhibition of diabetes in the treated subject.

Current treatment of most autoimmune diseases is problematic since it focuses on addressing disease symptoms, not causation. Typically, treatment for chronic autoimmune disease is via systemic steroid (e.g., dexamethasone) administration to induce a general immunosuppression and to act as an anti-inflammatory agent. It is believed that one mechanism of this immunosuppression may be the induction of Treg cells. In addition to steroids, the administration of IVIg (pooled, polyvalent, IgG purified from the plasma of >1 000 blood donors) can also effectively treat some autoimmune diseases including immune thrombocytopenia (ITP). Interestingly, the onset of diabetes in NOD mice can also be delayed, but not fully blocked by administration of IVIg and this may correlate with induction of Tregs (and/or IL-10). Moreover etanercept (trade name ENBREL®), a soluble TNF-receptor, has also been shown to decrease the incidence of diabetes in NOD mice and has been used in small scale human trials. Hence, novel approaches to increase Treg cells (and/or IL-10) while decreasing inflammatory T cell responses (e.g., Th17, NK cells) could be beneficial in treating autoimmune diabetes.

A state of anergy or immune tolerance can be considered therapeutically beneficial in subjects experiencing (or at risk of experiencing) an abnormal immune response, such as for example an auto-immune disease. Individuals afflicted by auto-immune diseases have either low levels of Tregs and/or elevated levels of pro-inflammatory T cells (such as Th17 and/or Th1) when compared to age- and sex-matched healthy individuals. Such auto-immune diseases include, but are not limited to, type I diabetes, rheumatoid arthritis, multiple sclerosis, lupus, immune thrombocytopenia, experimental autoimmune encephalomyelitis, auto-immune uveitis, psoriasis inflammatory bowel disease, scleroderma and Crohn's disease. Because it is shown herein that the acellular preparations are beneficial for increasing the ratio Tregs/pro-inflammatory T cells, it is expected that administration of the acellular preparations to afflicted subjects will alleviate symptoms associated with the auto-immune disease and/or prevent disease severity.

A state of anergy or tolerance can also be considered therapeutically beneficial in subjects at risk of developing an abnormally elevated/excessive immune response. Such abnormally elevated immune response can be observed in subjects receiving a vaccine. For example, it has been shown that subjects receiving a respiratory syncytial virus (RSV) vaccine develop an excessive immune response. Because it is shown herein that the acellular preparations are beneficial for increasing the ratio Tregs/pro-inflammatory T cells, it is expected that administration of the acellular preparations to subject having received or intended to receive a vaccine will alleviate symptoms associated with the administration of the vaccine and/or prevent the development of an excessive immune response. In such embodiment, the acellular preparation can be administered (or formulated for administration) prior to the vaccine, simultaneously with the vaccine or after the administration of the vaccine. When used to prevent or limit excessive immune response to a vaccine, the acellular preparations can be manufactured from a conditioned medium. The conditioned medium can be obtained by co-culturing a first leukocyte, being allogeneic or xenogeneic to a second leukocyte, which can be allogeneic, xenogeneic, autologous or syngeneic to the subject to be vaccinated. The second leukocyte, much like the first leukocyte, can be allogeneic, xenogeneic, autologous or syngeneic to the subject to be vaccinated. When used to prevent or limit an excessive immune response to a vaccine, the acellular preparations can also be manufactured from a conditioned blood. The conditioned blood can be obtained by administered a first leukocyte, being allogeneic or xenogeneic to the test subject, which can be allogeneic, xenogeneic, autologous or syngeneic to the subject to be vaccinated.

Such abnormally elevated immune response can also be observed in subjects having received a transplant (cells or tissues). In these instances, the acellular preparations can be used to prevent or limit the elevated/excessive immune response (e.g. graft destruction or graft rejection). In an embodiment, the acellular preparation can be contacted with the cells/tissue to be transplanted prior to the transplantation (e.g. for example in a transplant medium or a preservation medium). When used to prevent or limit graft destruction or graft rejection, the acellular preparations can be manufactured from a conditioned medium. The conditioned medium can be obtained by co-culturing a first leukocyte, being allogeneic or xenogeneic to a second leukocyte, which can be allogeneic, xenogeneic, autologous or syngeneic to the subject to be treated. Alternatively, the first leukocyte is allogeneic, xenogeneic, autologous or syngeneic to the cells or tissue intended to be grafted. The second leukocyte, much like the first leukocyte, can be allogeneic, xenogeneic, autologous or syngeneic to the subject to be treated. Alternatively, the second leukocyte is allogeneic, xenogeneic, autologous or syngeneic to the cells or tissue intended to be grafted. When used to prevent or limit graft destruction or graft rejection, the acellular preparations can also be manufactured from a conditioned blood. The conditioned blood can be obtained by administering a first leukocyte, being allogeneic or xenogeneic to the test subject, which can be allogeneic, xenogeneic, autologous or syngeneic to the subject to be treated. Alternatively, the first leukocyte is allogeneic, xenogeneic, autologous or syngeneic to the cells or tissue intended to be grafted.

Alternatively or optionally, the acellular preparations can also be used to prevent or limit a graft-vs.-host disease (GVHD) in a subject having received or intended to receive transplanted immune cells or stem cells. In an embodiment, the acellular preparations can be contacted (e.g. cultured) with the cells intended to be grafted prior to transfusion in the subject (e.g. for example in a transplantation medium or preservation medium) to induce a state of anergy or tolerance in those cells. In another embodiment, the acellular preparations can be administered to the subject prior to the transfusion of immune/stem cells to induce a state of anergy or tolerance to prevent or limit GVHD. In still another embodiment, the acellular preparations can be administered simultaneously with the transfused immune/stem cells to prevent or limit GVHD. In yet another embodiment, the acellular preparations can be administered to a subject having been transfused with immune cells or stem cells either to alleviate the symptoms associated to GVHD (when the subject experiences such symptoms) or to prevent GVHD (when the subject is at risk of experiencing such symptoms).

For the treatment of GVHD, the conditioned medium can be obtained by co-culturing two allogeneic/xenogeneic leukocyte population. In an embodiment, the first leukocyte population can be allogeneic, xenogeneic, syngeneic to or derived from the donor (of the immune or stem cells). In another embodiment, the first leukocyte population can be allogeneic, xenogeneic, syngeneic to or derived from the recipient (intended to receive the immune or stem cells). In still another embodiment, the second leukocyte population can be allogeneic, xenogeneic, syngeneic to or derived from the donor. In yet another embodiment, the second leukocyte population can be allogeneic, xenogeneic, syngeneic to or derived from the recipient. For the treatment of GVHD, the conditioned blood can be obtained by administering a first leukocyte allogeneic or xenogeneic to the test subject (e.g. and in an embodiment to the donor). In an embodiment, the first leukocyte population can be allogeneic, xenogeneic, syngeneic to or derived from the donor. In another embodiment, the first leukocyte population can be allogeneic, xenogeneic, syngeneic to or derived from the recipient.

The acellular preparation the acellular preparation can be administered (or formulated for administration) prior to the transplant, simultaneously with the transplant or after the transplant.

In the methods and acellular preparations described herein, it is contemplated that the acellular-based preparations be optionally administered with other therapeutic agents known to be useful for the treatment, prevention and/or alleviation of symptoms of conditions associated to an excessive/abnormal immune response, such as, for example, cortisone, IL-10, IL-11 and/or IL-12.

The present invention will be more readily understood by referring to the following examples which are given to illustrate the invention rather than to limit its scope.

Example I—Material and Methods

Human PBMC and Dendritic Cell Preparation.

Human whole blood was collected in heparinized vacutainer blood collection tubes (BD, Franklin Lakes, N.J.) from healthy volunteer donors following informed consent. PBMC were isolated from diluted whole blood using FicollePaque PREMIUM™ (GE Healthcare Bio-Sciences Corp, Piscataway, N.J.) as per the product instructions. The PBMC layer was washed twice with 1× Hank's Balanced Salt Solution (HBSS; without $CaCl_2$ and $MgSO_4$; Invitrogen by Life Technologies, Carlsbad, Calif.) and resuspended in the appropriate media as needed for mixed lymphocyte reactions and flow cytometric analysis of Treg and Th17 phenotypes. Dendritic cells (DC) were prepared from isolated PBMC as described by O'Neill and Bhardwaj (O'Neill et al., 2005). Briefly, freshly isolated PBMC were overlaid on Petri dishes for 3 h in AIM V serum free culture medium (Invitrogen, Carlsbad, Calif.). Non-adherent cells were gently washed off the plate. The adherent cells (monocyte rich cells) were treated with IL-4 and GM-CSF (50 and 100 ng/mL respectively; R&D Systems, Minneapolis, Minn.) in AIM V medium. Cells were again treated with IL-4 and GM-CSF on days 2 and 5. On day 6, cells were centrifuged and resuspended in fresh media supplemented with DC maturation factors (TNF-α, IL-1β, IL-6; R&D Systems, Minneapolis, Minn.) and prostaglandin E2 (Sigma Aldrich, St. Louis, Mo.). The mature DC-like cells were harvested on day 7 and CD80, CD83, CD86 and HLA-DR expressions were determined to confirm DC maturation via flow cytometry (FACSCalibur™ Flow Cytometer, BD Biosciences, San Jose, Calif.).

Murine Splenocyte and Tissue Harvesting.

All murine studies were done in accordance with the Canadian Council of Animal Care and the University of British Columbia Animal Care Committee guidelines and were conducted within the Centre for Disease Modeling at the University of British Columbia. Murine donor cells used for the in vivo donation and in vitro studies were euthanized by $CO_2$. Three allogeneic strains of mice were utilized for syngeneic and allogeneic in vitro and in vivo challenge: Balb/c, H-$2^d$; C57Bl/6, H-$2^b$; and C3H, H-$2^k$. Murine spleens, brachial lymph nodes, and peripheral blood were collected at the indicated days. Mouse spleens and brachial lymph nodes were dissected and placed into cold phosphate buffered saline (PBS; 1.9 mM $NaH_2PO_4$, 8.1 mM $Na_2HPO_4$, and 154 mM NaCl, pH 7.3) containing 0.2% bovine serum albumin (BSA; Sigma Aldrich, St. Louis, Mo.) and kept on ice until ready to process. Whole blood was collected in heparinized tubes via cardiac puncture. Murine donor splenocytes were prepared from freshly harvested syngeneic or allogeneic spleens via homogenization into a cell suspension in PBS (0.2% BSA) using the frosted end of two microscope slides. The resultant cell suspension was spun down at 500×g. The splenocyte pellet was resuspended in 1 mL of 1×BD Pharm LYSE™ lysing buffer (BD Biosciences, San Diego, Calif.) and incubated for 1 min at room temperature. Lymph node cells were harvested via tissue homogenization as described above, washed twice and resuspended in PBS (0.2% BSA) for flow cytometric analysis of Th17, Treg and murine haplotype. Recipient peripheral blood lymphocytes were prepared via lysis of the red cells (BD Pharm Lyse lysing buffer; BD Biosciences, San Diego, Calif.) at 1× concentration, followed by washing (1×) and resuspension in PBS (0.2% BSA) for flow analysis of Th17, Treg and murine haplotype.

mPEG Modification (PEGylation) of PBMCs and Splenocytes.

Human PBMC and murine splenocytes were derivatized using methoxypoly(-ethylene glycol) succinimidyl valerate (mPEG-SVA; Laysan Bio Inc. Arab, Ala.) with a molecular weight of 20 kDa as previously described (Scott et al., 1997; Murad et al, 1999A; Chen et al., 2003; Chen et al., 2006, Wang et al., 2011). Grafting concentrations was 1 mM per 4×$10^6$ cells/mL. Cells were incubated with the activated mPEG for 60 min at room temperature in isotonic alkaline phosphate buffer (50 mM $K_2HPO_4$ and 105 mM NaCl; pH 8.0), then washed twice with 25 mM HEPES/RPMI 1640 containing 0.01% human albumin. Murine splenocytes used for in vivo studies were resuspended in sterile saline at a final cell density of 2.0×$10^8$ cells/ml for intravenous (i.v.) injection.

In Vitro and In Vivo Cell Proliferation.

Cell proliferation (both in vitro and in vivo) was assessed via flow cytometry using the CELLTRACE™ CFSE (Carboxyfluorescein diacetate, succinimidyl ester) Cell Proliferation Kit (Invitrogen by Life Technologies e Molecular probes, Carlsbad, Calif.). Human and murine cells labeling was done according to the product insert at a final concentration of 2.5 mM CFSE per 2×$10^6$ cells total. Donor and recipient cell proliferation was differentially determined by haplotype analysis. In some experiments, cell proliferation was measured by $^3$H-thymidine incorporation. In these experiments, donor splenocytes (5.12×$10^6$ cells per well) were co-incubated in triplicate in 96-well plates at 37° C., 5% $CO_2$ for 3 days. On day 3, all wells were pulsed with $^3$H-thymidine and incubated for 24 h at 37° C., 5% $CO_2$. Cellular DNA was collected on filter mats using a Skatron cell harvester (Suffolk, U.K.) and cellular proliferation was measured by $^3$H-thymidine incorporation.

Mixed Lymphocyte Reaction (MLR)—Control and Conditioned Medium.

The immunodulatory effects of the various preparations were assayed using a MLR (Murad et al, 1999A; Chen et al., 2003; Chen et al., 2006; Wang et al., 2011). For the human MLRs, PBMC from two MHC-disparate human donors were labeled with CFSE. For mice MLR, splenocytes from two H-2-disparate mice (Balb/c and C57Bl/6) were labeled with CFSE. Each MLR reaction well contained a total of 1×$10^6$ cells (single donor for resting or mitogen stimulation or equal numbers for disparate donors for MLR). Cells were plated in multiwell flat-bottom 24-well tissue culture plates (BD Biosciences, Discovery Labware, Bedford, Mass.). PBMC proliferation, cytokine secretion, as well as Treg and Th17 phenotyping was done. For flow cytometric analysis, the harvested cells were resuspended in PBS (0.1% BSA).

Immunophenotyping by Flow Cytometry.

The T lymphocytes populations (double positive for CD3$^+$ and CD4$^+$) were measured by flow cytometry using fluorescently labeled anti-CD3 and anti-CD4 (BD Pharmingen, San Diego, Calif.), anti-IL-2, anti-IL-4, anti-IL-10, anti-IL-12, anti-IL-17, anti-FoxP3, anti-NK1.1, anti-IFN-γ, anti-TNF-α, anti-CD152, anti CD62L and anti-CD11c monoclonal antibodies. Human and mouse Regulatory T lymphocytes (Treg) were CD3+/CD4+ and FoxP3+ (transcription factor) while inflammatory Th17 lymphocytes cells were CD3+/CD4+ and IL-17+ (cytokine) as measured per the BD Treg/Th17 Phenotyping Kit (BD Pharmingen, San Diego, Calif.). After the staining, the cells ($1\times10^6$ cells total) were washed and resuspended in PBS (0.1% BSA) prior to flow acquisition. Isotype controls were also used to determine background fluorescence. All samples were acquired using the FACSCalibur™ flow cytometer (BD Biosciences, San Jose, Calif.) and CellQuest Pro™ software for both acquisition and analysis.

In Vivo Murine Studies.

The following strains were used Balb/c, $H-2^d$; C57Bl/6, $H-2^b$; and C3H, $H-2^k$ (Chen et al., 2003; Chen et al., 2006) as well a NOD (Anderson et al., 2005). All mice (donors and recipients) were 9-11 weeks old. Donor splenocytes were prepared were transfused intravenously (i.v.) via the tail vein into recipient animals. BALB/c and C57BL/6 mice injected with sterile saline served as control animals. Animals were euthanized by $CO_2$ at predetermined intervals at which time blood, brachial lymph nodes and spleen were collected and processed for Th17/Treg phenotyping analysis and splenocyte proliferation studies by flow cytometry.

Conditioned Plasma.

Mouse were either untreated (naïve) or treated with saline, non-polymer modified allogeneic splenocytes or PEGylated allogeneic splenocytes (obtained by the procedures explained above). After five days, a cell-free conditioned plasma was obtained (from mouse blood using the mirVana™ PARIS™ kit from Ambion by Life Technologies) and transfused to another naïve mouse.

Plasma Fractionation.

The plasma fractionation was performed using centrifugal filter molecular cutoff devices. Millipore's Amicon® Ultra-0.5 centrifugal filter devices were used (Amicon Ultra 3k, 10K, 30K, 50K, and 100K devices).

miRNA Extraction.

The miRNA was extracted from samples (conditioned medium or plasma) using mirVana™ PARIS™ kit from Ambion® by Life Technologies according to the manufacturer's instructions. Briefly, the sample is mixed with the 2× denaturing solution provided and subjected to acid-phenol:chloroform extraction. To isolate RNA that is highly enriched for small RNA species, 100% ethanol was added to bring the samples to 25% ethanol. When this lysate/ethanol mixture was passed through a glass-fiber filter, large RNAs are immobilized, and the small RNA species are collected in the filtrate. The ethanol concentration of the filtrate was then increased to 55%, and it was passed through a second glass-fiber filter where the small RNAs become immobilized. This RNA is washed a few times, and eluted in a low ionic strength solution. Using this approach, an RNA fraction highly enriched in RNA species <200 nt can be obtained. Note that the large RNA species (>200 nt) can be recovered from the first filter if necessary.

TA Preparations.

The murine miRNA preparations (e.g. TA1 preparations) used were extracted from the conditioned plasma obtained 5 days after mice have received mPEG allogeneic splenocytes. Extraction can occur at time points other than 5 days (e.g., 24 hours post administration) and yield similar results (data not shown). Five days was chosen as Treg levels achieved maximal levels at this point in the mice. The human miRNA preparations (e.g. TA2 preparations) used were extracted from the conditioned medium of an mPEG-MLR harvested 72 hours following the initiation of the mPEG-MLR. However, miRNA harvested from human PBMC mPEG-MLR at 24 hours also yields the desired immunomodulatory effects (data not shown). To calibrate, miRNA concentration can be quantitated via a Qubit® 2.0 Fluorometer (LifeTechnologies) and selected fluorescent dyes which emit a signal only when bound to specific target (i.e., miRNA) molecules.

miRNA Characterization.

The miRNA of the conditioned medium were characterized by qPCR using the miScript miRNA™ PCR Array Human Immunopathology (Qiagen) for human conditioned medium and the Mouse Immunopathology miRNA PCR Array™ (Qiagen) for mouse conditioned plasma/media.

RNase Treatment.

Murine plasma was pooled and for each individual mouse. For each 500 µL of murine plasma (or the <10 kDa plasma fraction), 50 ng RNase (RNase A, 20 mg/mL stock, Life Technologies (In Vitrogen)) was added. Then samples were incubated for 10 minutes at 37° C. to degrade the nucleic acids. The control plasma (or <10 kDa fraction) without RNAase A treatment was incubated at 37° C. for 10 min. The RNase treated plasma (100 µl per mouse) was injected (i.v.) into mice (n=5). RNase A alone (10 ng/mouse) was used for the control mice to insure that the RNase A was not toxic and this trace amount of RNase did not have an in vivo immunomodulatory effects.

Phosphorylation of Phosphokinases.

Analyzing the phosphorylation state of kinases and their protein substrates allows for the characterization of the effects of conditioned plasma or media on how cells respond to allogeneic stimuli. The human phospho-kinase array (R&D Systems Inc) is a rapid, sensitive tool to simultaneously detect the relative levels of phosphorylation of 43 kinase phosphorylation sites and 2 related total proteins. Each capture antibody was carefully selected using cell lysates prepared from cell lines known to express the target protein. Capture and control antibodies are spotted in duplicate on nitrocellulose membranes. Cell lysates are diluted and incubated overnight with the human phospho-kinase array. The array is washed to remove unbound proteins followed by incubation with a cocktail of biotinylated detection antibodies. Streptavidin-HRP and chemiluminescent detection reagents are applied and a signal is produced at each capture spot corresponding to the amount of phosphorylated protein bound.

Statistical Analysis.

Data analysis for flow analysis was conducted using SPSS™ (v12) statistical software (Statistical Products and Services Solutions, Chicago, Ill., USA). For significance, a minimum p value of <0.05 was used. For comparison of three or more means, a one-way analysis of variance (ANOVA) was performed. When significant differences were found, a post-hoc Tukey test was used for pair-wise comparison of means. When only two means were compared, student-t tests were performed.

Example II—In Vitro and In Vivo Immunomodulation of Size-Fractionated Acellular Preparations Two-way human PBMC MLRs were prepared using the conditioned medium collected at 72 hours from mPEG MLR as the primary MLR. The conditioned medium was fractionated with respect to its molecular weight (higher or lower than 10 kDa). As shown on FIG. 1, the fraction of the conditioned medium derived from PEGylated MLR and having a molecular weight of less than 10 kDa retained the ability to increase human Treg levels in vitro. As also shown in FIG. 1, the fraction having a molecular weight higher than 10 kDa did not have the ability to increase Treg levels in vitro in the secondary MLR.

A conditioned cell-free plasma from untreated mouse (naïve), mouse having received saline (saline), allogeneic unmodified splenocytes (allogeneic) and PEGylated allogeneic splenocytes (mPEG-allogeneic) were obtained 5 days after treatment. The conditioned plasma was either left untreated (e.g. complete) or fractionated in function of the size of its components (>100 kDa, between 30 and 100 kDa, between 10 and 30 kDa or <10 kDa). The conditioned plasma was then transfused to naïve mouse.

Figure 2A:
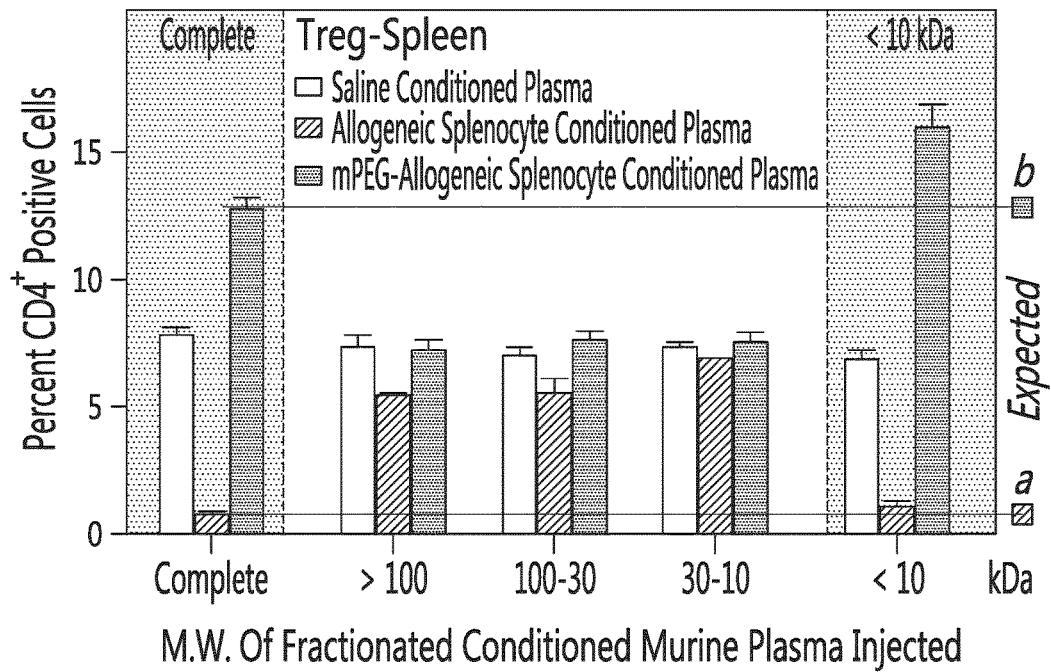
FIG. 2 illustrates the effects of size (MW) separation and RNase treatment on the immunomodulary effects of acellular preparations. Unmodified conditioned murine plasma (obtained from donor mice 5 days post splenocyte transfer), size fractionated-conditioned murine plasma or RNase-treated conditioned murine plasma was administered once to naïve mice and Treg/Th17 levels were measured (when) in the spleen. (A) Results are shown as the percentage of Treg cells (in function of $CD4^+$ cells) in function of type of conditioned medium (white bars=conditioned plasma obtained from administering saline, hatched bars=conditioned plasma obtained from administering unmodified allogeneic splenocytes, grey bars=conditioned plasma obtained from administering polymer modified allogeneic splenocytes) and size fractionation (non-fractioned or complete conditioned serum, fraction>100 kDa, fraction between 30 and 100 kDa, fraction between 10 and 30 kDa, fraction<10 kDa). a denotes the mean value for unfractionated conditioned medium prepared from mice previously treated with unmodified allogeneic cells. b denotes the mean value for unfractionated conditioned medium prepared from mice previously treated with mPEG-modified allogeneic cells. (B) Results are shown as the percentage of Th17 cells (in function of $CD4^+$ cells) in function of type of conditioned medium (white bars=conditioned plasma obtained from administering saline, hatched bars=conditioned plasma obtained from administering unmodified allogeneic splenocytes, grey bars=conditioned plasma obtained from administering polymer modified allogeneic splenocytes) and size fractionation (non-fractioned or complete conditioned serum, fraction>100 kDa, fraction between 30 and 100 kDa, fraction between 10 and 30 kDa, fraction<10 kDa). a denotes the mean value for unfractionated conditioned medium prepared from mice previously treated with unmodified allogeneic cells. b denotes the mean value for unfractionated conditioned medium prepared from mice previously treated with mPEG-modified allogeneic cells. (C) Results are shown as the percentage of Treg cells (in function of $CD4^+$ cells, left panel) or Th17 cells (in function of $CD4^+$ cells, right panel) in function of type of treatment (white bars=N=naïve untreated animals; grey bars=AC=unmodified allogeneic cells; diagonal hatch bars=conditioned plasma obtained from administered unmodified splenocytes treated (allo-plasma (+)) or not (allo-plasma (−)) with RNase; horizontal hatch bars=conditioned plasma obtained from administering polymer modified splenocytes treated (mPEG-allo-plasma (+)) or not (mPEG-allo-plasma (−)) with RNase).
Figure 2B:
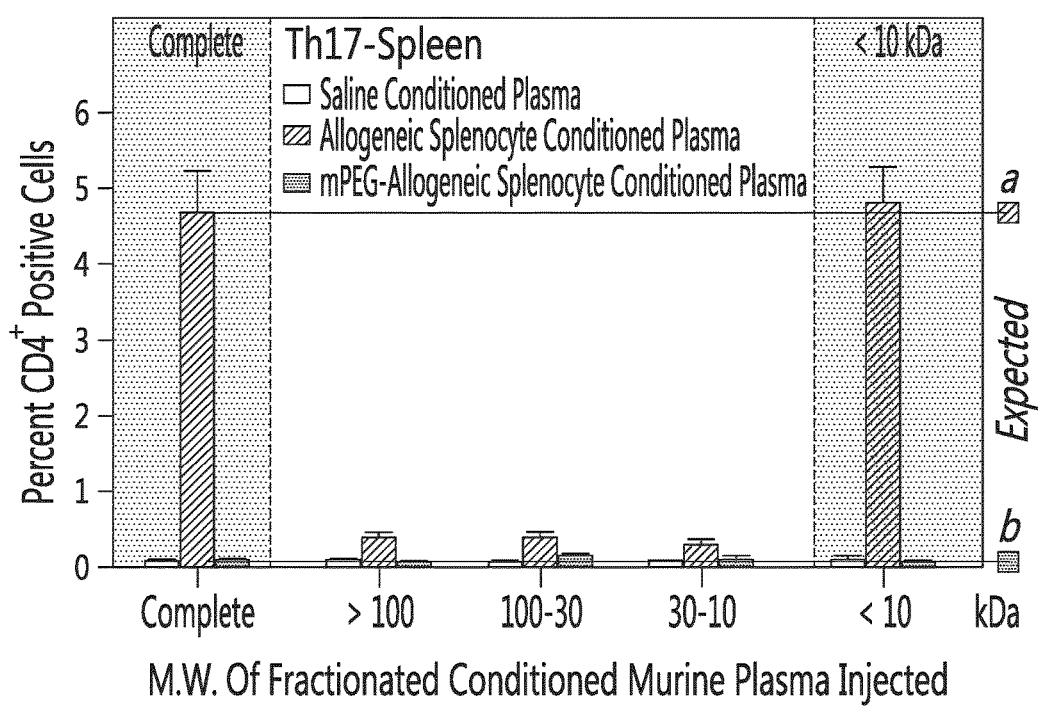

As shown on FIG. 2A, the <10 kDa fraction of the conditioned plasma from mouse having received mPEG allogeneic splenotytes retained the ability to increase Treg levels in vivo. As shown on FIG. 2B, the <10 kDa fraction of the conditioned plasma from mouse having received mPEG allogeneic splenotytes retained the ability to decrease Th17 levels in vivo. The immunodulatory effect of conditioned murine plasma seems to mostly reside in the lower molecular weight fraction (<10 kDa). This low molecular weight fraction does not include the majority of cytokines (usually encompasses in the 100-30 and the 30-10 kDa fractions) typically thought to mediate immunodulation of Tregs and pro-inflammatory leukocytes. However, the <10 kDa fraction is suspected to contain, among its components, microRNAs (miRNAs).

To determine if the miRNAs in the conditioned plasma mediated the immunomodulatory effects observed with the conditioned plasma, mice were injected with control conditioned plasma or the same plasma that had been pre-treated with RNase A, an enzyme that degrades/destroys ribonucleic acids such as miRNAs. As noted in FIG. 2C, treatment with RNase A abolishes virtually all immunomodulatory activity of the conditioned medium, thereby confirming the ribonucleic acid nature of the size-fractionated conditioned plasma.

Figure 3A:
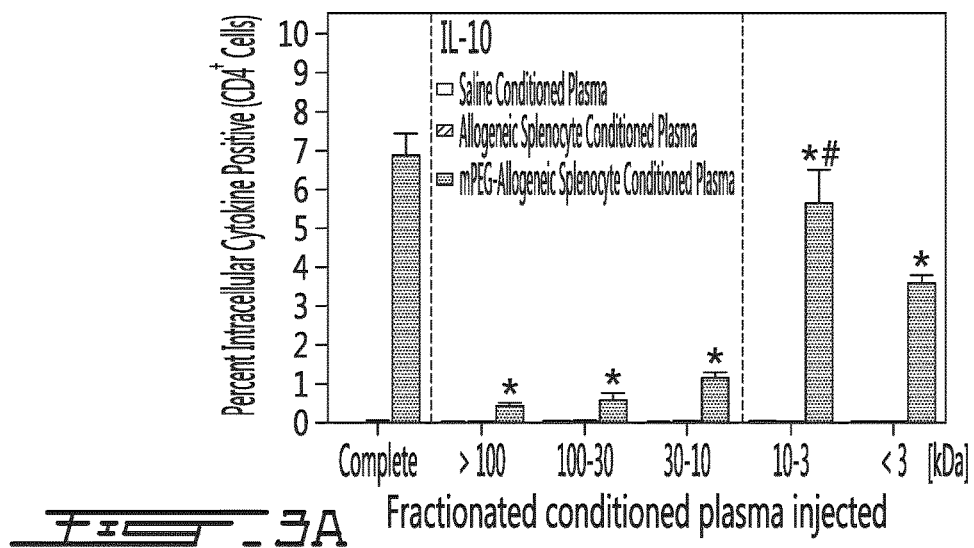
FIG. 3 illustrates the size fractionated conditioned plasma on the intracellular expression of cytokines. Unmodified conditioned murine plasma (obtained from donor mice 5 days post saline or splenocyte transfer), size fractionated-conditioned murine plasma was administered once to naïve mice and Treg/Th17 levels were measured (when) in the spleen. Results are shown as the percentage intracellular cytokine positive $CD4^+$ cells in function of type of conditioned medium (white bars=conditioned plasma obtained from administering saline, hatched bars=conditioned plasma obtained from administering unmodified allogeneic splenocytes, grey bars=conditioned plasma obtained from administering polymer modified allogeneic splenocytes) and size fractionation (non-fractioned or complete conditioned serum, fraction>100 kDa, fraction between 30 and 100 kDa, fraction between 10 and 30 kDa, fraction<10 kDa) for (A) IL-10, (B) IL-2, (C) IFN-γ, (D) TNF-α and (E) IL-4. * denotes p<0.001 relative to treatment with conditioned plasma from mice treated with saline, # denotes p<0.001 relative to treatment with conditioned medium derived from mice treated with unmodified allogeneic splenocytes.
Figure 3B:
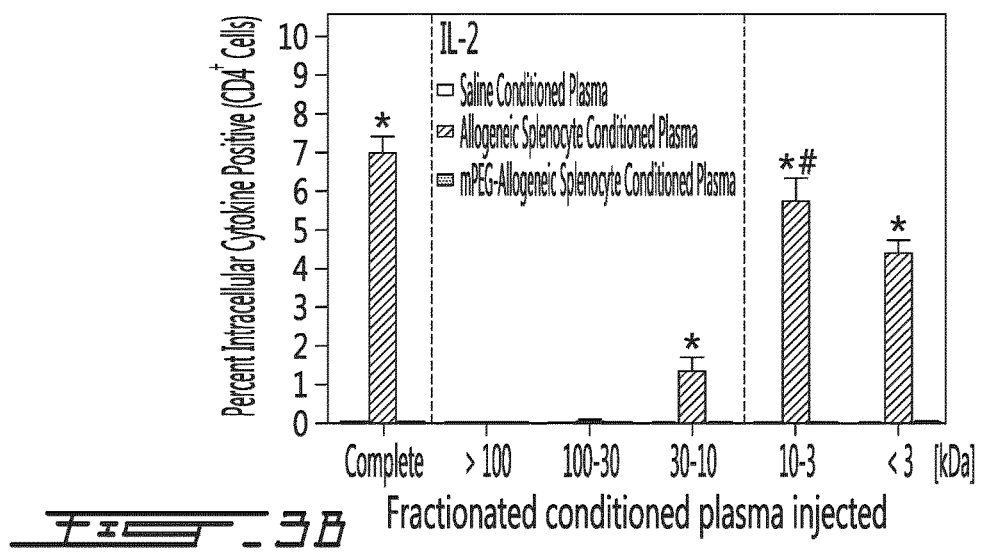
Figure 3C:
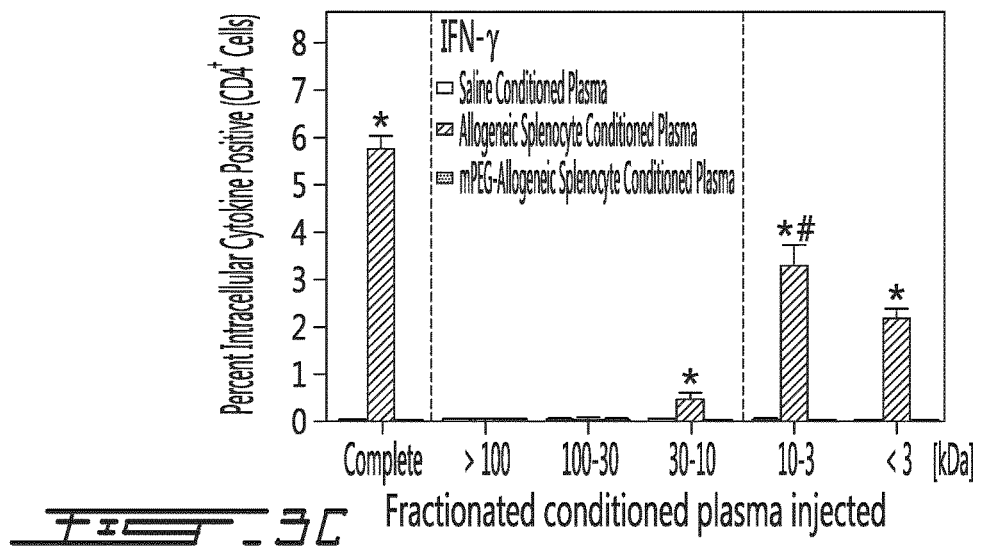
Figure 3D:
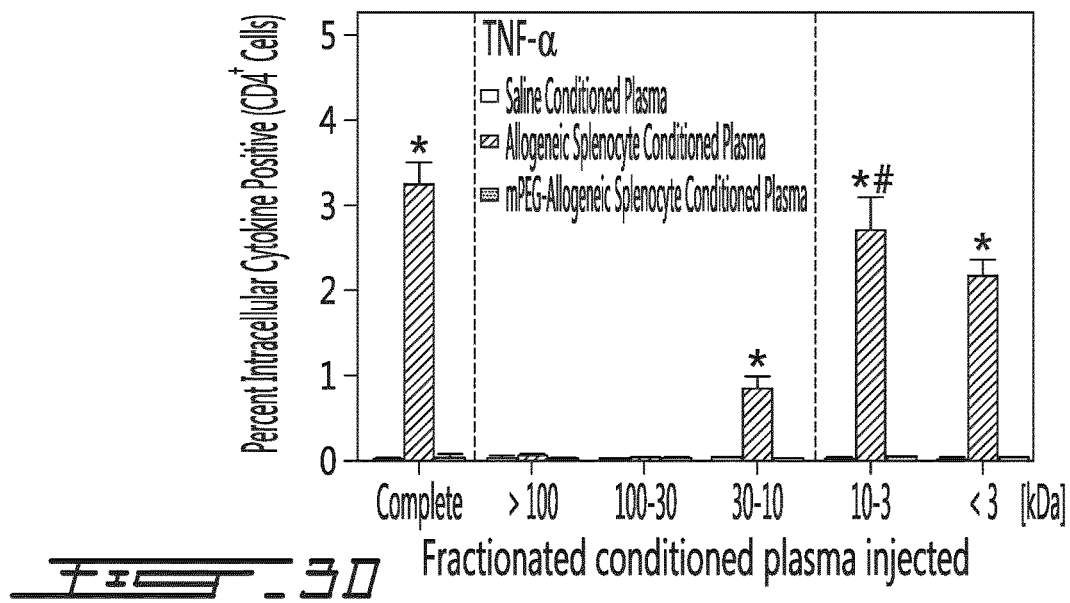
Figure 3E:
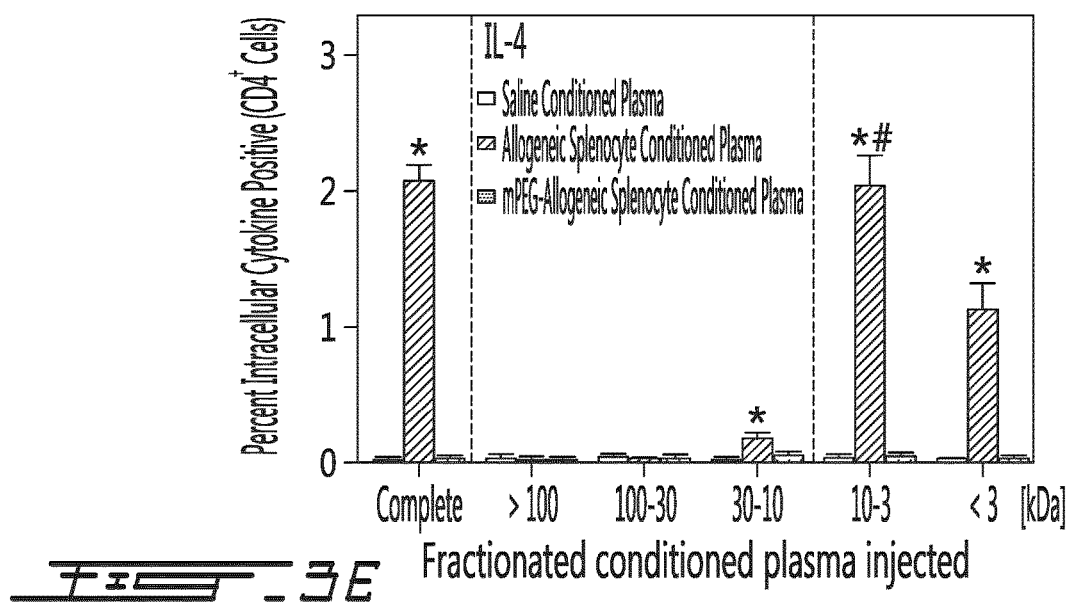

The size-fractionation conditioned plasma was administered to mice and its effects on the intracellular cytokine expression of $CD4^+$ cells was examined. As shown on FIG. 3, the <10 kDa fraction and some of the <3 kDa fraction of the conditioned plasma from mouse having received mPEG allogeneic splenotytes increase IL-10 intracellular expression in $CD4^+$ cells in vivo (FIG. 3A). However, the <10 kDa fraction and the <3 kDa fraction of the conditioned plasma from mouse having received mPEG allogeneic splenotytes did not exhibit any increase in IL-2, TNF-α, IFN-γ or IL-4 intracellular expression in $CD4^+$ cells in vivo (FIGS. 3B to 3E). The <10 kDa (and some of the >3 kDa) fraction of the conditioned of the mPEG-allogeneic plasma, when compared to the corresponding fractions of the conditioned allogeneic plasma, increased the expression of pro-tolerogenic cytokines, such as IL-10, while actively preventing the expression of pro-inflammatory cytokines, such as IL-2, TNF-α, IFN-γ or IL-4. Indeed, pro-inflammatory cytokines in the mPEG allogeneic plasma recipients remained at levels seen in naïve animals.

Figure 4C:
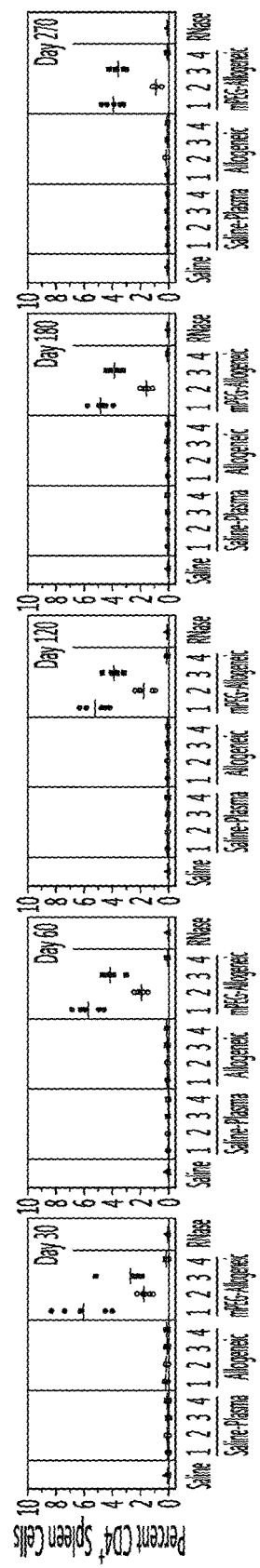
FIG. 4 illustrates the in vivo effects of the various conditioned medium and preparations derived therefrom on the intracellular expression of cytokines as well as type of CD4$^+$ cells. Conditioned plasma was obtained by administering naïve mice with saline, unmmodified allogeneic splenocytes or polymer-modified allogeneic splenocytes (PEG) and recuperating plasma after 5 days. The obtained plasma was either administered directly (●=untreated) or optionally treated with RNaseA (○=conditioned plasma, ■=miRNA enriched fraction of conditioned plasma) and/or further purified so as to retain and enrich the <10 kDa fraction (e.g. miRNA) (■=untreated miRNA, □=RNase A-treated miRNA) prior to administration. As a control, RNase A was also administered directly to some animals. After 30, 60, 120, 180, 270 days, animals were sacrificed, their spleen was removed and CD4$^+$ cells were characterized by flow cytometry. Results are shown for intracellular cytokine expression: IL-2 (A), INF-γ (B), IL-10 (C), as well as CD4$^+$ cell type: Treg (Foxp3$^+$) (D) and Th17 (IL-17$^+$) (E) CD4$^+$ cells.

Example III—In Vitro and In Vivo Immune Modulation by miRNA-Enriched Acellular Preparations The conditioned plasma or the miRNA preparation (100 µL) obtained from the conditioned plasma (of mice having received saline, unmodified allogeneic splenocytes or polymer-modified allogeneic splenocytes) were administered intravenously to 7-8 week-old mice thrice (at days 0, 2 and 4). Cohorts (n=4) of mice were sacrificed at days 30, 60, 120, 180 and 270. Spleens were removed and $CD4^+$ cells were stained for intracellular expression of IL-2, IL-4, IL-10, INF-γ and TNF-α. Splenic Treg and Th17 populations were also measured. As shown on FIGS. 4A-C, the administration of the conditioned plasma or the derived miRNA preparation from mouse having received unmodified allogeneic splenocytes caused an increase in the expression of intracellular IL-2 and INF-γ in $CD4^+$ cells. On the other hand, the administration of the conditioned plasma or the derived miRNA preparation from mouse having received mPEG-modified allogeneic splenocytes (i.e., TA1 preparation) caused an increase in the expression of intracellular IL-10 in $CD4^+$ cells. These modulations in expression were observed until at least 270 days after the administration of the conditioned medium or the miRNA preparation. This data suggests that miRNA was an active component mediating the immunological changes, RNase treatment of the conditioned plasma or of the miRNA preparation prior to administration to animals either diminished (plasma) or abolished (miRNA) the immunomodulatory effects. While conditioned plasma retained some immunomodulatory effect, it is believed that it was due to residual cytokines and/or plasma-mediated inactivation of the RNAase A enzyme.

Figure 4D:
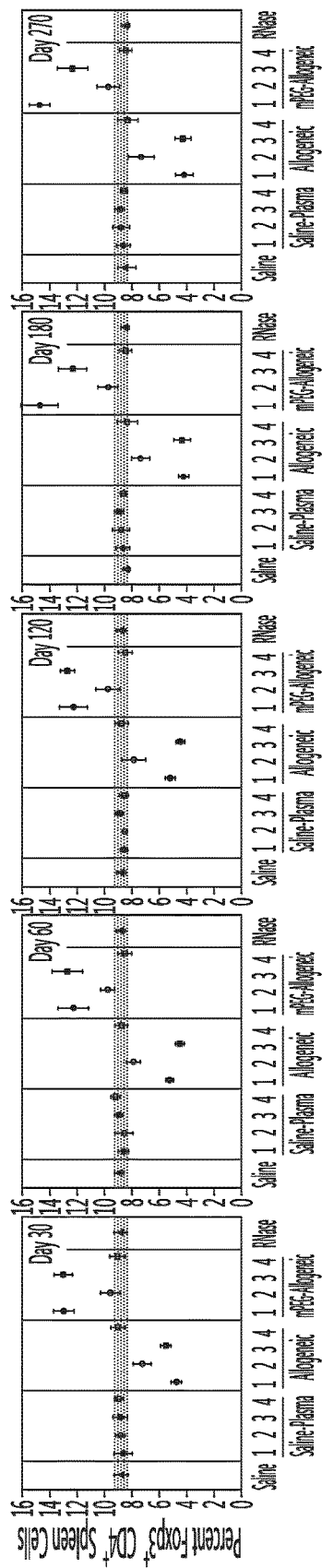
Figure 4E:
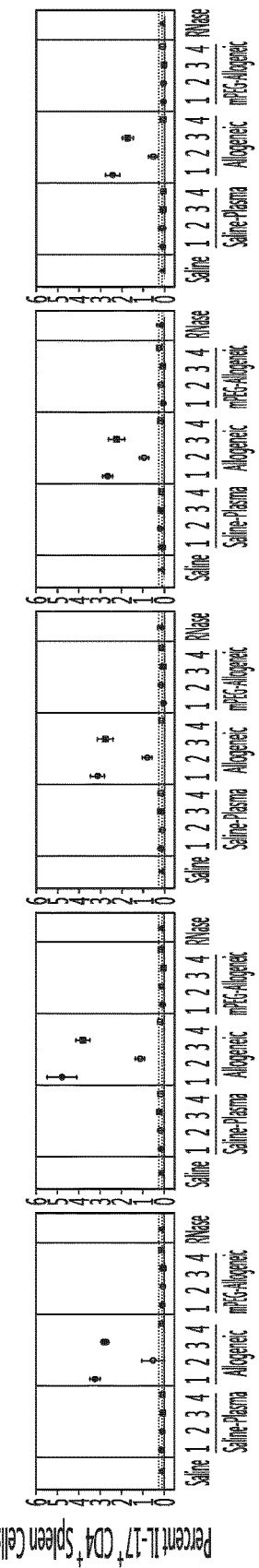

As also shown on FIG. 4D, the administration of the conditioned plasma or the derived miRNA preparation from mouse having received mPEG-modified allogeneic splenocytes (i.e., TA1 preparation) caused an increase in the percentage of Treg ($Foxp3^+$) cells in function of the total $CD4^+$ cells. On the other hand, the administration of the conditioned plasma or the derived miRNA preparation from mouse having received unmodified allogeneic splenocytes caused an increase in the percentage of Th17 ($IL-17^+$) cells in function of the total $CD4^+$ cells (FIG. 4E). These modulations in $CD4^+$ cells types were observed at least 270 days after the administration of the conditioned medium or the miRNA preparations and were diminished (plasma) or abolished (miRNA) with a preliminary RNase treatment. Acellular preparations prepared from mice injected with either allogeneic or mPEG-allogeneic leukocytes exerted potent and long-lasting effects in naive recipient mice. In aggregate, allogeneic-derived preparations (plasma or miRNA) yielded a pro-inflammatory state while mPEG-allogeneic-derived preparations (plasma or miRNA) yielded a immunoquiescent state.

Figure 5A:
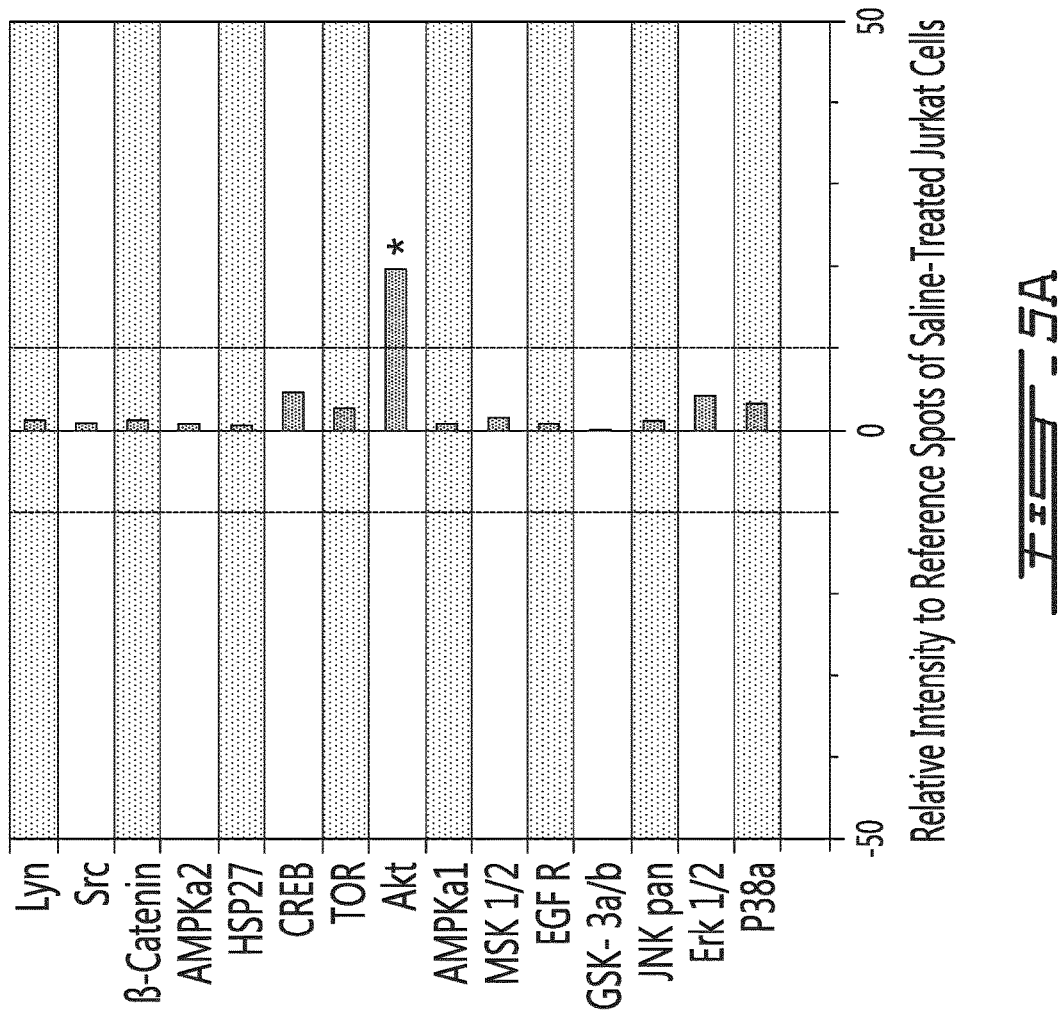
FIG. 5 illustrates the effects of the TA1 preparations on the phosphorylation of phosphokinases of resting Jurkat cells. Results are shown as fold modulation (when compared to saline-treated Jurkat cells) for each kinase tested. (A) On this panel, Akt is considered to be significantly increasingly phosphorylated. (B) On this panel, PRAS40 is considered to be significantly increasingly phosphorylated. (C) On this panel, HSP60 is considered to be significantly decreasingly phosphorylated. * denotes greater than 10-fold increase in protein phosphorylation over resting Jurkat cells. # denotes greater than 10-fold decrease in protein phosphorylation over resting Jurkat cells.
Figure 5B:
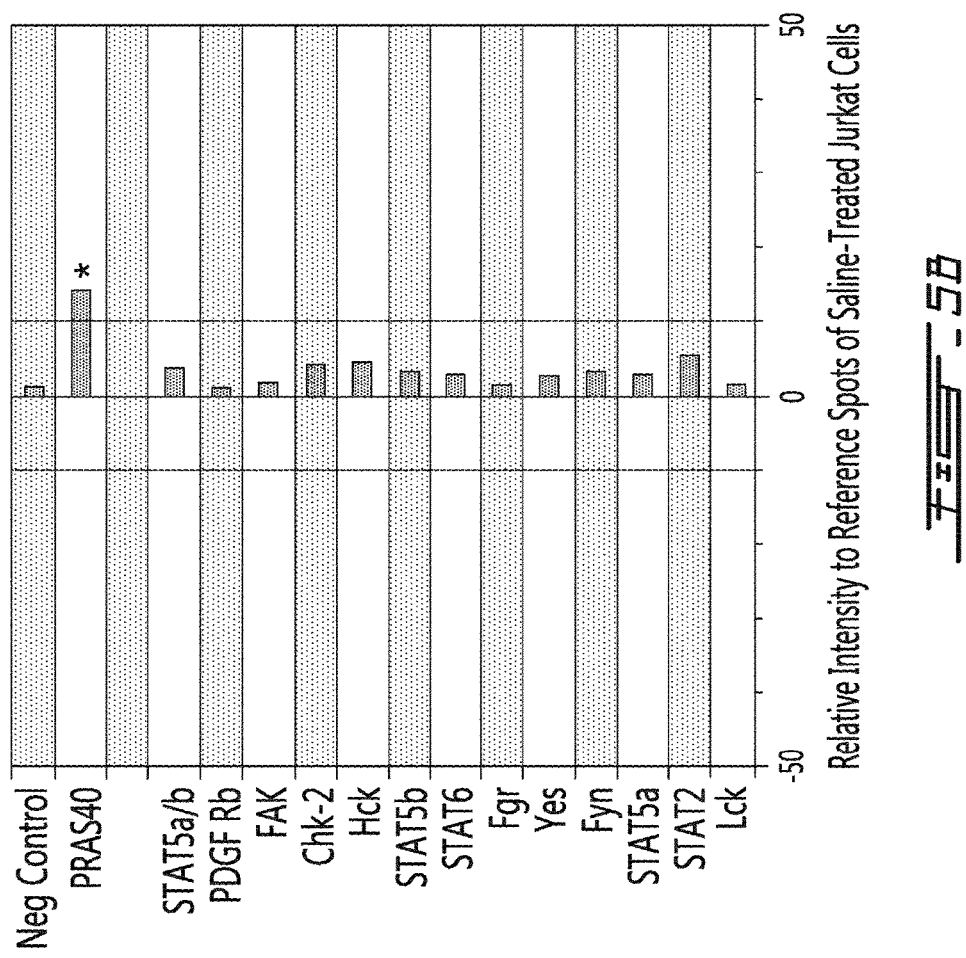

Murine and human-derived miRNA preparations exert a direct effect on cell signaling. Murine TA1 preparations have been incubated with Jurkat cells ($1 \times 10^6$ cells/ml treated with 50 µl of TA1/ml) and the level of phosphorylation of some of the phosphokinase has been measured after 30 minutes of incubation. As shown on FIG. 5, TA1 preparations favored the phosphorylation of Akt and PRAS40 kinases while decreasing the phosphorylation of the HSP60 kinase.

Figure 6A:
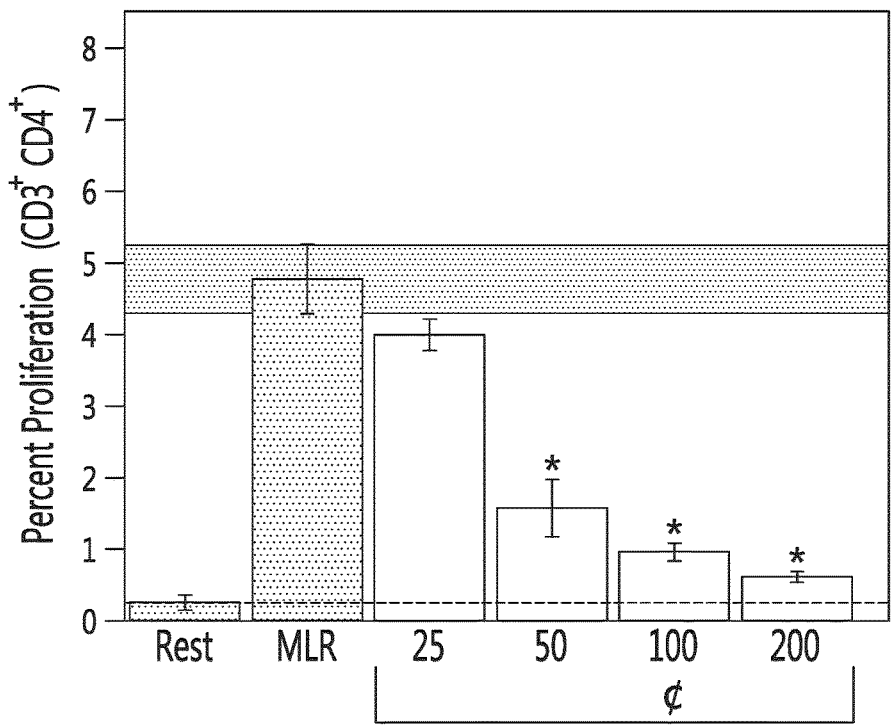
FIG. 6 shows the in vitro effects of the murine TA1 preparation on human PBMC PBMCs. Murine TA1 preparation (either 25 μL, 50 μL, 100 μL or 200 μL) was included in a human PBMC MLR assay and cellular proliferation was measured. Results are shown as percent in proliferation (CD3$^+$CD4$^+$ cells) in function of conditions (Rest=resting MLR, MLR=conventional MLR without TA1, Murine TA-1=MLR with TA1) and TA1 concentration (in μL) after 10 days (A) or 14 days (B). * denotes p<0.001 relative to MLR value and ¢ denotes the concentration of the TA1 preparation used in the in vivo mouse study.
Figure 6B:
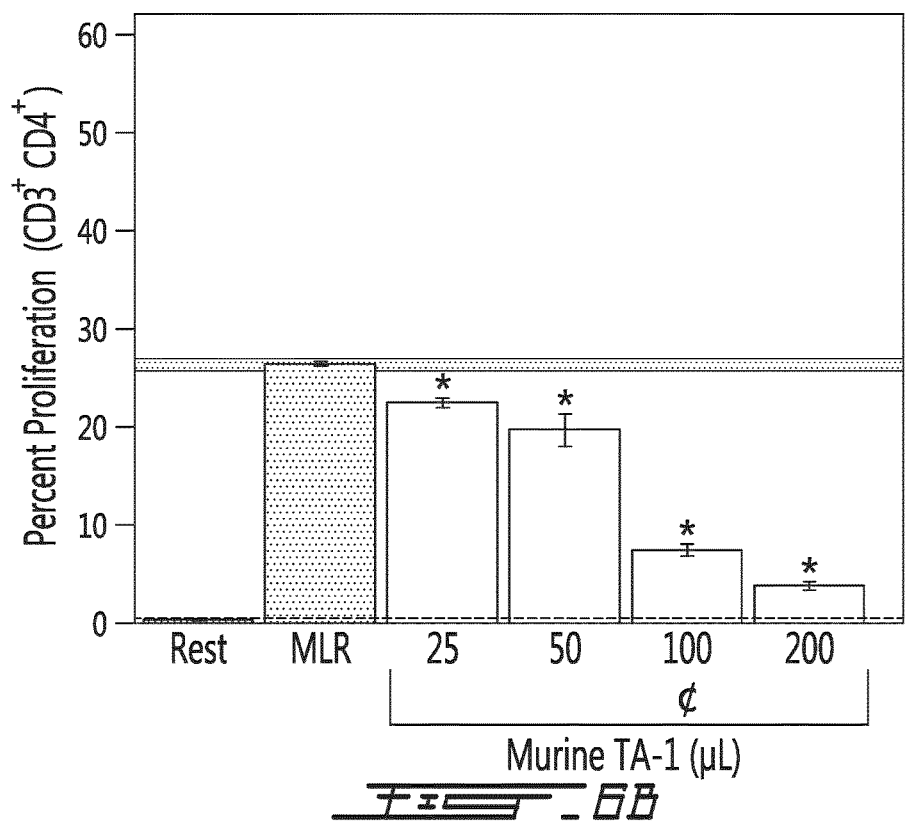

Murine TA1 preparations were also introduced (at time 0) into a human PBMC MLR assay in order to determine their effect on human allo-recognition. As indicated on FIG. 6, the presence of the murine TA1 preparations resulted in a dose-dependent decrease in the percentage in leukocyte proliferation (at both 10 and 14 days) which is indicative of their pro-tolerogenic effects. This data also indicates that the TA1 preparations show significant evolutionary conservations (both sequence specific and similarity) since the murine TA1 are highly effective in a xenogeneic system (e.g. human MLR).

Figure 7A:
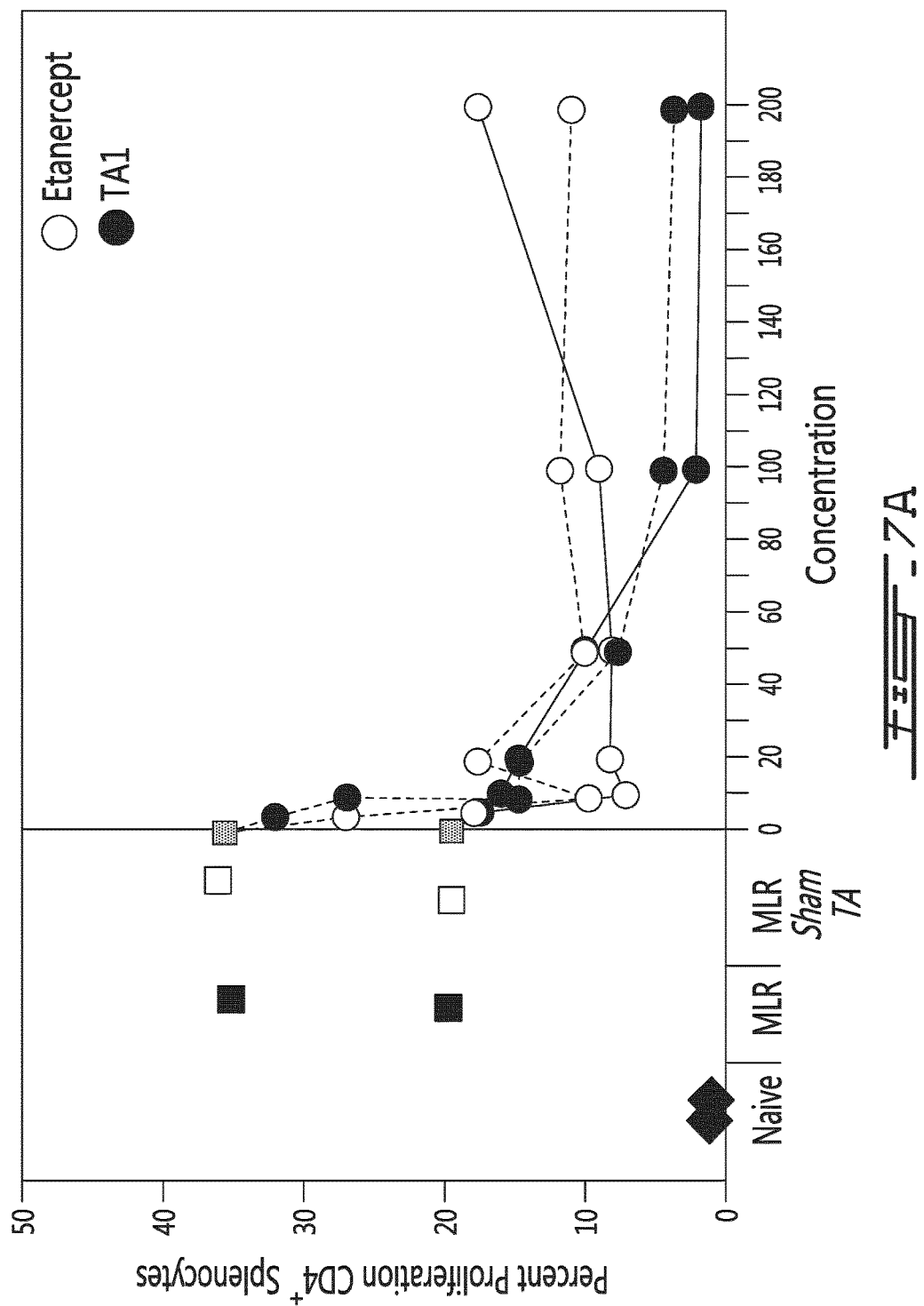
FIG. 7 compares the in vitro immunosuppressive effects of TA1 preparation and etanercept. A mixed lymphocyte reaction using Balb/c and C57Bl/6 splenocytes was conducted in the absence (■=control MLR, □=control MLR with sham TA1) or the presence of etanercept (○, x axis provides concentration in ng/mL used) or the TA1 composition (●, x axis provides concentration in μL/mL used). (A) Results are shown as the percentage of proliferation of CD4$^+$ splenocytes in function of treatment after 8 days (solid line) and 14 days (dashed line). (B) Results are shown as the percentage of proliferation of CD8$^+$ splenocytes in function of treatment after 8 days (solid line) and 14 days (dashed line).

To compare the therapeutic efficacy of the manufactured miRNA preparations, the murine TA1 preparation was directly compared to a known, clinically used, pro-tolerogenic therapeutic product (etanercept; trade name ENBREL®). TA1 and etanercept were introduced in a mouse MLR (using Blab/c and C57Bl/6 splenocytes) and the proliferation of the splenocytes were measured. As shown in FIG. 7, TA1 more efficiently repressed CD4+ splenocyte proliferation (FIG. 7A) and CD8+ splenocyte proliferation (FIG. 7B) than did etanercept. This data demonstrates that the TA1 preparation induced a much more potent immunosuppressive effect than the medicinal ingredient of the drug ENBREL®. While dosing of CBS-TA1 is expressed in μl/ml, the active component (i.e., miRNA) within the TA1 preparation is in the pg-ng range.

While the murine TA1 preparation proved effective both in vitro and in vivo in experimental models involving immunologically normal cells and animals, to test the effectiveness of the TA1 preparation, a model of autoimmune disease, NOD mice were used. In the NOD mice, autoimmune destruction of the pancreatic islets begins within approximately 10-15 weeks of birth and is confirmed by elevated blood glucose measures. The lymphocytes from pre-diabetic and diabetic animals has been obtained from the spleen, the brachial lymph node and the pancreatic lymph node. These lymphocytes have been submitted to flow cytometry using anti-IL-17A (PE) and anti-FoxP3 (Alexa 697) antibodies. As shown in FIG. 8, significant changes in the levels of Th17 and Treg lymphocytes are noted in the spleen, brachial lymph node and pancreatic lymph nodes upon conversion of NOD mice from non-diabetic to diabetic state. These changes are characterized by dramatically increased Th17 (top numbers in each panels) and significantly decreased Treg (lower numbers in each panels) lymphocytes.

Murine TA1 preparations were obtained from normal Balb/c or C57Bl/6 mice and 100 μL was administered intravenously once to 10 week-old NOD mice (n=5). Naïve NOD mice were used for comparison. The administration of TA1 caused a shift in immune modulation at day 5 post treatment towards immune tolerance by decreasing the circulating blood levels of pro-inflammatory Th17 cells by over 50% (0.17% versus 0.38% for untreated NOD mice).

Figure 9A:
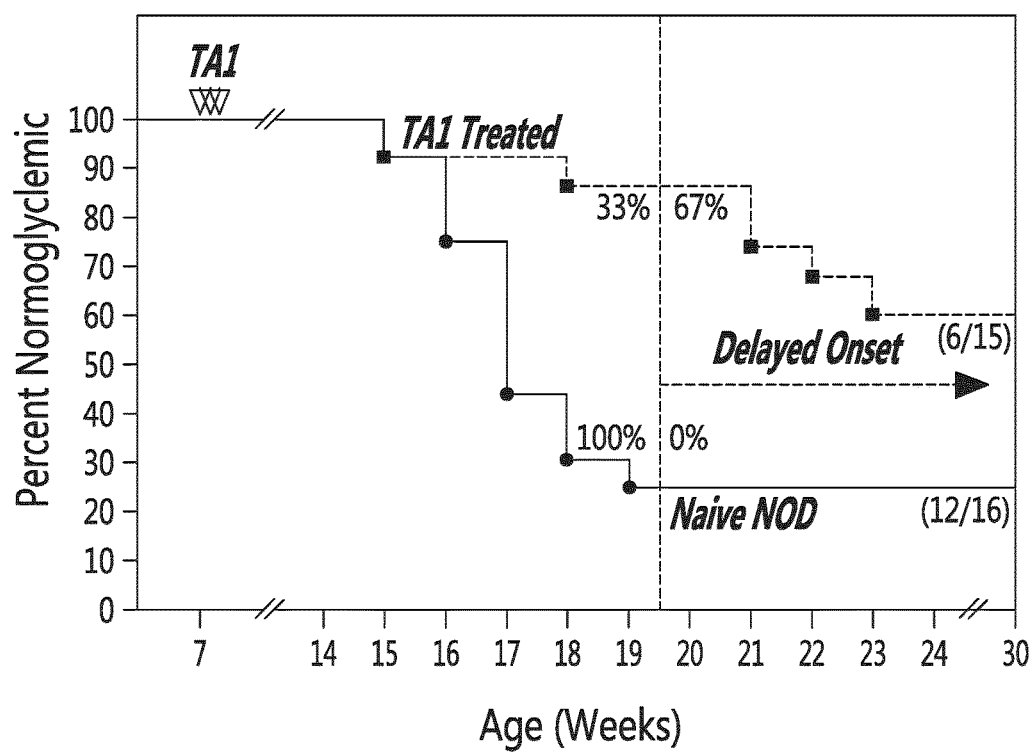
FIG. 9 illustrates the effects of the TA1 preparations in NOD mice. TA1 acellular preparation was manufactured from mice treated with mPEG-modified allogeneic splenocytes five (5) days post treatment. The purified miRNA composition was administered thrice (100 μl per i.v. injection at days 0, 2 and 4) to 7 week-old NOD mice (n=15). Control mice (n=16; untreated) were injected with 100 μl of saline. (A) The glycaemia of the animals were determined during the weeks following the treatment. Results are shown as the percentage of normoglycemic animals in function of age (in weeks) and treatment (dashed line=TA1-treated, solid line=naïve untreated animals). In this model, diabetes begins to occur at approximately 15 weeks. Between weeks 15 and 20, 75% of untreated mice developed hyperglycemia (i.e. diabetes) compared to 13% of TA1-treated mice. After 30 weeks, 9 out of the 15 animals treated with TA1 were still considered normoglycemic compared to only 4 out of the 16 for untreated animals. In TA1-treated mice developing diabetes (6 out of 15), 67% of the animals exhibited delayed onset (post 20 weeks) relative to untreated mice where 100% of the diabetic mice arose prior to 20 weeks of age. (B) The Treg/Th17 ratio in the pancreatic lymph node was determined during the weeks following treatment. Results are shown as the log in Treg/Th17 ratio in function of age (weeks) in mice developing diabetes (open circles/dashed line=untreated mice; closed circles/solid=TA1-treated mice). At 30 weeks of age, all surviving mice were sacrificed and the Treg/Th17 ration was determined (open star=untreated mice±range; closed star=TA1-treated mice±range). (C) The Treg/Th17 ratio in the pancreatic lymph note was determined in healthy 20-week old Balb/c (198) and C57Bl/6 (91.5), 7-week old NOD (103), diabetic NOD (control animals (4.7) and TA1-treated (70) animals) as well as 30-week old non-diabetic NOD mice (control animals (286) and TA1-treated animals (255)).
Figure 9B:
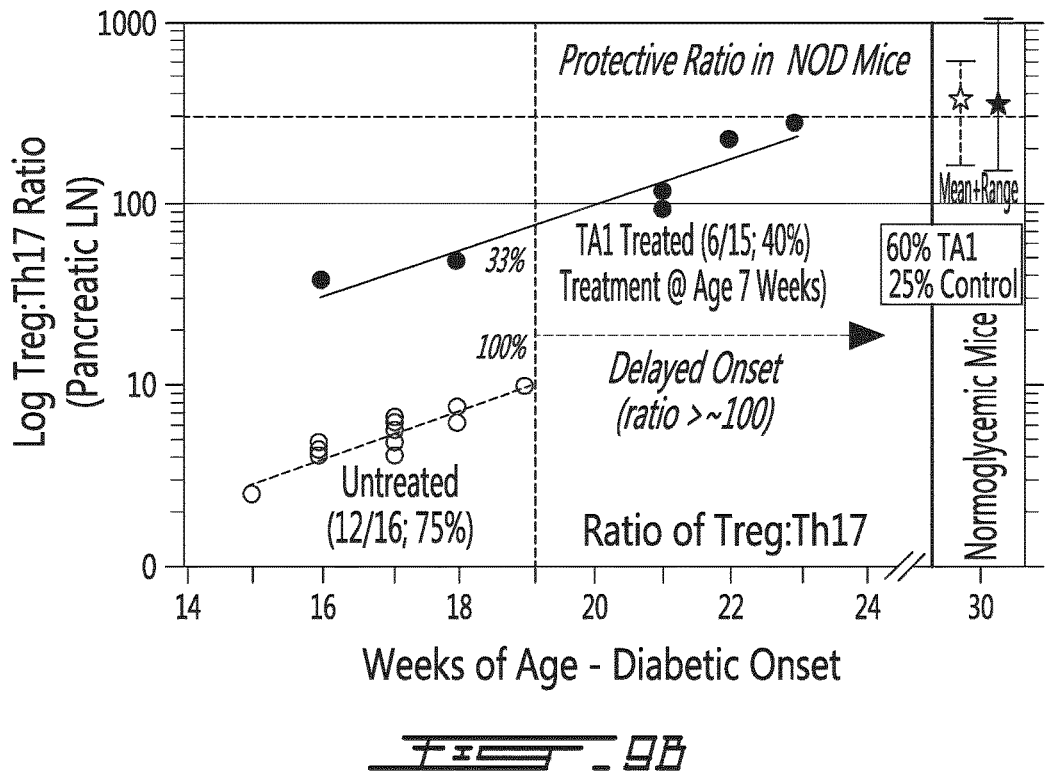
Figure 9C:
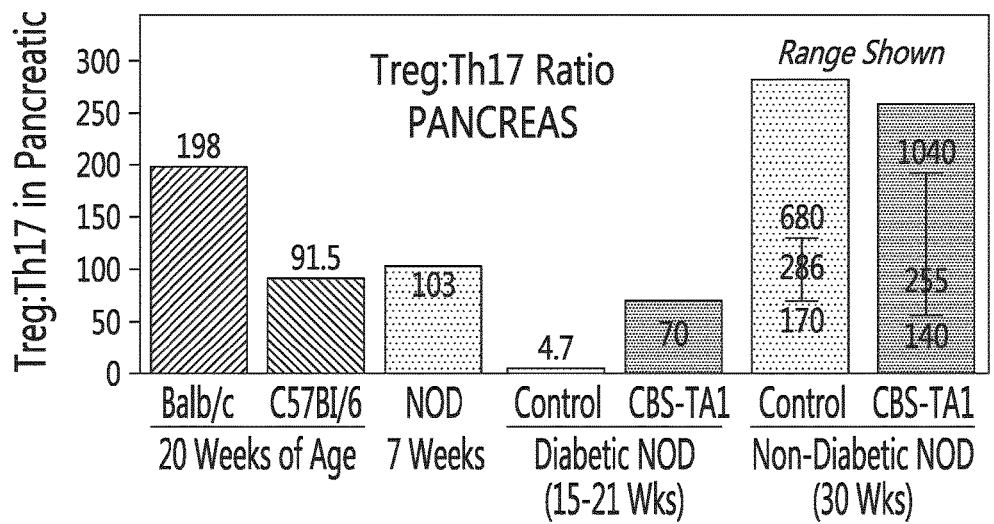

As shown in FIG. 9A, the administration of the murine TA1 preparations (3 times 100 μl i.v. injections each 2 days apart) to 7 week-old NOD mice NOD mice yielded significant protection against progression to diabetes. Results are shown as the percentage of normoglycemic animals in function of age (in weeks) and treatment (dashed line=TA1, solid line=naïve NOD mice). In this model, diabetes begins to occur at approximately 15 weeks. Between weeks 15 and 20, 75% of untreated mice developed hyperglycemia (i.e. diabetes) compared to 13% of TA1-treated mice. After 30 weeks, 9 out of the 15 animals treated with TA1 remained normoglycemic compared to only 4 out of the 16 for untreated animals. Even in the TA1-treated mice that developed diabetes (6 out of 15), TA1 treatment significantly delayed the onset of diabetes with 67% of the diabetic animals occurring at greater than 20 weeks of age. In contrast, 100% of the diabetic control NOD mice arose before 20 weeks of age. Moreover, the onset of diabetes correlated with the Treg:Th17 ratio as shown in FIG. 9B. A high Treg:Th17 ratio protected against, or delayed, the age of onset for overt diabetes. As shown, untreated diabetic NOD mice demonstrated lower Treg/Th17 ratios compared to diabetic TA1-treated NOD mice. The higher Treg/Th17 ratio of the TA1-treated mice similarly correlated with a delayed onset of diabetes in the mice that developed overt disease. At 30 weeks of age, all survivor (i.e. normoglycemic) mice were sacrificed and their Treg/Th17 ratios determined As shown in FIG. 9B, very high Treg/Th17 ratio were characteristic of normoglycemic animals in both the untreated and TA1-treated groups. The importance of the Treg/Th17 ratio is further shown in FIG. 9C in which the ratio is described in normal mouse strains (Balb/c and C57/Bl6) pre-diabetic NOD mice (7 weeks of age), diabetic control and TA1-treated NOD mice as well as normoglycemic control and TA1-treated NOD mice. As shown by the normoglycemic animals, a significantly higher (p<0.0001) Treg/Th17 ratio was observed relative to diabetic mice.

Figure 10A:
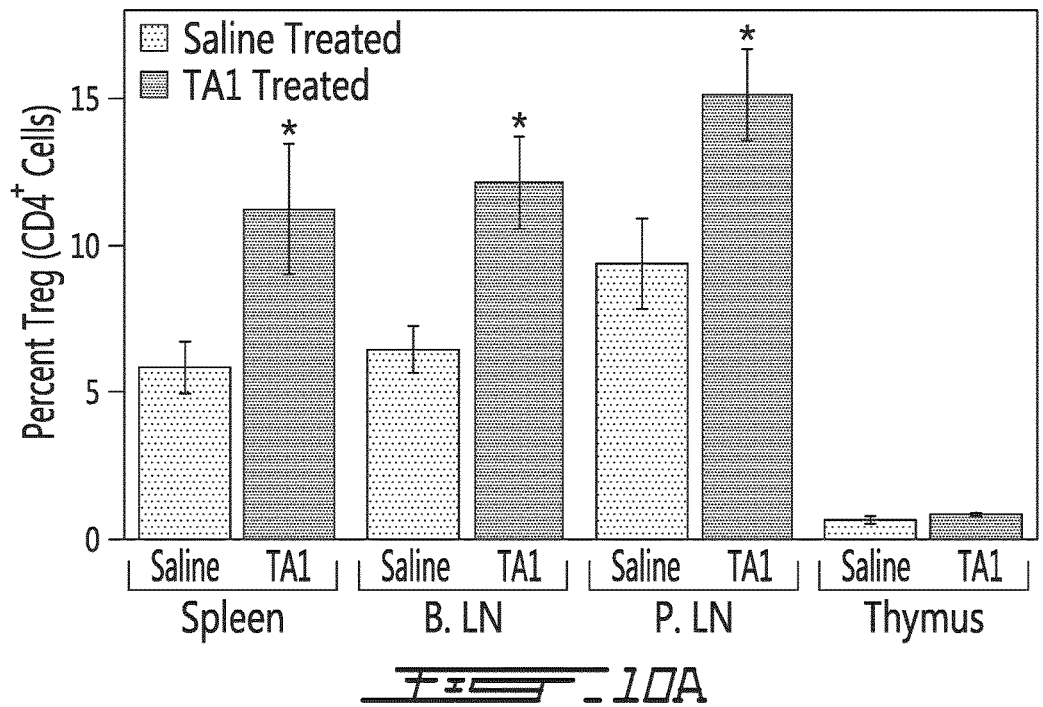
FIG. 10 illustrates the in vivo effects of TA1 preparations on tolerogenic/anergic immune cell populations. NOD mice (7 week-old) were treated trice (100 μL i.v. at days 0, 2 and 4) with either saline or the murine TA1 preparations. As mice became diabetic or at 30 weeks of age, immune populations were characterized in the spleen, the brachial lymph node, the pancreatic lymph node and, for Treg cells, the thymus. In this figure, light grey bars refer to saline-treated animals and dark grey bars refers to TA1-treated animals. (A) Results are shown as the percentage of Foxp3$^+$ (Treg) cells (in function of total CD4$^+$ cells) in function of treatment. (B) Results are shown as the percentage of TGF-β$^+$ (Treg and Th2) cells (in function of total CD4$^+$ cells) in function of treatment. (C) Results are shown as the percentage of IL-4$^+$ (Th2 and naive) cells (in function of total CD4$^+$ cells) in function of treatment. (D) Results are shown as the percentage of IL-10$^+$ (Treg and Th2) cells (in function of total CD4$^+$ cells) in function of treatment. (E) Results are shown as the percentage of CD62L$^+$ (Treg) cells (in function of total CD4$^+$ cells) in function of treatment. (F) Results are shown as the percentage of CD152$^+$ cells (in function of total CD4$^+$ cells) in function of treatment. (G)
Figure 10B:
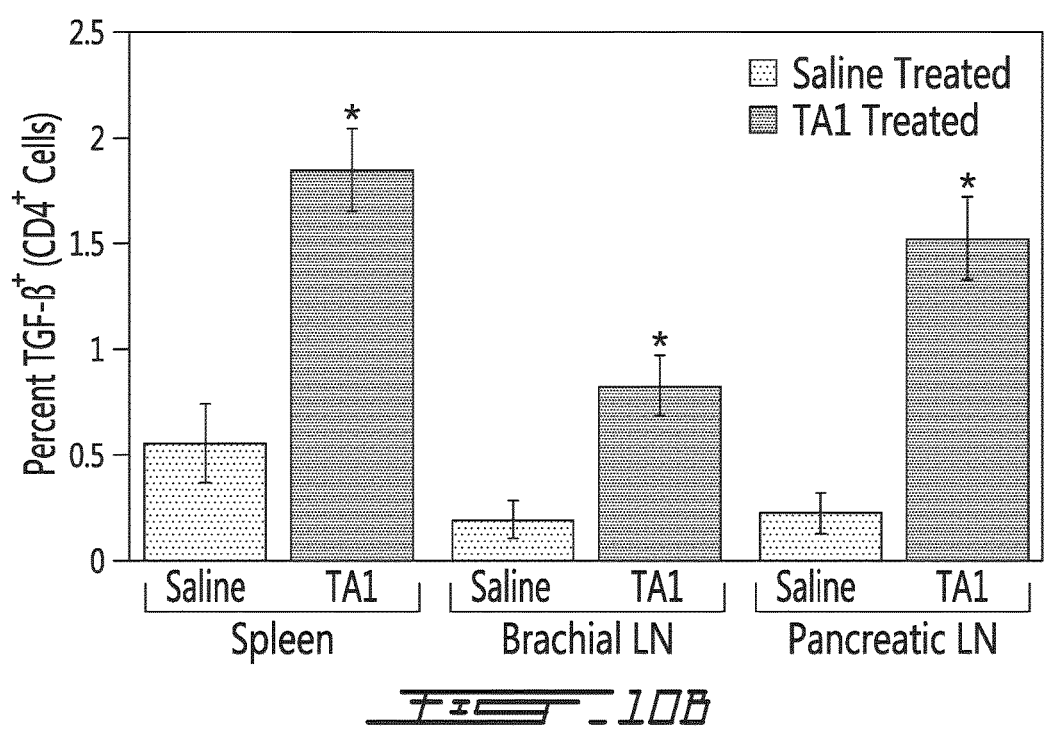
Figure 10C:
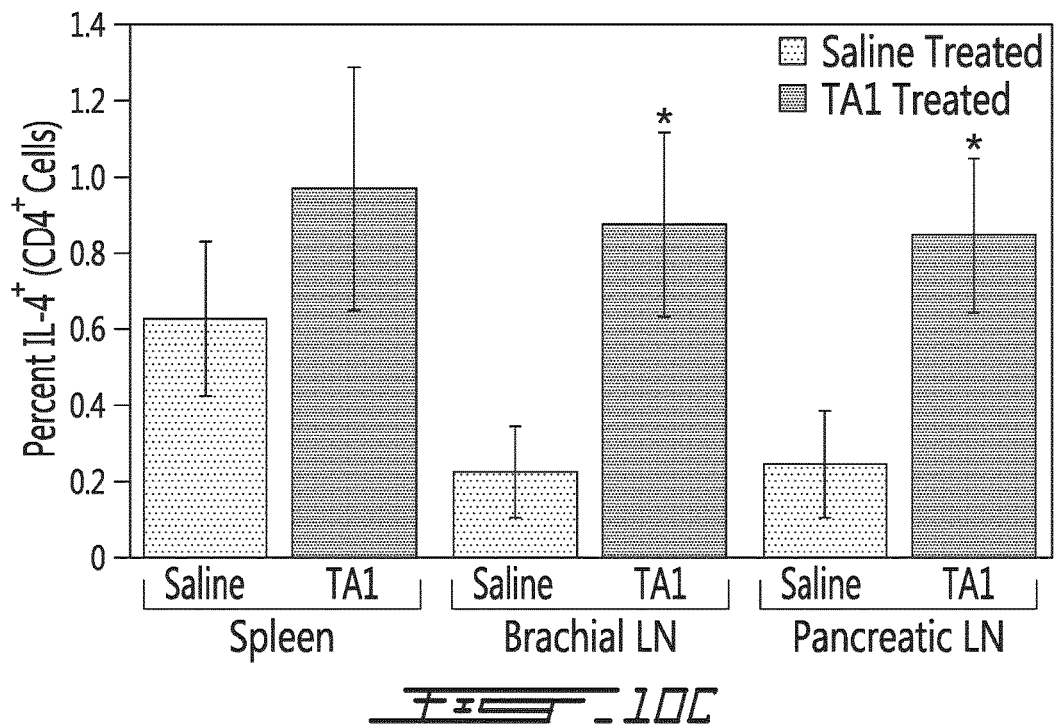
Figure 10D:
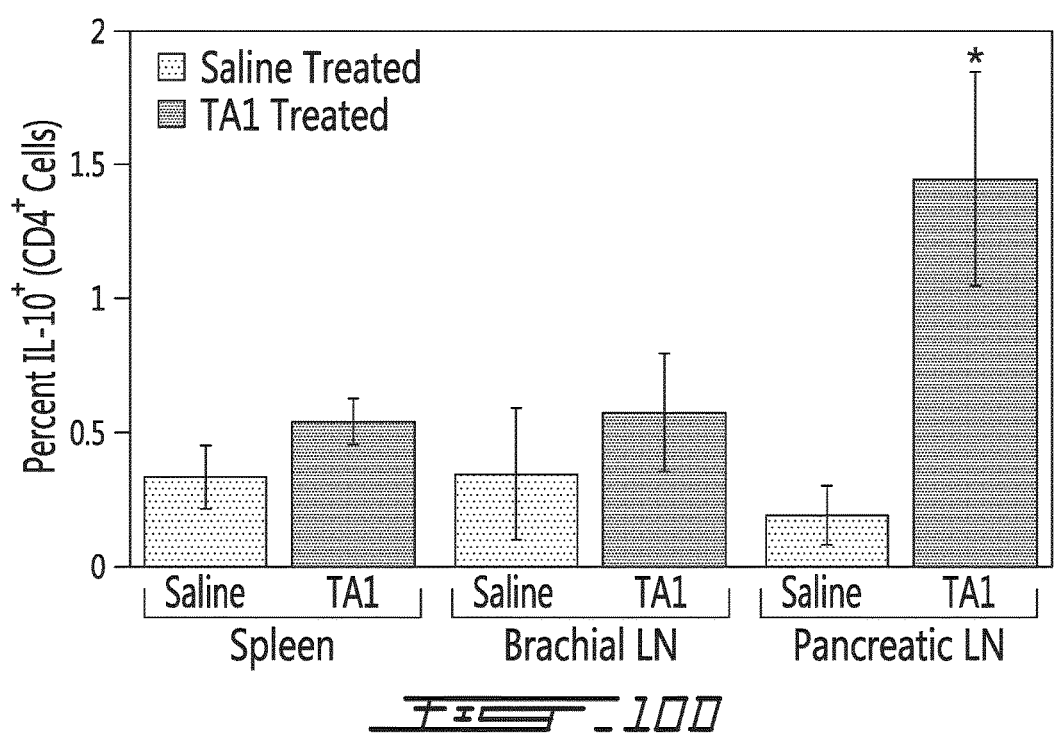
Figure 10E:
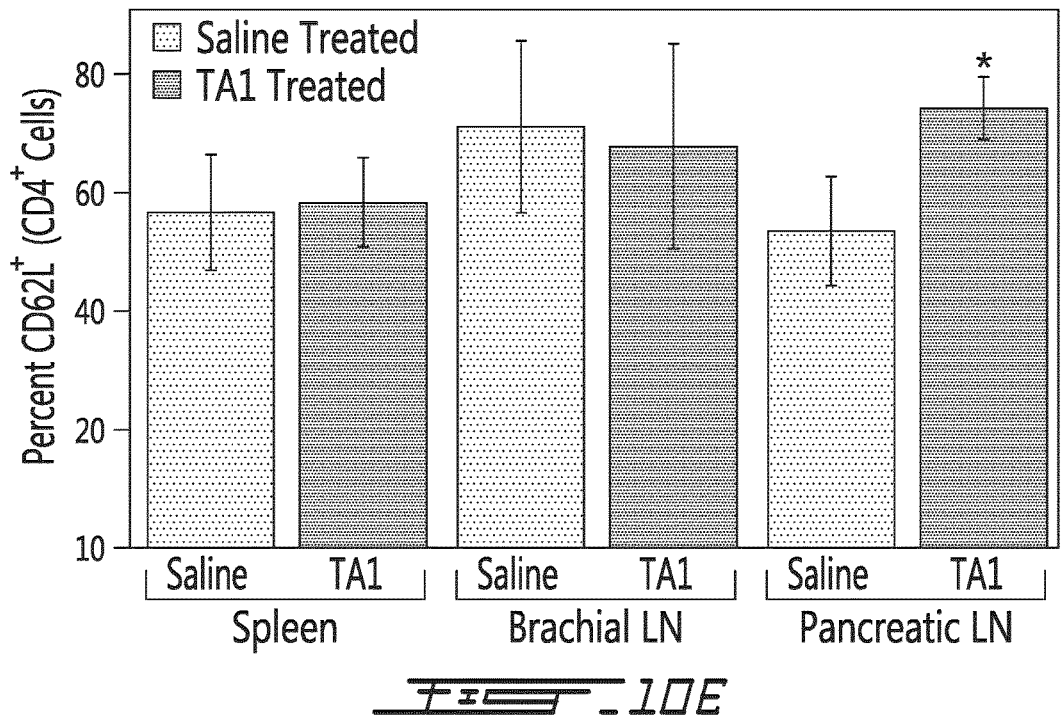
Figure 10F:
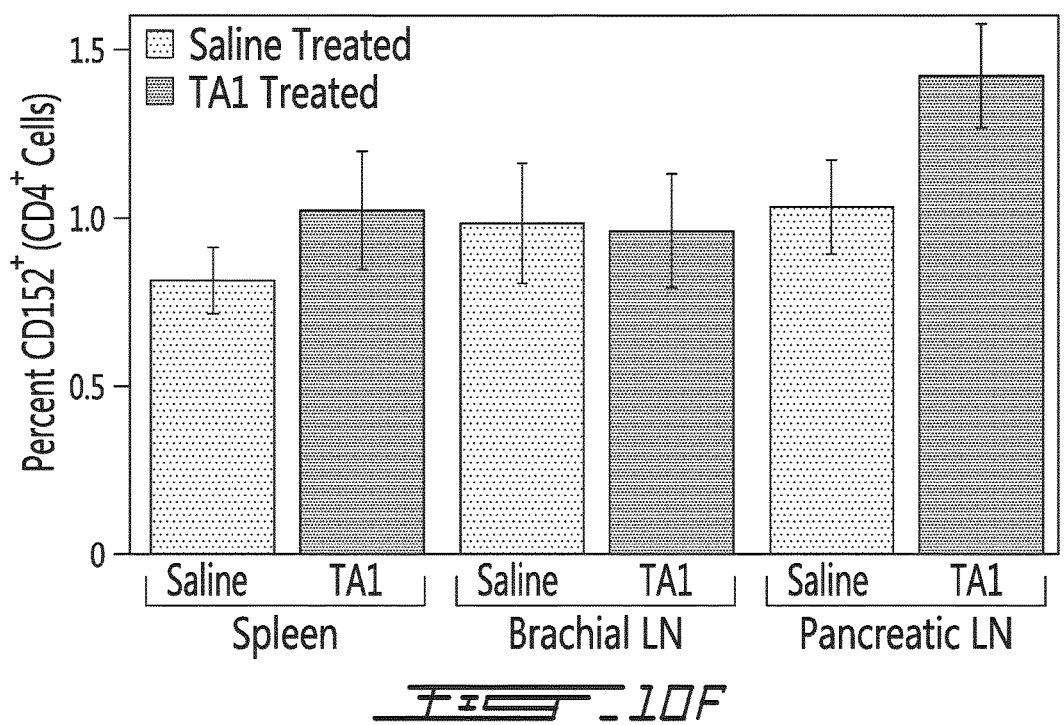
Figure 10G:
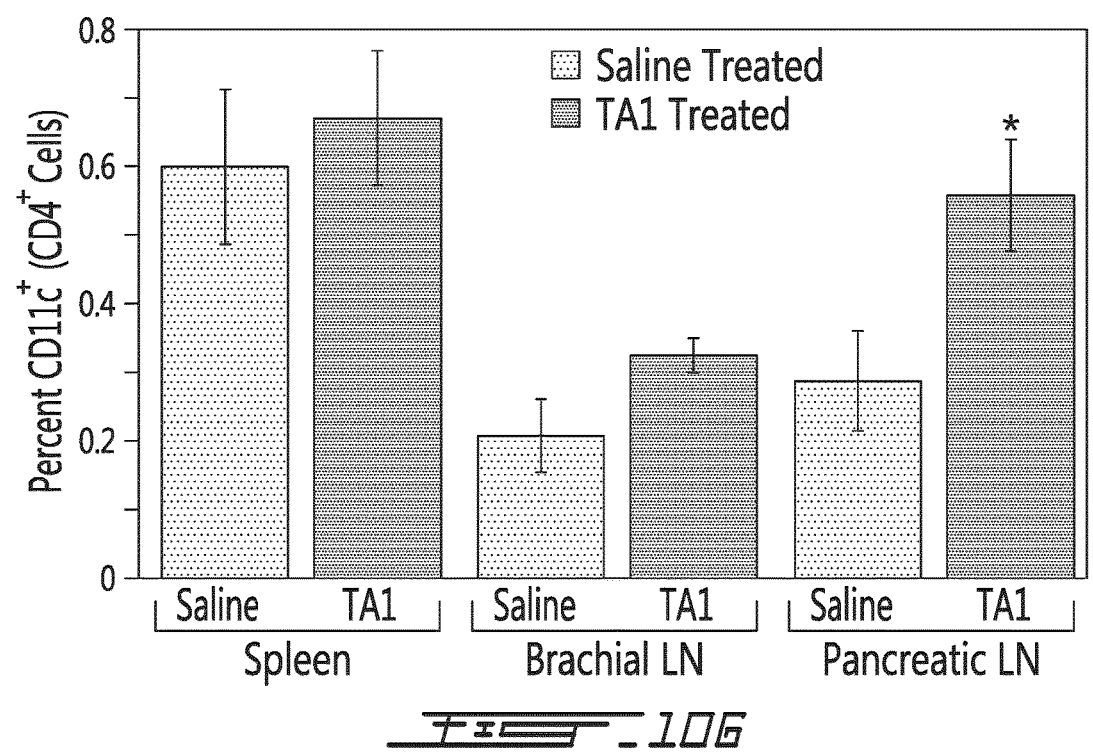

The administration of the murine TA1 preparations to NOD mice caused a systemic and/or local increase in pro-tolerogenic leukocytes. Leukocyte populations were quantitated at time of sacrifice of the mice (weeks 15-30). Treatment at 7 weeks of age with TA1 yielded a persistent and significant increase in Treg cells in all tissues of the NOD mouse measured with the exception of the thymus (FIG. 10A). This data suggest that TA1 exerts a potent immunomodulatory effect on lymphatic organs. Tregs counter-balance/attenuate proinflammatory lymphocytes such as Th17 and Th1 cells. The administration of murine TA1 similarly caused an increase in the expression of TGF-8. As shown in FIG. 10B, the TA1 preparation increased TGF-β$^+$ cells in the treated mice. TGF-β counter-balance/attenuate proinflammatory lymphocytes such as Th17 and Th1 cells. Exogenous TGF-β has previously been shown to prevent autoimmune diabetes in NOD mice. The administration of TA1s increased the level of expression of IL-4$^+$, a marker of Th2 cells (FIG. 10C), further confirming its immunomodulatory effect on lymphatic organs. The administration of TA1s increased the level of expression of IL-10$^+$, another marker of Th2 cells (FIG. 10D) as well as the percentage of CD62L$^+$ cells (FIG. 10E), CD152+ cells (FIG. 10F) and CD11c$^+$ cells (FIG. 10G). This modulation was however more pronounced in the pancreas of the treated animals. Moreover, histopathological analysis demonstrated that TA1 treatment prevented/diminished leukocyte infiltration and destruction of the pancreatic islets (data not shown). While >95% of islets examined from untreated NOD mice (both diabetic and 30 week old non-diabetic) exhibited overt insulitis (60%) or perinsulitis (40%), less than 10% of islets from the non-diabetic 30 week old TA1 mice exhibited overt insulitis while ~60 percent of islets were completely normal. In TA1-treated mice that became diabetic, approximately 35% of islets were normal in appearance while 25% demonstrated overt insulitis, with the remained of mice exhibiting varying degrees of peri-insulitis.

Figure 11A:
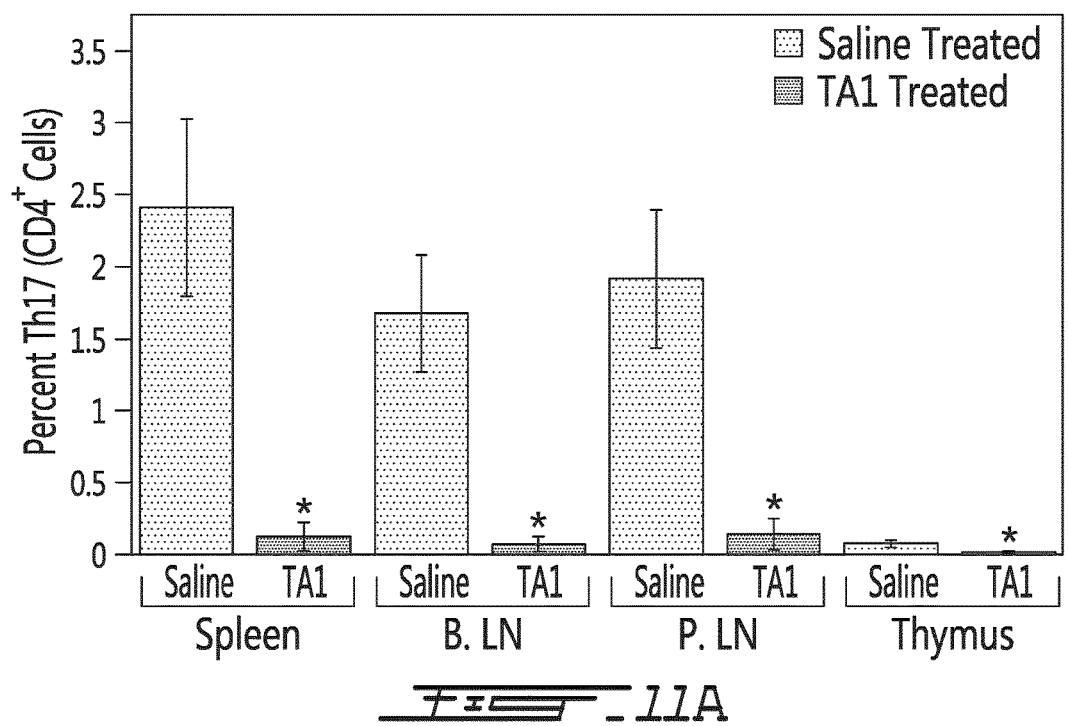
Figure 11B:
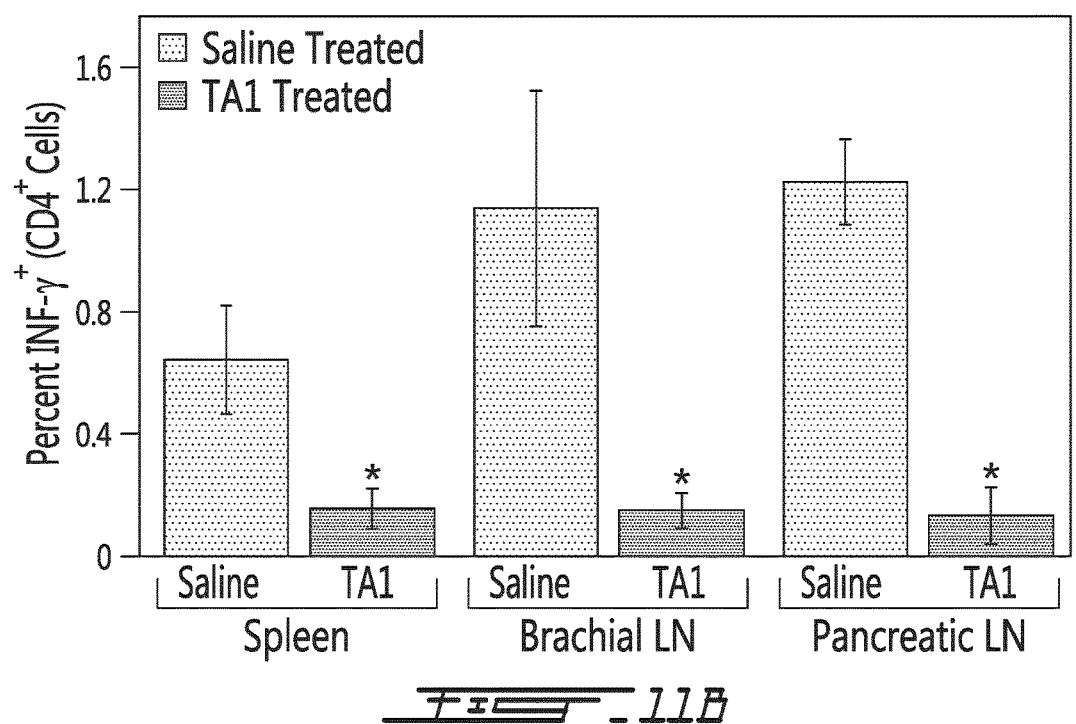
Figure 11C:
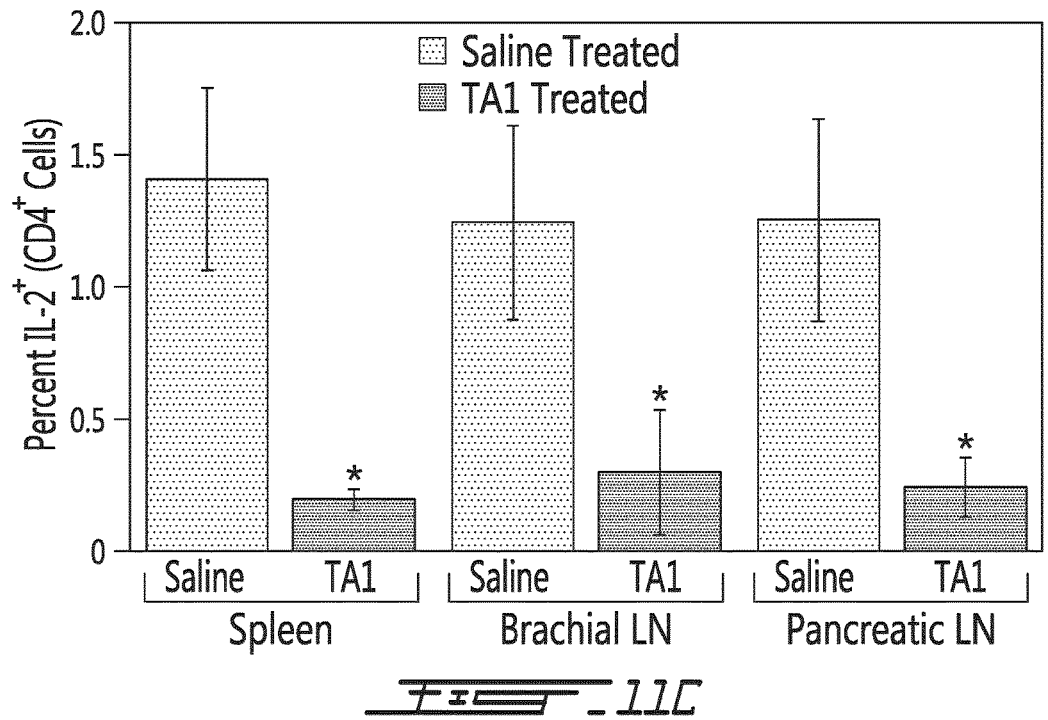
Figure 11D:
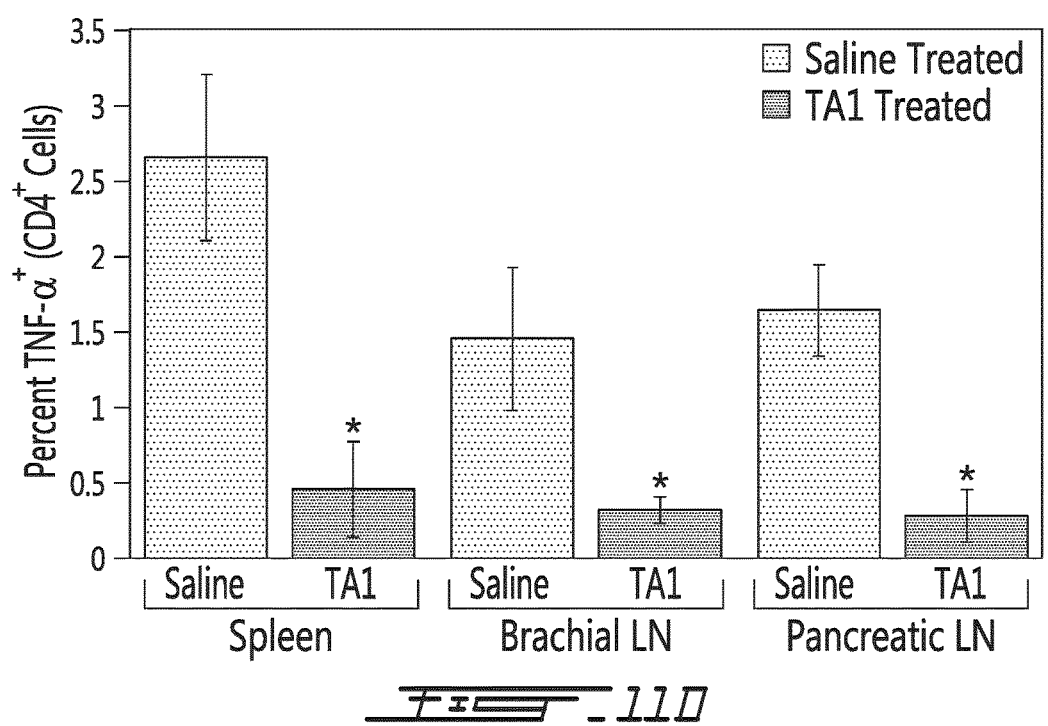
Figure 11E:
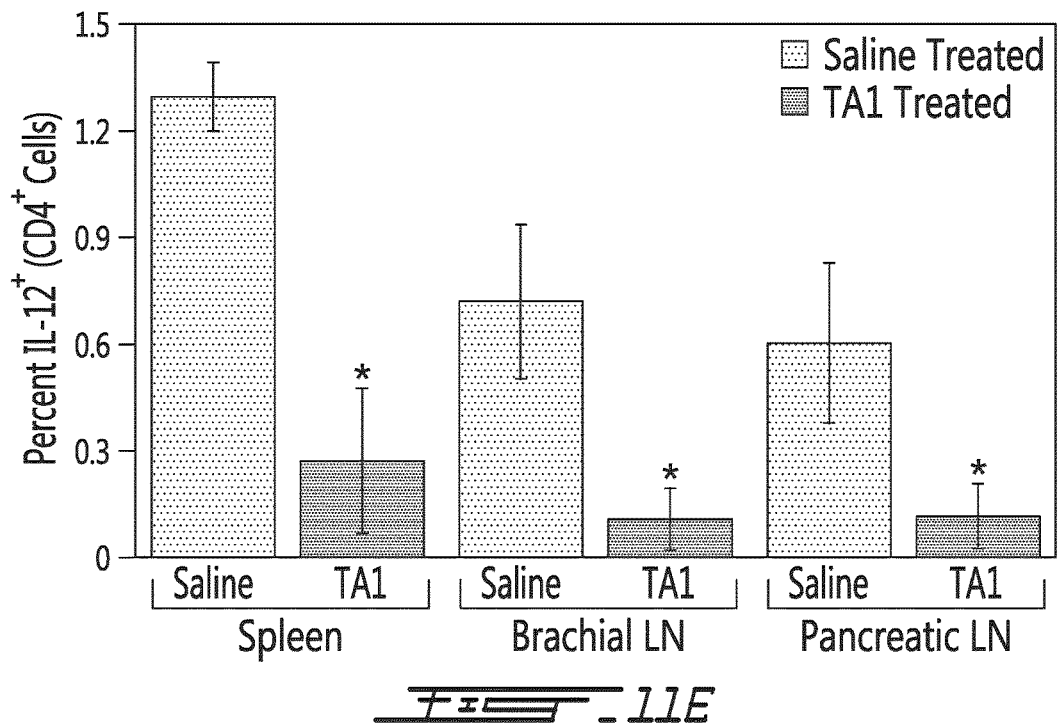
Figure 11F:
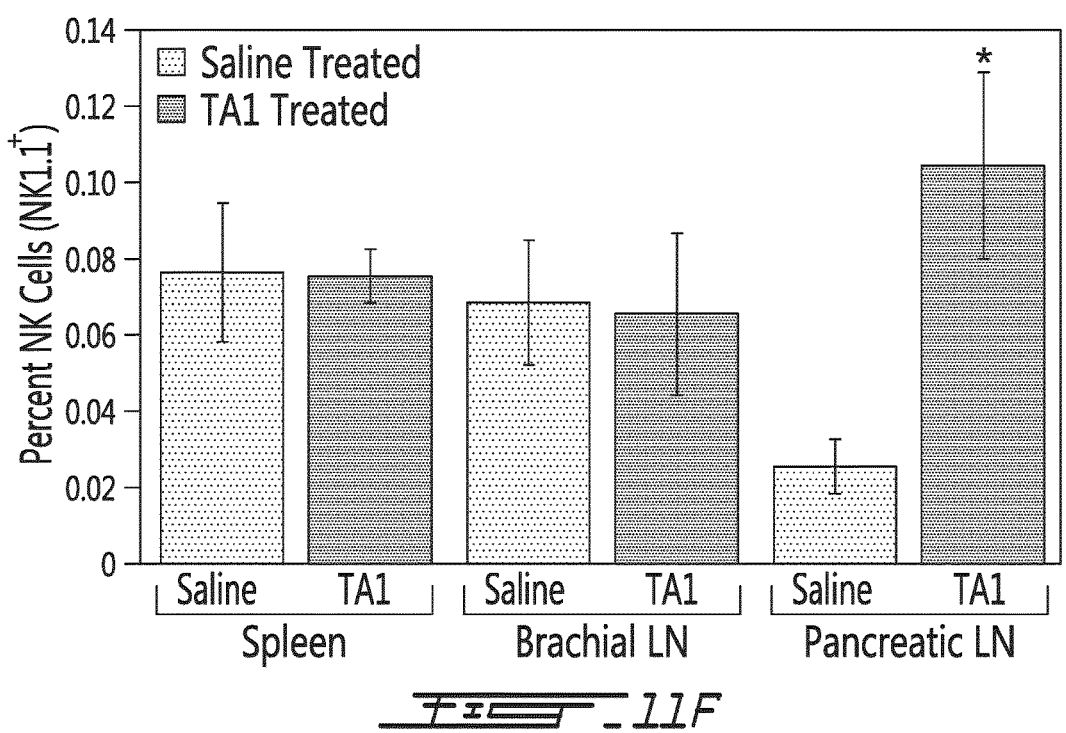

The administration of the murine TA1 preparations to NOD mice also caused a decrease in pro-inflammatory Th17 cells and Th1 cells, as shown by the decrease in the percentage of IL-17A$^+$ cells (FIG. 11A) as well as the decrease in the percentage of INF-γ$^+$ cells (FIG. 11B), IL-2$^+$ cells (FIG. 11C), TNF-α$^+$ cells (FIG. 11D) and IL-12$^+$ cells (FIG. 11E). This data suggest that the TA1 preparations prevented Th17/Th1 upregulation in the treated mice. As it is know in the art, Th1 and Th17 lymphocytes mediate islet cell destruction. Interestingly, the administration of TA1s caused a significant increase in the level of NK cells (as measured by the expression of NK1.1+ cells on FIG. 11F) in the pancreas, but not in other tissues. It is believed that the differentially induced NK cells in the pancreas destroys autoreactive (i.e. inflammatory) cells providing an additional immunomodulatory mechanism resulting in decreased diabetes.

Further, it has been shown are that the administration of TA1s increases B10$^+$ (B regulatory) cells and tolerogeneic DC cell levels while decreasing APC associated with inflammation (data not shown) further confirming the pro-tolerogenic effects of TA1 s.

Example IV—miRNA Characterization of Acellular Protolerogenic Preparations

In order to characterize the constituents of the miRNA preparations, the miRNA of conditioned medium collected at 72 hours from resting human PBMC, a human control MLR (using two HLA disparate PBMC populations), and a mPEG MLR (using the same two allogeneic PBMC populations wherein one population is modified with a polymer, e.g. mPEG) (this human miRNA preparation is herewith referred to as TA2) and compared via qPCR analysis. The combined average of the resting Donor A and resting Donor B (i.e., resting AB) were used, unless otherwise noted, for baseline in all analyses.

As shown in FIG. 12A, when the miRNA population from the conditioned medium from a control MLR is compared to the miRNA population of the supernatant of resting cells, using a volcano plot analysis, at least five different miRNAs are differentially expressed (e.g. increased) by statistical significance ($p<0.01$ for miR-9-5p, miR-155-5p, miR-206, miR-147a and $p<0.05$ for miR-214-3p) and at least one miRNA is modulated by at least a $\log_2$ (e.g. miR-302a-3p). In contrast, as shown in FIG. 12B, when the miRNA population from the conditioned medium from a mPEG MLR (e.g. TA2) is compared, using a volcano plot analysis, with the miRNA population of the supernatant of resting cells, at least one miRNA is differentially expressed (e.g. increased) by statistical significance ($p<0.05$ for miR-214-3p) and at least one miRNA is modulated by at least a $\log_2$ fold (e.g. miR-149-5p). A direct comparison of mPEG-MLR (e.g. TA2) to the control MLR as shown in FIG. 12C, demonstrates that at least two miRNAs are differentially expressed by volcano statistical significance ($p<0.01$ for miR-155-5p and $p<0.05$ for miR-9-5p) and at least two miRNAs are modulated by at least a $\log_2$ (e.g. miR-183-5p and mir-147a).

On FIG. 12, nine miRNA species were identified. These miRNA species were selected because they were considered to be differentially expressed as determined by clustergram analysis between the control MLR and mPEG-MLR. The miRNA species identified with 1, 2, 3, 5, 6, 8 and 9 showed increased abundance in the mPEG MLR relative to the control MLR. The miRNA species identified with 4 has a relative abundance similar in both the control MLR and mPEG-MLR and elevated relative to resting cells.

Further characterization of the miRNA population of the conditioned medium of the control MLR and mPEG MLR is provided in fold change analysis. FIG. 13 provides a summary of the fold regulation of the purified miRNA preparations differentially expressed in the conditioned medium of a control MLR and a mPEG MLR (TA2) when compared to the conditioned medium of resting cells. FIG. 14 provides a subset of the miRNAs presented in FIG. 13 and exhibiting at least a $\log_2$ fold modulation when compared to resting cells. As indicated in FIG. 14, a subpopulation of miRNAs are decreased in the conditioned medium from the mPEG MLR and increased in the conditioned medium from the control MLR (miR-183-5p, miR-203a, miR363-3p). As also indicated in FIG. 14, another subpopulation of miRNAs are increased in the conditioned medium from the mPEG MLR and decreased in the conditioned medium from the control MLR (miR-21-5p, miR-27a-3p, miR27b-3p, miR-298, miR-34a-5p, let-7a-5p, let-7e-5p, miR-132-3p).

REFERENCES

Anderson M S, Bluestone J A. The NOD mouse: a model of immune dysregulation. Annu Rev Immunol. 2005; 23:447-85.

Bradley A J, Test S T, Murad K L, Mitsuyoshi J, Scott M D. Interactions of IgM ABO antibodies and complement with methoxy-PEG-modified human RBCs. Transfusion 2001; 41:1225-33.

Bradley A J, Scott M D. Immune complex binding by immunocamouflaged [poly(ethylene glycol)-grafted] erythrocytes. Am J Hematol 2007; 82:970-5.

Chen A M, Scott M D. Current and future applications of immunological attenuation via pegylation of cells and tissue. BioDrugs 2001; 15:833-47.

Chen A M, Scott M D. Immunocamouflage: prevention of transfusion-induced graft-versus-host disease via polymer grafting of donor cells. J Biomed Mater Res A 2003; 67:626-36.

Chen A M, Scott M D. Comparative analysis of polymer and linker chemistries on the efficacy of immunocamouflage of murine leukocytes. Artif Cells Blood Substit Immobil Biotechnol 2006; 34:305-22.

Le Y, Scott M D. Immunocamouflage: the biophysical basis of immunoprotection by grafted methoxypoly(ethylene glycol) [mpeg]. Acta Biomater 2010; 6:2631-41.

McCoy L L, Scott M D. Broad spectrum antiviral prophylaxis: inhibition of viral infection by polymer grafting with methoxypoly(ethylene glycol). In: PF T, editor. Antiviral drug discovery for emerging diseases and bioterrorism threats. Hoboken, N J: Wiley & Sons; 2005. p. 379-95.

Murad K L, Gosselin E J, Eaton J W, Scott M D. Stealth cells: prevention of major histocompatibility complex class II-mediated T-cell activation by cell surface modification. Blood 1999A; 94:2135-41.

Murad K L, Mahany K L, Brugnara C, Kuypers F A, Eaton J W, Scott M D. Structural and functional consequences of antigenic modulation of red blood cells with methoxypoly (ethylene glycol). Blood 1999B; 93:2121-7.

O'Neill D W, Bhardwaj N. Differentiation of peripheral blood monocytes into dendritic cells. Curr Protoc Immunol; 2005. Chapter 22: Unit 22F.4.

Scott M D, Murad K L, Koumpouras F, Talbot M, Eaton J W. Chemical camouflage of antigenic determinants: stealth erythrocytes. Proc Natl Acad Sci USA 1997; 94:7566-71.

Sutton T C, Scott M D. The effect of grafted methoxypoly (ethylene glycol) chain length on the inhibition of respiratory syncytial virus (RSV) infection and proliferation. Biomaterials 2010; 31:4223-30.

Wang D, Toyofuku W M, Chen A M, Scott M D. Induction of immunotolerance via mPEG grafting to allogeneic leukocytes. Biomaterials. 2011 December; 32(35):9494-503.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of increasing a ratio of the level of regulatory T (Treg) cells to the level of pro-inflammatory T cells in a subject in need thereof, said method comprising:
    (i) associating a low-immunogenic biocompatible polymer to a cytoplasmic membrane of a first leukocyte to obtain a first modified leukocyte, wherein the low-immunogenic biocompatible polymer is polyethylene glycol (PEG), 2-alkyloxazoilne (POZ), or hyperbranched polyglycerol (HPG);
    (ii) contacting the first modified leukocyte with a second leukocyte under conditions to allow a pro-tolerogenic allo-recognition to provide a conditioned preparation, wherein the first leukocyte is allogeneic to the second leukocyte;
    (iii) selecting miRNA components having an individual average molecular weight of less than about 10 kDa from the conditioned preparation under conditions to inhibit RNA degradation by a RNAse and to maintain a relative abundance of each of the miRNA components so as to obtain a composition enriched in acellular pro-tolerogenic components;
    (iv) formulating the composition of step (iii), under conditions to inhibit RNA degradation, in the pro-tolerogenic preparation for administration to the subject; and
    (v) administering to the subject a therapeutic amount of the pro-tolerogenic preparation of step (iv);
    wherein the administration of the pro-tolerogenic preparation increases the ratio in the subject and wherein the increased ratio between the level of Treg cells and the level of pro-inflammatory T cells is for treating or alleviating the symptoms associated to an auto-immune disease afflicting the subject.

2. The method of claim 1, where the process further comprises covalently binding the low-immunogenic biocompatible polymer to a membrane-associated protein of the cytoplasmic membrane of the first leukocyte.

3. The method of claim 1, wherein the low-immunogenic biocompatible polymer is a polyethylene glycol (PEG).

4. The method of claim 3, wherein the polyethylene glycol is a methoxy polyethylene glycol (mPEG).

5. The method of claim 4, wherein the process further comprises covalently binding the mPEG by contacting the first leukocyte with methoxypoly(-ethylene glycol) succinimidyl valerate.

6. The method of claim 1, wherein step (ii) of the process occurs in vitro.

7. The method of claim 6, wherein the conditioned preparation is a supernatant of a cell culture of the first leukocyte and the second leukocyte.

8. The method of claim 6, wherein the process further comprises preventing one of the first leukocyte or the second leukocyte from proliferating prior to step (ii).

9. The method of claim 1, wherein step (ii) of the process occurs in vivo and comprises administering the first modified leukocyte to a mammal having the second leukocyte.

10. The method of claim 9, wherein the conditioned preparation is plasma.

11. The method of claim 9, where the process further comprises preventing the first leukocyte from proliferating prior to administration to the mammal.

12. The method of claim 1, wherein step (iii) of the process comprises filtering out components having the individual average molecular weight of more than about 10 kDa from the conditioned preparation.

13. The method of claim 1, wherein step (iv) of the process comprises formulating the composition for intravenous administration to the subject.

14. The method of claim 13, wherein step (v) of the process comprises administering the composition intravenously to the subject.

15. The method of claim 1, wherein the first leukocyte and/or the second leukocyte is a T cell.

16. The method of claim 15, wherein the T cell is a CD4-positive T cell.

17. The method of claim 15, wherein the T cell is a CD8-positive T cell.

18. The method of claim 1, wherein the auto-immune disease is at least one of type I diabetes, rheumatoid arthritis, multiple sclerosis, psoriasis, lupus, immune thrombocytopenia, experimental autoimmune encephalomyelitis, autoimmune uveitis, inflammatory bowel disease, scleroderma and Crohn's disease.

* * * * *